US012576081B2

(12) United States Patent
Yeager et al.

(10) Patent No.: US 12,576,081 B2
(45) Date of Patent: Mar. 17, 2026

(54) METHODS AND COMPOSITIONS FOR IMPROVING EXERCISE PERFORMANCE, SINGLE VENTRICULAR PERFORMANCE, CARDIAC OUTPUT AND MYOCARDIAL PERFORMANCE INDEX (MPI) IN SINGLE VENTRICULAR HEART DISEASE, USING UDENAFIL COMPOSITIONS

(71) Applicants: MEZZION PHARMA CO., LTD., Seoul (KR); THE CHILDREN'S HOSPITAL OF PHILADELPHIA, Philadelphia, PA (US)

(72) Inventors: James L. Yeager, Lake Forest, IL (US); David J. Goldberg, Philadelphia, PA (US); Stephen M. Paridon, Strafford, PA (US)

(73) Assignees: Mezzion Pharma Co., Ltd., Seoul (KR); The Children's Hospital of Philadelphia, Philadelphia, PA (US)

( * ) Notice: Subject to any disclaimer, the term of this patent is extended or adjusted under 35 U.S.C. 154(b) by 200 days.

(21) Appl. No.: 16/938,642

(22) Filed: Jul. 24, 2020

(65) Prior Publication Data

US 2024/0197736 A1    Jun. 20, 2024

Related U.S. Application Data

(60) Provisional application No. 63/023,070, filed on May 11, 2020, provisional application No. 62/936,497,
(Continued)

(51) Int. Cl.
*A61K 31/519* (2006.01)
*A61K 9/20* (2006.01)
(Continued)

(52) U.S. Cl.
CPC .......... *A61K 31/519* (2013.01); *A61K 9/2009* (2013.01); *A61K 9/2013* (2013.01);
(Continued)

(58) Field of Classification Search
CPC ...... A61K 31/519; A61K 9/2013; A61P 43/00
See application file for complete search history.

(56) References Cited

U.S. PATENT DOCUMENTS 10,137,128 B2 * 11/2018 Yeager .................. A61K 31/522
10,653,698 B2 * 5/2020 Yeager .................. A61K 31/00
(Continued)

FOREIGN PATENT DOCUMENTS

CA      3128705 A1 * 2/2016 ........... C07D 487/04
EC      SP088311 A     6/2008
(Continued)

OTHER PUBLICATIONS

Ghosh, Anaerobic Threshold: Its Concept and Role in Endurance Sport, Malaysian Journal of Medical Sciences, Jan. 2004, pp. 24-36 (Year: 2004).*
AHA names top heart disease and stroke research advances of 2019, American Heart Association, 2019, (5 pages).
Albouaini K et al., Cardiopulmonary exercise testing and its application, Heart, 2007, 93(10):1285-1292.
Amrhein V et al., Retire statistical significance, Nature, 2019, 567:305-307.
Center for Drug Evaluation and Research, Application No. 203109Orig1s000, Summary Review, 2012 (19 pages).
Choi et al., Effect of udenafil on portal venous pressure and hepatic fibrosis in rats. A novel therapeutic option for portal hypertension. Arzneimittelforschung, 2009, 59(12):641-6.
(Continued)

*Primary Examiner* — Sarah Pihonak
*Assistant Examiner* — Mikhail O'Donnel Robinson
(74) *Attorney, Agent, or Firm* — Finnegan, Henderson, Farabow, Garrett & Dunner, LLP

(57) ABSTRACT

Various methods and compositions for treating single ventricle heart disease (SVHD) patients, including patients who have undergone Fontan surgery and who have Fontan circulation (Fontan patient), to improve exercise performance, single ventricular performance, cardiac output and myocardial performance index (MPI) in the SVHD patients, including the Fontan patients, using udenafil compositions.

In one exemplary embodiment, the methods of the present invention include administering an effective amount of udenafil or a pharmaceutically acceptable salt thereof to a SVHD patient, including a Fontan, to improve the ventricular performance of the SVHD patient's, including the Fontan patient's, single functioning ventricle.

In another exemplary embodiment, the methods of the present invention include administering an effective amount of udenafil or a pharmaceutically acceptable salt thereof to a SVHD patient, including a Fontan patient, to improve the SVHD patient's, including the Fontan patient's, MPI.

In still another exemplary embodiment, the methods of the present invention include administering an effective amount of udenafil or a pharmaceutically acceptable salt thereof to a SVHD patient, including a Fontan patient, to improve the SVHD patient's, including the Fontan patient's, cardiac output.

In yet another exemplary embodiment, the methods of the present invention include administering an effective amount of udenafil or a pharmaceutically acceptable salt thereof to a SVHD patient, including a Fontan patient, who is about 6 years of age or older, to improve at least one or more or all of the following in the SVHD patient, including the Fontan patient: (a) ventricular performance of the SVHD patient's, including a Fontan patient's, single functioning ventricle as measured by MPI; (b) exercise capacity as measured by oxygen consumption at anaerobic threshold (VAT); (c) exercise capacity as measured by oxygen consumption at maximal effort or max $VO_2$; (d) work rate at VAT; (e) $VE/VCO_2$ at VAT; diastolic blood pressure at rest; and (g) oxygen saturation (%) at rest.

13 Claims, 11 Drawing Sheets

Related U.S. Application Data filed on Nov. 16, 2019, provisional application No. 62/905,350, filed on Sep. 24, 2019.

(51) Int. Cl.
| | |
|---|---|
| *A61K 9/28* | (2006.01) |
| *A61P 43/00* | (2006.01) |

(52) U.S. Cl.
CPC .......... *A61K 9/2018* (2013.01); *A61K 9/2054* (2013.01); *A61K 9/2059* (2013.01); *A61K 9/284* (2013.01); *A61P 43/00* (2018.01)

(56) References Cited

U.S. PATENT DOCUMENTS

| | | |
|---|---|---|
| 2005/0272741 A1 | 12/2005 | Rychik et al. |
| 2008/0021368 A1 | 1/2008 | Dasi et al. |
| 2011/0250279 A1 | 10/2011 | Yoo et al. |
| 2011/0306762 A1 | 12/2011 | Lee et al. |
| 2018/0169103 A1 | 6/2018 | Yeager et al. |
| 2019/0030037 A1 | 1/2019 | Yeager et al. |
| 2019/0030038 A1 | 1/2019 | Yeager et al. |
| 2023/0095034 A1 | 3/2023 | Yeager et al. |

FOREIGN PATENT DOCUMENTS

| | | |
|---|---|---|
| EC | SP088441 A | 6/2008 |
| JP | 2012-197274 A | 3/2012 |
| JP | 2013-514995 A | 5/2013 |
| JP | 2013-523809 A | 6/2013 |
| JP | 2010-532319 A | 10/2017 |
| KR | 100792126 B1 | 1/2008 |
| KR | 20070099363 A | 1/2008 |
| KR | 1020130086771 A1 | 8/2013 |
| KR | 101383430 A1 | 4/2014 |
| RU | 2420289 C1 | 6/2011 |
| WO | WO 2006/132460 A1 | 12/2006 |
| WO | WO-0002/7848 A1 | 5/2008 |
| WO | WO-2014078459 A1 | 5/2014 |

OTHER PUBLICATIONS

Ciliberti P et al., Modulation of pulmonary vascular resistance as a target for therapeutic interventions in fontan patients: focus on phosphodiesterase inhibitors, Future Cardiol, 2012, 8(2):271-284.

Giardini A et al., Effect of sildenafil on haemodynamic response to exercise and exercise capacity in fontan patients, Eur Heart J, 2008, 29(13):1681-1687.

Goldberg DJ et al., Impact of oral sildenafil on exercise performance in children and young adults after the fontan operation: a randomized, double-blind, placebo-controlled, crossover trial, Circulation, 2011, 123(11):1185-1193.

Goldberg DJ et al., Results of a phase I/II multi-center investigation of udenafil in adolescents after fontan palliation, Am Heart J, 2018, 188:42-52.

Goldberg DJ et al., Results of the Fontan Udenafil Exercise Longitudinal (FUEL) Trial, Circulation, 2020 (34 pages).

Goldberg DJ et al., Sildenafil improves ventricular performance in children and young adults after the fontan operation, Circulation, 2009, 120:S603.

Kim A, et al. Population pharmacokinetic analysis to recommend the optimal dose of udenafil in patients with mild and moderate hepatic impairment, Br J Clin Pharmacol, 2016, 82(2): 389-398.

Kim HL et al., Therapeutic effects of udenafil on pressure-overload cardiac hypertrophy, Hypertens Res, 2015, 38(9):597-604.

Kim K et al., PDE 5 inhibition with udenafil improves left ventricular systolic/diastolic function and exercise capacity in patients with chronic systolic heart failure: a 12-week randomized, double-blind, placebo-controlled trial (udenafil therapy to improve symptomatology, exercise tolerance and hemodynamics in patients with chronic systolic heart failure) (ULTIMATE-SHF), J Heart Lung Transplant, 2015, 34(45):S156.

Kim KH et al., Udenafil improves exercise capacity and left ventricular remodeling in patients with systolic heart failure, JACC, 2014, 63(12): A535.

Lichtinghagen R et al. The Enhanced Liver Fibrosis (ELF) score: normal values, influence factors and proposed cut-off values, J Hepatol, 2013, 59(2):236-42.

Mullard A, Parsing clinical success rate, *Nat Rev Drug Discov*, 2016, 15:447.

Paridon SM et al., A cross-sectional study of exercise performance during the first 2 decades of life after the Fontan operation, JACC, 2008, 52(2):99-107.

Park JS et al., Udenafil improves exercise capacity in patients with chronic obstructive pulmonary disease: a prospective study, COPD, 2012, 9(5):499-504.

Shabanian R et al., Sildenafil and ventriculo-arterial coupling in fontan-palliated patients: a noninvasive echocardiographic assessment, Pediatr Cardiol, 2013, 34:129-134.

AHA names top heart disease and stroke research advances of 2019, American Heart Association, dated: Dec. 13, 2019, 5 pages.

Akagi et al., "Influence of ventricular morphology on diastolic filling performance in double-inlet ventricle after the Fontan procedure", J. Am. Coll. Cardiol., Dec. 1993, vol. 22, No. 7, pp. 1948-1952.

Albouaini, K et al., "Cardiopulmonary exercise testing and its application", Heart, vol. 93, No. 10, (2007), pp. 1285-1292.

Amrhein et al., "Scientists rise up against statistical significance", Nature, Mar. 2019, vol. 567, No. 7748, pp. 305-307.

Andersen et al., "Sildenafil and diastolic dysfunction after acute myocardial infarction trial: rationale and design", Clin. Cardiol., Apr. 2013, vol. 36, No. 4, pp. 85-98.

Anderson et al., "Contemporary outcomes after the Fontan procedure: a Pediatric Heart Network multicenter study", J. Am. Coll., Jul. 8, 2008, vol. 52, No. 2, pp. 85-98.

Argiento et al., "Exercise stress echocardiography for the study of the pulmonary circulation", Eur. Respir J., Jun. 2010, vol. 35, No. 6, pp. 1273-1278.

Attina et al., "Phosphodiesterase type 5 inhibition reverses impaired forearm exercise-induced vasodilation in hypertensive patients", J. Hypertens, Mar. 2008, vol. 26, No. 3, pp. 501-507.

Australian Examination Report mailed Feb. 21, 2018, for Australian Patent Application No. 201502271, 4 pages.

Australian Notice of Acceptance for Patent Application No. 201502271 dated Feb. 19, 2019, 4 pages.

Avitabile et al., "A multifaceted approach to the management of plastic bronchitis after cavopulmonary palliation", Ann. Thorac. Surg., Aug. 2014, vol. 98, No. 2, pp. 634-640.

Barst et al., "STARTS-2 Investigators. STARTS-2: long-term survival with oral sildenafil monotherapy in treatment-naïve pediatric pulmonary arterial hypertension", Circulation, May 13, 2014, vol. 129, No. 19, pp. 1914-1923.

Behling et al., "Effect of 5-phosphodiesterase four-week long inhibition with sildenafil in patients with chronic heart failure: a double-blind, placebo-controlled clinical trial", J. Card. Fail., (Apr. 2008), vol. 14, No. 3, pp. 189-197.

Bialkowski et al., [Successful chronic treatment with sildenafil in a patient with end-stage heart failure following Fontan procedure], Kardiol. Pol., (vol. 69, No. 3, (2011), pp. 302-304., Polish., [English Abstract].

Binotto et al., "Altered endothelial function following the Fontan procedure", Cardiol. Young, Feb. 2008, vol. 18, No. 1, pp. 70-74.

Blum et al., "Treating heart failure with sildenafil", Congest Heart Fail., Jul.-Aug. 2009, vol. 15, No. 4, pp. 181-185.

Boolell et al., Sildenafil: an orally active type 5 cyclic GMP-specific phosphodiesterase inhibitor for the treatment of penile erectile dysfunction, Int'l. J. Impot. Res., vol. 8, No. 47, (1996), [Abstract].

Canadian Office Action for Application No. 2,954,183, dated Apr. 27, 2018, 4 pages.

Canadian Office Action for Application No. 2,954,183, dated Feb. 4, 2019, 3 pages.

Canter et al., "Indications for heart transplantation in pediatric disease: a scientific statement from the American Heart Association Council on Cardiovascular Disease in the Young; the Council on Clinical Cardiology, Cardiovascular Nursing, and Cardiovascular

(56)　　　　　References Cited

OTHER PUBLICATIONS

Surgery and Anesthesia; and the Quality of Care and Outcomes Research Interdisciplinary Working Group", Circulation, Feb. 6, 2007, vol. 115, No. 5, pp. 658-676.

Center for Drug Evaluation and Research, Application No. 203109Orig1s000, Summary Review, dated: 2012, 19 pages.

Cheung et al., "Serial assessment of left ventricular diastolic function after Fontan procedure", Heart, Apr. 2000, vol. 83, No. 4, pp. 420-424.

Chilean Office Action for Application No. 201700329 dated May 17, 2018, 8 pages. [Original].

Chilean Office Action for Application No. 201700329 dated May 17, 2018, 8 pages. [English Translation].

Chilean Office Action for Application No. 201700329 dated May 27, 2018, 10 pages. [Original].

Chilean Office Action for Application No. 201700329 dated May 27, 2018, 8 pages. [English Translation].

Chinese Office Action for Application No. 201580040518.0, dated Feb. 19, 2019, 15 pages. [English Translation].

Chinese Office Action for Application No. 201580040518.0, dated Feb. 19, 2019, 10 pages. [Original].

Chinese Office Action for Application No. 201580040518.0, dated Nov. 25, 2019, 15 pages. [English Translation].

Chinese Office Action for Application No. 201580040518.0, dated Nov. 25, 2019, 3 pages. [Original].

Chinese Office Action for Application No. 2024101406105, dated Jan. 4, 2025, 29 pages. [Original].

Chinese Office Action for Application No. 2024101406105, dated Jan. 4, 2025, 5 pages. [English Translation].

Choi et al., "Effect of udenafil on portal venous pressure and hepatic fibrosis in rats. A novel therapeutic option for portal hypertension.", Arzneimittelforschung, 2009, vol. 59 No. 12, pp. 641-646.

Ciliberti, et al., "Modulation of pulmonary vascular resistance as a target for therapeutic intervention in Fontan patients: focus on phosphodiesterase inhibitors", Future Cardiol., Mar. 2012, vol. 8, No. 2, pp. 271-284.

Ciliberti, et al., "Impact of Oral Chronic Administration of Sildenafil in Children and Young Adults after the Fontan Operation", Future Cardiol., Sep. 2011, vol. 7, No. 5, pp. 609-612.

ClinicalTrials.gov—"Effect of Tadalafil on Exercise Capacity in Pediatric Fontan Patients", NCT01291069, Feb. 4, 2011, <https://clinicaltrials.gov/ct2/show/NCT01291069>.

ClinicalTrials.gov—"Pharmacokinetics/Pharmacodynamic Study of Udenafli in Adolescents", NCT02201342, Jul. 24, 2014, <https://clinicaltrials.gov/ct2/show/NCT02201342?term=udenafil+and+fontan@rank=2>.

ClinicalTrials.gov—A Service of the U.S. National Institutes of Health, Pharmacokinetic/Pharmacodynamic Study of Udenafil in Adolescents, Jul. 21, 2016, 4 pages.

ClinicalTrials.gov—A Service of the U.S. National Institutes of Health, Fontan Udenafil Exercise Longitudinal Assessment Trial (FUEL), Jul. 21, 2016, 4 pages.

ClinicalTrials.gov—A Service of the U.S. National Institutes of Health, Pharmacokinetic/Pharmacodynamic Study of Udenafil in Adolescents, Apr. 10, 2015, 4 pages.

ClinicalTrials.gov—A Service of the U.S. National Institutes of Health, Changes to NCT02201342, Apr. 26, 2015, 3 pages.

ClinicalTrials.gov archive—View of NCT02201342 on Jul. 25, 2014, available at https://clinicaltrials.gov/ct2/history/NCT02201342/2014_07_25, accessed on Feb. 19, 2018.

ClinicalTrials.gov archive—History of Changes for Study: NCT02201342 available at https://clinicaltrials.gov/ct2/keyates/NCT02201342?A=1&B=2&C=merged#StudyPageTop, accessed on Sep. 14, 2018.

ClinicalTrials.gov—Key Record Dates, available at https://clinicaltrials.gov/ct2/history/NCT02201342, accessed on Sep. 14, 2018.

Colombia Office Action for Application No. NC2017/0000271 [English Translation].

Colombia Office Action for Application No. NC2017/0000271 [Original].

Colombia Office Action for Application No. NC2017/0000271, dated Apr. 4, 2019, [English Translation].

Colombia Office Action for Application No. NC2017/0000271, dated Apr. 4, 2019, [Original].

Colombian Office Action mailed Mar. 5, 2018, for Colombian Patent Application No. NC2017/0000271, 4 pages. [Original].

Colombian Office Action mailed Mar. 5, 2018, for Colombian Patent Application No. NC2017/0000271, 4 pages. [English Translation].

Colombian Office Action for Application No. NC2017/0000271, dated Oct. 4, 2018, 6 pages. [Original].

Colombian Office Action for Application No. NC2017/0000271, dated Oct. 4, 2018, 6 pages. [English Translation].

Company Report, Mezzion (140410), (dated Apr. 23, 2013, available at http://cfile30.uf.tistory.com/attach/273A264E517619D80E3D0D, accessed on May 27, 2016).

Deal et al., "Management of the failing Fontan Circulation", Heart, Jul. 2012, vol. 98, No. 4, pp. 1098-1104.

Diller et al., "Exercise intolerance in adult congenital heart disease; comparative severity, correlates, and prognostic implication", Circulation, Aug. 9, 2005, vol. 112, No. 6, pp. 828-835.

Diller et al., "Predictors of morbidity and mortality in contemporary Fontan patients; results from a multicenter study including cardiopulmonary exercise testing in 321 patients", Eur. Heart. J., Dec. 2010, vol. 31, No. 24, pp. 3073-3083.

Dominican Republic Office Action for Application No. P2017-0014, dated Jan. 23, 2019, 3 pages. [Original].

Dominican Republic Office Action for Application No. P2017-0014, dated Jan. 23, 2019, 6 pages. [English Translation].

D'Udekem et al., "How good is a good Fontan? Quality of life and exercise capacity of Fontans without Arrhythmias", Ann Thorac Surg., Dec. 2009, vol. 88, No. 6, pp. 1961-1969.

Ecuador Opposition Notice for Patent Application No. IEPI 2017-15154 dated Nov. 30, 2018, 12 pages. [Original].

Ecuador Opposition Notice for Patent Application No. IEPI 2017-15154 dated Nov. 30, 2018, 12 pages. [English Translation].

Ellis, S., "Mezzion's PDE5 inhibitor enters U.S. trials for Fontan patients", BioWorld, Jan. 22, 2014, <http:www.bioworld.com/content/mezzion%E2%80%99s-pde5-inhibitor-enters-us-trials-fontan-patients>.

Eurasian Office Action for Application No. 201692518/28 May 4, 2018, 2 pages. [English Translation].

Eurasian Office Action for Application No. 201692518/28 May 4, 2018, 2 pages. [Original].

Eurasian Office Action and Search Report for Application No. 201692518 dated Jul. 20, 2017 [English Translation].

Eurasian Office Action and Search Report for Application No. 201692518 dated Jul. 20, 2017 [Original].

European Search Report mailed Jan. 4, 2018, for European Patent Application No. 15831606.7, filed Jun. 30, 2015, 12 pages.

European Office Action for Patent Application No. 15831606.7, dated Apr. 26, 2019, 6 pages.

European Office Action for Patent Application No. 20869034.7, dated Sep. 17, 2025, 6 pages.

European Search Opinion for EP Application No. 23212824.9, dated May 24, 2024, 9 pages.

"Evaluation of Fontan-Associated Liver Disease", URL: https://clinicaltrials.gov/ct2/show/record/NCT03430583, date accessed: Sep. 25, 2024, 7 pages.

Extended European Search Report for EP Application No. 23212824.9 dated May 24, 2024, 19 pages.

Exhibit a-1 to Declaration of James L. Yeager and Won Geun Kim Under 37 CFR Section 1.130, dated Jul. 30, 2017 (referred to herein as "Declaration"): Email from ClinicalTrials.gov to James L. Yeager confirming receipt of Mezzion's Protocol Record PHN-Udenafil-01, Pharmacokinetic/Pharmacodynamic Study of Udenafil in Adolescents submitted by James L. Yeager on behalf of Mezzion (Jul. 25, 2014).

Exhibit b-1 to Declaration: Press release entitled "Mezzion Pharma Announces Collaboration with New England Research Institutes to Evaluate Udenafil in Adolescents with Single Ventricles Heart Defects" (Jan. 10, 2014).

(56) References Cited

OTHER PUBLICATIONS

Exhibit b-2 to Declaration: Email from PR Newswire to James L. Yeager, dated Jan. 9, 2014.

Exhibit b-3 to Declaration: Email from PR Newswire to James L. Yeager, dated Jan. 9, 2014.

Exhibit c-1 to Declaration: Email from Youn-Taek Song (IR Team/Manager for Mezzion Pharma) to Minha Choi of Korean Investment regarding Exhibit c-2, the "Company Report, Mezzion (140410)" (Aug. 13, 2013).

Exhibit c-2 to Declaration: Mezzion report entitled "Company Report, Mezzion (140410)" (Aug. 13, 2023).

Exhibit c-3 to Declaration: Mezzion report entitled "Mezzion Inventor Relations" (Jul. 2013). [Original].

Exhibit c-3 to Declaration: Mezzion report entitled "Mezzion Inventor Relations" (Jul. 2013) [English Translation].

Exhibit c-4 to Declaration: Mezzion report entitled "Mezzion Investor Relations" (Jun. 2014).

Exhibit h-1 to Declaration: Email from PR Newswire confirming receipt of the content of Exhibit h-2 submitted by James L. Yeager, on behalf of Mezzion (Oct. 9, 2014).

Exhibit i-1 to Declaration: Email from Youn-Taek Song (IR Team/Manager for Mezzion Pharma) to Sae-Bom Lee of Maeil Business Newspaper. Exhibit i-1 was submitted with four attachments, i.e., (1) Exhibit i-2, Jan. 9, 2014, (2) Exhibit i-3, Jan. 2012, (3) Exhibit i-4, Jul. 23, 2012, and (4) Exhibit i-5, May 16, 2012, attached thereto. Exhibit i-1 is provided in Korean with English translation (Jan. 10, 2014).

Exhibit i-2 to Declaration: Press release entitled "Zydena in the United States acquired the patent applications for the enlarged Benign prostatic hyperplasia treatment effect", (Jan. 9, 2014).

Exhibit i-3 to Declaration: "Dong-A Pharmatech IR report", (Jan. 2012).

Exhibit i-3 to Declaration: "Dong-A Pharmatech IR report", (Jan. 2012). [English Translation].

Exhibit i-4 to Declaration: Press release entitled "Zydena, Approved by the Ethics Committee in Mexico", (Jul. 23, 2012).

Exhibit i-5 to Declaration: Press release entitled "Dong-A Pharmtech, Russian Market Second development export after 2007", (May 16, 2012).

Exhibit j-1 to Declaration: Email from Youn-Taek Song (IR Team/Manager for Mezzion Pharma) to reporter Dong In Lee of Maeil Business Newspaper. Attached to Exhibit j-1 is Exhibit j-2, a press release (Mar. 31, 2015).

Exhibit j-2 to Declaration: Press release entitled "Mezzion, return exclusive rights (develop and marketing) to erectile dysfunction and Benign prostatic hyperplasia in the Americas" (Mar. 31, 2015).

Exhibit k-1 to Declaration: Email from Youn-Taek Song (IR Team / Manager for Mezzion Pharma) to reporter YooJin Jo of Asia Business Daily. Attached to Exhibit k-1 are Exhibits k-2, K-3 and K-4 (Jun. 20, 2015).

Exhibit k-2 to Declaration: Press release entitled Mezzion, completes to ½ Clinical Trials of Udenafil in Fontan patients (Mar. 16, 2015).

Exhibit k-3 to Declaration: Press release entitled "Mezzion Pharma Announces Collaboration with New England Research Institutes to Evaluate Udenafil in Adolescents with Fontan Surgery", (Jan. 10, 2014).

Exhibit k-4 to Declaration: Press release entitled "Mezzion, submit uses patent application for Fontan Operation", (Jun. 29, 2015).

Exhibit I to Declaration: Correspondence to reporter Hyoung-Su Park of Edaily by Youn-Tack Song (IR Team/Manager for Mezzion Pharma) on behalf of Mezzion by e-mail on Mar. 26, 2014 for the purpose of an analyst report [Korean Original followed by English Translation].

Exhibit m to Declaration: Correspondence regarding company presentation submitted to analysts by Youn-Tek Song (IR Team/Manager for Mezzion Pharma) on behalf of Mezzion by e-mail on Mar. 26, 2014 for the purpose of an Analyst Conference Call [Korean Original followed by English Translation].

Exhibit A to Jun. 22, 2018 Response: Karkoswsky, Abraham. "Summary Review: NDA 203109 Sildenafil Citrated Powder for Reconstitution." Drugs@FDA: FDA Approved Drug Products, US Food & Drug Administration, Reference ID: 3131055. May 15, 2012, 20 pages., www.accessdata.fda.gov/drugs@fda_docs/nda/2012/203109Orig1s000SumR.pdf.

Exhibit B to Jun. 22, 2018 Response: "Labeling-Package Insert; NDA 203109 Sildenafil Citrated Powder for Reconstitution." Drugs@FDA: FDA Approved Drug Products, US Food & Drug Administration, Reference ID: 3471998. Mar. 11, 2014, 31 pages. www.accessdata.fda.gov/drugsatfda_docs/label/2014/021845s011,022473s004,0203109s002lbl.pdf.

Exhibit C to Jun. 22, 2018 Response: Sung, Hyun Hwan, and Sung Won Lee."Chronic Low Dosing of Phosphodiesterase Type 5 Inhibitor for Erectile Dysfunction", Korean Journal of Urology, vol. 53, No. 6, 2012, pp. 377-385, doi: 10.4111/kju.2012.53.377.

Exhibit D to Jun. 22, 2018 Response: Anderson, Page A.W., et al., "The Fontan Patient: Inconsistencies in Medication Therapy Across Seven Pediatric Heart Networks Centers." Pediatric Cardiology, vol. 31, No. 8, 2010, pp. 1219-1228. doi:10.1007/s00246-010-9807-5.

Fernandes et al., "Serial cardiopulmonary exercise testing in patients with previous Fontan surgery", Pediatr. Cardiol., Feb. 2010, vol. 31, No. 2, pp. 175-180.

Fontan et al., "Surgical repair of tricuspid atresia", Thorax, May 1971, vol. 26, No. 3, pp. 240-248.

"Fontan Circulation: success or failure?", Congenital Heart Defect Research Blog, Mar. 13, 2013, <http:bendantzer.wordpress.com/2013/03/13/fontan-circulation-success-or-failure/>.

Frommelt et al., "Doppler assessment of pulmonary artery flow patterns and ventricular function after the Fontan operation", A. J. Cardiol., Nov. 1991, vol. 68, No. 1, pp. 1211-1215.

Galie et al., "Sildenafil citrate therapy for pulmonary arterial hypertension", N. Engl. J. Med., Nov. 17, 2005, vol. 353, No. 20, pp. 2148-2157.

Galie et al., "Tadalafil therapy for pulmonary arterial hypertension", Circulation, Jun. 9, 2009, vol. 119, No. 22, pp. 2894-2903.

Gewilling, M. et al., "Failure of the Fontan Circulation", Heart Failure Clinics, vol. 10, No. 1, 2014, pp. 105-116. doi:10.1016/j.hfc.2013.09.010.

Gewilling et al., "The Fontan circulation; who controls cardiac output?", Interact. Cardiovasc. Thorac Surg., Mar. 2010, vol. 10, No. 3, pp. 428-433.

Gersony, W. M., "Fontan Operation After 3 Decades, What We Have Learned", Circulation, vol. 117, (2008), pp. 13-15.

Giardini, A. et al., "Effect of sildenafil on haelmodynamic response to exercise and exercise capacity in Fontan patients", Eur. Hearts J., vol. 29, No. 13, Jul. 2008, pp. 1681-1687.

Giardini, A. et al., "Usefulness of Cardiopulmonary Exercise to predict long-term prognosis in adults with repaired tetralogy of Fallot", Am J. Cardiology, (May 15, 2007, e-published Apr. 5, 2007), vol. 99, No. 10, pp. 1462-1467.

Giardini et al., "Natural history of exercise capacity after the Fontan operation; a longitudinal study", Ann. Thorac Surg., Mar. 2008, vol. 85, No. 3, pp. 818-821.

Giordano, et al., "First experience with sildenafil after Fontan operation; short-term outcomes", J. Cardiovasc. Med., (Hagerstown), vol. 16, No. 8, Aug. 2015, pp. 552-555.

Goldberg et al., "Fontan Circulation, The Search for Targeted Therapy", Circulation, vol. 130, (2014), pp. 1999-2001.

Goldberg et al., "Impact of sildenafil on echocardiographic indices of myocardial performance after the Fontan operation", Pediatr. Cardiol., vol. 33, No. 5, Jun. 2012, pp. 689-696.

Goldberg, D. J. et al. "Impact of Oral Sildenafil on Exercised Performance in Children and Young Adults After the Fontan Operation—A Randomized, Double-Blind, Placebo- Controlled, Crossover Trial", Circulation, vol. 123, (2011), pp. 1185-1193.

Goldberg et al., "Abstract 2161: Sildenafil Improves Ventricular Performance in Children and Young Adults After the Fontan Operation", Circulation, (2009), vol. 120, S603.

Goldberg et al., "Results of a phase I/II multi-center investigation of udenafil in adolescents after fontan palliation", Am. Heart J., Jun. 2017, vol. 188, pp. 42-52.

(56) References Cited

OTHER PUBLICATIONS

Goldberg et al., Design and rationale of the Fontan Udenafil Exercise Longitudinal (FUEL) trial, Am. Heart J., Apr. 2018, vol. 201, pp. 1-8.

Goldberg et al., Results of the Fontan Udenafil Exercise Longitudinal (FUEL) Trial, Circulation, 2020, 34 pages.

Goldberg, et al., "Exercise Capacity and Predictors of Performance After Fontan: Results from the Pediatric Heart Network Fontan 3 Study", Pediatric Cardiology, vol. 42, (2021), pp. 158-168.

Goldstein et al., "Relation of systemic venous return, pulmonary vascular resistance, and diastolic dysfunction to exercise capacity in patients with single ventricle receiving fontan palliation", Am. J. Cardiol., Apr. 15, 2010, vol. 105, No. 8, pp. 1169-1175.

Goldstein et al., "Usefulness of peripheral vascular function to predict functional health status in patients with Fontan circulation", Am. J. Cardiol., Aug. 1, 2011, vol. 108, No. 3, pp. 428-434.

Guazzi et al., "PDE5 Inhibition with sildenafil improves ventricular diastolic function, cardiac geometry, and clinical status in patients with stable systolic heart failure: results of a 1-year, prospective, randomized, placebo-controlled study", Circ. Heart Fail., Jan. 2011, vol. 4, No. 1, pp. 8-17.

Guazzi et al., "Pulmonary hypertension in heart failure with preserved ejection fraction: a target of phosphodiesterase-5 inhibition in a 1-year study", Circulation, Jul. 12, 2011, vol. 124, No. 2, pp. 164-174.

Gu Kang et al., "Udenafil: efficancy and tolerability in the management of erectile dysfunction", Ther. Adv. Urol., vol. 5, No. 2, (2013), pp. 101-110.

Haseyama et al., "Pulmonary vasodilation therapy with sildenafil citrate in a patient with plastic bronchitis after the Fontan procedure for hypoplastic left heart syndrome", J. Thorac. Cardiovasc. Surg., Nov. 2006, vol. 132, No. 5, pp. 1232-1233.

Hebert, A. et al., "Bosentan Improves Exercise Capacity in Adolescents and Adults After Fontan Operation: The TEMPO (Treatment With Endothelin Receptor Antagonist in Fontan Patients, a Radomized, Placebo-Controlled, Double-Blind Study Measuring Peak Oxygen Conspumption) Study." Circulation, vol. 130, No. 23, 2014, pp. 2021-2030. doi: 10.1161/circulationaha.113.008441.

Highlights of Prescribing Information for REVATIO, Pfizer, 2014, 30 pages.

Hosein, et al., "Factors influencing early and late outcome following the Fontan procedure in the current era. The 'Two Commandants'?", Eur. J. Cardiothorac. Surg., Mar. 2007, vol. 31, No. 3, pp. 344-353.

Huddleston et al., "Sildenafil for the treatment of pulmonary hypertension in pediatric patients", Pediatr. Cardiol., Oct. 2009, vol. 30, No. 7, pp. 871-872.

Humpl et al., "Beneficial effect of oral sildenafil therapy on childhood pulmonary arterial hypertension: twelve-month clinical trial of a single-drug, open-label, pilot study", Circulation, Jun. 21, 2005, vol. 111, No. 24, pp. 3274-3280.

Inai et al., "Skeletal muscle hemodynamics and endothelial function in patients after Fontan operation", A. J. Cardiol., Mar. 2004, vol. 93, No. 6, pp. 792-797.

International Preliminary Report on Patentability for International Application No. PCT/US2022/040227, dated Feb. 13, 2024, 6 pages.

Japanese Notification of Reasons for Refusal mailed Mar. 6, 2018, for Japanese Patent Application No. 2017-504434, 4 pages. [Original].

Japanese Notification of Reasons for Refusal mailed Mar. 6, 2018, for Japanese Patent Application No. 2017-504434, 4 pages. [English Translation].

Japanese Decision of Final Refusal for Application No. 2017-504434, dated Oct. 2, 2018, 14 pages. [Original].

Japanese Decision of Final Refusal for Application No. 2017-504434, dated Oct. 2, 2018, 14 pages. [English Translation].

Japanese Notice of Reasons for Refusal for Japanese Patent Application No. 2024-214477, dated Mar. 25, 2025, 5 pages. [Original].

Japanese Notice of Reasons for Refusal for Japanese Patent Application No. 2024-214477, dated Mar. 25, 2025, 5 pages. [English translation].

Jenkins et al., "Decreased exercise performance with age in children with hypoplastic left heart syndrome", J. Pediatr., Apr. 2008, vol. 152, No. 4, pp. 507-512.

Jin et al., "Impaired vascular function in patients with Fontan circulation", Int. J. Cardiol., Aug. 21, 2007, vol. 120, No. 2, pp. 221-226.

Kaneko et al., "Single right ventricles have impaired systolic and diastolic function compared to those of left ventricular morphology", J. Am. Soc. Echocardiogr., Nov. 2012, vol. 25, No. 11, pp. 1222-1230.

Keteyian et al., "Reproducibility of peak oxygen uptake and other cardiopulmonary exercise parameters: implications for clinical trials and clinical practice", Chest, Oct. 2010, vol. 138, No. 4, pp. 950-955.

Kim et al., "ULTIMATE-SHF trial (Udenafil Therapy to Improve symptomatology, exercise Tolerance and hemodynamics in patients with chronic systolic heart failure): study protocol for a randomized, placebo-controlled, double-blind trial", Trials, Jun. 22, 2013, vol. 14, No. 188.

Kim et al., "DA-8159: Erectrogenic. Drugs of the Future", (2005), vol. 30, No. 7, pp. 678-682.

Kim, K. H. et al., "Udenafil Improves Exercise Capacity and Left Ventricular Remodeling in Patients with Systolic Heart Failure", J. American College of Cardiology, Apr. 1, 2014, vol. 63, Issue 12, 1 page.

Kim, K. H. et al., "Therapeutic Effects of Udenafil on Pressure-Overload Cardiac Hypertrophy", Hypertens Res, (Sep. 2015, e-published Apr. 2, 2015), vol. 38, Issue 9, pp. 597-604.

Kim, K. et al., "PDE 5 Inhibition with Udenafil Improves Left Ventricular Systolic/Diastolic Function and Exercise Capacity in Patients with Chronic Systolic Heart Failure: A 12-Week, Randomized, Double-Blind, Placebo-Controlled Trial (Udenafil Therapy to Improve Symptomatology, Exercise Tolerance and Hemodynamics in Patients with Chronic Systolic Heart Failure)", The Journal of Heart and Lung Transplantation, Apr. 15, 2015, vol. 34, No. 4, S156.

Kim et al., "Mezzion Pharma Announces Collaboration with New England Research Institutes to Evaluate Udenafil Adolescents with Single Ventricle Heart Defects", Jan. 10, 2014, 2 pages.

Kim et al., "Safety, tolerability and pharmacokinetics of udenafil, a novel PDE-5 inhibitor, in healthy young Korean subjects", Br. J. Clin. Pharmacol., Jun. 2008, vol. 65, No. 6, pp. 848-854.

Kim et al. "Population pharmacokinetic analysis to recommend the optimal dose of udenafil in patients with mild and moderate hepatic impairment", Br J Clin Pharmacol, 2016, vol. 82, No. 2, pp. 389-398.

Korean Office Action for Application No. 10-2017-7006695, dated Sep. 18, 2018, 3 pages. [Original].

Korean Office Action for Application No. 10-2017-7006695, dated Sep. 18, 2018, 3 pages. [English Translation].

Kouvelas, D. et al., "PDE5 Inhibitors: In Vitro and In Vivo Pharmacological Profile", Current Pharmaceutical Design, vol. 15, No. 30, (2009), pp. 3464-3475. doi: 10.2174/138161209789206971.

Kruger et al., "Protein kinase G modulates human myocardial passive stiffness by phosphorylation of the titin springs", Circ. Res. Jan. 2, 2009, vol. 104, No. 1, pp. 87-94.

La Gerche et al., "What Limits Cardiac Performance during Exercise in Normal Subjects and in Healthy Fontan Patients?", Int. J. Pediatr., 2010.

Lichtinghagen et al. "The Enhanced Liver Fibrosis (ELF) score: normal values, influence factors and proposed cut-off values", J Hepatol, 2013, vol. 59, No. 2, pp. 236-242.

Machine translation of "Company Report, Mezzion (140410)", (dated Apr. 23, 2013, available at http://cfile30uf.tistory.com/attach/273A264E517619D80E3D0D, accessed on May 27, 2016).

Mahle et al., "Endothelial Function following the Fontan operation", Am. J. Cardiol., May 15, 2003, vol. 91, No. 10, pp. 1286-1288.

Manlhiot et al., "Functional Health status of adolescents after the Fontan procedure—comparison with their siblings", Can. J. Cardiol., Sep. 2009, vol. 25, No. 9, e294-300.

(56)     References Cited

OTHER PUBLICATIONS

Martin et al., "The Challenge of Patient Adherence", Ther. Clin. Risk Manag., vol. 1, No. 3, (2005), pp. 189-199.

Mccrindle et al., "Laboratory measures of exercise capacity and ventricular characteristics and function are weakly associated with functional health status after Fontan procedure", Circulation, Jan. 5, 2010, vol. 121, No. 1, pp. 34-42.

Mccrindle et al., "Relationship of patient and medical characteristics to health status in children and adolescents after the Fontan procedure", Circulation, Feb. 28, 2006, vol. 113, No. 8, pp. 1123-1129.

Meadows et al., "Fontan Fenestration Closure Has No Acute Effect on Exercise Capacity but Improves Ventilatory Response to Exercise", J. Am. Coll. Cardiol., 2008, vol. 52, No. 2, pp. 108-113.

Menon et al., "Single-Ventricle Cardiology: Palliation, Care and Resource Utilization", Circulation, vol. 128, A1064, (2013), 2 pages. [Abstract].

Menon, S.C. et al., "Effect of Tadalafil on Exercise Parameters in Young Fontan Patients", Circulation, vol. 128: A16024 (2013), Abstract.

Mezzion, "Global C&D business to post tangible results", Aug. 13, 2013.

"Mezzion Pharma Initiates Clinical Development Program to Evaluate Udenafil in Adolescents with Single Ventricle Heart Defects", MedIndia. Jul. 23, 2024, <http://www.,medindia.net/health-press-release/Mezzion-Pharma-Initiates-Clinical-Development-Program-to-Evaluate-Udenafil-In-Adolescents-With-Single-Ventricle-Heart-Defects-216437-1.htm>/.

"Mezzion Pharma Initiates Clinical Development Program to Evaluate Udenafil in Adolescents with Single Ventricle Heart Defects", Jul. 23, 2024, <http://www.prnewswire.com/news-releases/mezzion-pharma-Initiates-clinical-development-program-to-evaluate-udenafil-in-adolescents-with-single-ventricle-heart-defects-268268072.html>.

"Mezzion Pharma Announces Collaboration With New England Research Institutes to Evaluate Udenafil in Adolescents With Single Ventricle Heart Defects", PR Newswire, Jan. 10, 2014, <http://www.prnewswire.com/news-releases/mezzion-pharma-announces-collaboration-with-new-england-institutes-to-evaluate-udenafil-in-adolescents-with-single-ventricle-heart-defects-239603121.html>.

Morchi et al., "Sildenafil Increases Systemic Saturation and Reduces Pulmonary Artery Pressure in Patients with Failing Fontan Physiology", Congenit. Heart Dis., vol. 4, No. 2, Apr. 2009, pp. 107-111.

Mori, H et al., "Sildenafil Reduces Pulmonary Vascular Resistance in Patients with Single Ventricular Physiology", (Nov. 26, 2013), Circulation, vol. 128, (Suppl. 22): A16117.

Moroccan Office Action for Application No. 40095 dated Aug. 9, 2017 [English Translation].

Moroccan Office Action for Application No. 40095 dated Aug. 9, 2017 [Original].

Mourani et al., "Effects of long-term sildenafil treatment for pulmonary hypertension in infants with chronic lung disease", J. Pediatr., Mar. 2009, vol. 154, No. 3, e379-384. e2.

Nagayama et al., "Sildenafil stops progressive chamber, cellular, and molecular remodeling and improves calcium handling and function in hearts with pre-existing advanced hypertrophy caused by pressure overload", J. Am. Coll. Cardiol., Jan. 13, 2000, vol. 53, No. 2, pp. 207-215.

Navaratnam et al., "Exercise-Induced Systemic Venous Hypertension in the Fontan Circulation", Am J Cardiol., 2016, vol. 117, No. 10, 1667-1671.

*Nelson* v. *Bowler*, 626 F.2d 853 (C.C.P.A. 1980).

New Zealand Further Examination Report for Application No. 727653 dated Aug. 10, 2018, 3 pages.

New Zealand Further Examination Report for Application No. 727653 dated Apr. 24, 2018, 7 pages.

New Zealand Office Action for Application No. 727653 dated Aug. 24, 2017, 7 pages.

Ono et al., "Clinical outcome of patients 20 years after Fontan operation—effect of fenestration on late morbidity", Eur. J. Cardiothorac Surg., Dec. 2006, vol. 30, No. 6, pp. 923-929.

Panamanian Office Action for Application No. 91474 dated Apr. 20, 2017. [English Translation].

Panamanian Office Action for Application No. 91474 dated Apr. 20, 2017. [Original].

Panamanian Office Action for Application No. 91474 dated Sep. 18, 2018, 6 pages [English Translation].

Panamanian Office Action for Application No. 91474 dated Sep. 18, 2018, 5 pages [Original].

Paridon et al., "A cross-sectional study of exercise performance during the first 2 decades of life after the Fontan operation", J. Am. Coll. Cardiol., Jul. 8, 2008, vol. 52, No. 2, pp. 99-107.

Park, J.S. et al., Udenafil Improves Exercise Capacity in Patients with Chronic Obstructive Pulmonary Disease: A Prospective Study, COPD: Journal of Chronic Obstructive Pulmonary Disease: 9.5, 499-504, (2012).

Pundi et al., "40-year Follow-Up After the Fontan Operation: Long-Term Outcomes of 1,052 Patients", J. Am. Coll. Cardiol., Oct. 13, 2015, vol. 66, No. 15, pp. 1700-1710.

Reinhardt et al., "Sildenafil in the management of the failing Fontan circulation", Cardiol. Younq, Oct. 2010, vol. 20, No. 5, pp. 522-525.

Rhodes, J. et al., "Effect of Inhaled Lloprost on the Exercise function of Fontan Patients: A Demonstration of Concept", International Journal of Cardiology, vol. 168, No. 3, (2013), pp. 2435-2440. doi:10.1016/j.ijcard.2013.03.014.

Rhodes et al., "Non-Geometric echocardiographic indices of ventricular function in patients with a Fontan circulation", J. Am. Soc. Echocardiogr., Nov. 2011, vol. 24, No. 11, pp. 1213-1219.

Rogers, L. S. et al., "18 Years of the Fontan Operation at a Single Institution, Journal of the American College of Cardiology", vol. 60, No. 11, (2012), pp. 1018-1025, doi: 10.1016/j.jacc.2012.05.010.

Rychik, J. et al., "Relentless Effects of the Fontan Paradox", Seminars in Thoracic and Cardiovascular Surgery, vol. 19, No. 1, (2016), pp. 37-43.

Rychik, J. et al., "Forty Years of the Fontan Operation: A Failed Strategy", Pediatric Cardiact Surgery Annual, (2010), pp. 96-100.

Sabri et al., "Effect of Tadalafil Myocardial and Endothelial Function and Exercise Performance After Modified Fontan Operation", Pediatr. Cardiol., vol. 37, (2016), pp. 55-61.

Sabri et al., "Comparison of the therapeutic and side effects of tadalafil and sildenafil in children and adolescents with pulmonary arterial hypertension", Pediatr. Cardiol., vol. 35, No. 4, (2014), pp. 699-704, [Abstract].

Sanghavi et al., "Determinants of exercise function following univentricular versus biventricular repair for; pulmonary atresia/intact ventricular septum", Am. J. Cardiol., Jun. 1, 2006, vol. 97, No. 11, pp. 1638-1643.

Sano et al., "Assessment of ventricular contractile state and function in patients with univentricular heart", Circulation, Jun. 1989, vol. 79, No. 6, pp. 1247-1256.

Santos et al., "Tadalafil-induced improvement in left ventricular diastolic function in resistant hypertension", Eur. J. Clin. Pharmacol., Feb. 2014, vol. 70, No. 2, pp. 147-154.

Saudi Arabia Examination Report for Application No. 517380879, dated Jan. 2, 2019, 2 pages. [Original].

Saudi Arabia Examination Report for Application No. 517380879, dated Jan. 2, 2019, 2 pages. [English Translation].

Schilling et al., "The Fontan epidemic: Population projections from the Australia and New Zealand Fontan Registry", Int. J. Cardiol., Sep. 15, 2016, vol. 219, pp. 14-19.

Schuuring, M. J. et al., "Impact of Bosentan on Exercise capacity in Adults after the Fontan Procedure: a randomized controlled trial", European Journal of Heart Failure, vol. 15, No. 6, (2013), pp. 690-698, doi:10.1093/eurjhf/hft017.

Shabanian, R. et al., "Sildenafil and ventriculoarterial coupling in Fontan-palliated patients: a noninasive echocardiography assessment", Pedatr. Cardiol, vol. 34, No. 1, (Jan. 2013, e-published Aug. 5, 2012), pp. 129-134.

Shon et al., "The disposition of three phosphodiesterase type 5 inhibitors, vardenafil, sildenalfil, and udenafil, is differently influ-

(56)          References Cited

OTHER PUBLICATIONS enced by the CYP3A5 genotype", Pharmacogenetics and Genomics, vol. 21, No. 12, (2011), pp. 820-828., doi:10.1097/fpc.0b013e32834b79e6.

Singapore Search Report and Written Opinion for Application No. 11201700060W dated Feb. 26, 2018, 9 pages.

Snarr et al., "Pulmonary vasodilator therapy in the failing Fontan circulation: rationale and efficacy", Cardiol. Young, Dec. 2015, vol. 25, No. 8, pp. 1489-1492.

Stickland et al., "Does fitness level modulate the cardiovascular hemodynamic response to exercise?", J. Appl. Physiol., Jun. 2006, vol. 100, No. 6, pp. 1895-1901.

Taiwanese Office Action for Application No. 104121758, dated Apr. 8, 2019, 5 pages. [Original].

Taiwanese Office Action for Application No. 104121758, dated Apr. 8, 2019, 7 pages. [English Translation].

Takimoto et al., "Chronic Inhibition of cyclic GMP phosphodiesterase 5A prevents and reverses cardiac hypertrophy", Nat. Med., Feb. 2005, vol. 11, No. 2, pp. 214-222.

Takimoto et al., "Compartmentalization of cardiac beta-adrenergic inotrophy modulation by phosphodiesterase type 5", Circulation, Apr. 24, 2007, vol. 115, No. 16, pp. 2159-2167.

Thacker et al., "Use of oral budesonide in the management of protein-losing enteropathy after the Fontan operation", Ann. Thorac. Surg., Mar. 2010, vol. 89, No. 3, pp. 837-842.

Trojnarska et al., "Challenges of management and therapy in patients with a functionally single ventricle after Fontan operation", Cardiol. J., 2011, vol. 18, No. 2, pp. 119-127.

"Trials will evaluate udenafil for heart defects in adolescents", Healio Cardiology Today, Feb. 1, 2014, <http://www.healio.com.cardiology/pediatric-cardiology/news/online/%7Bda00eddc-5a3e-4a27-80d6-05b12bb3acc4%7D/trials-will-evaluate-udenafil-for-heart-defects-in-adolescents>.

Tunisian Office Action for Application No. TN2017/0029 dated Sep. 27, 2017, [English Translation].

Tunisian Office Action for Application No. TN2017/0029 dated Sep. 27, 2017. [Original].

Tunks et al., "Sildenafil exposure and hemodynamic effect after Fontan surgery", Pediatr. Crit. Care Med., Jan. 2014, vol. 15, No. 1, pp. 28-34.

Ukranian Office Action mailed Jan. 16, 2018, for Ukranian Patent Application No. 2016 13574, 4 pages. [Original].

Ukranian Office Action mailed Jan. 16, 2018, for Ukranian Patent Application No. 2016 13574, 4 pages. [English Translation].

Ukrainian Notice of Decision to Grant for Patent Application No. a201613574, dated Feb. 15, 2019, 7 pages. [Original].

Ukrainian Notice of Decision to Grant for Patent Application No. a201613574, dated Feb. 15, 2019, 13 pages. [English Translation].

Uzun et al., "Resolution of protein-losing enteropathy and normalization of mesenteric Doppler flow with sildenafil after Fontan", Ann. Thrac. Surg., Dec. 2006, vol. 82, No. 6, e39-40.

Van De Bruaene et al., "Sildenafil improves exercise hemodynamics in Fontan patients"., Circ. Cardiovasc Imaging, Mar. 2014, vol. 7, No. 2, pp. 265-273.

Wasserman, E., "Mezzion Pharma Appoints Jefferson Gregory to Board of Directors", Fierce Biotech, Oct. 9, 2014, <http://www.fiercebiotech.com/biotech/mezzion-pharma-appoints-jefferson-gregory-to-board-of-directors>.

Written Opinion issued in related International Patent Application No. PCT/US2015/038638, dated Sep. 22, 2015.

Zarin et al., "The ClinicalTrials.gov results database—update and key issues", New England Journal of Medicine, Mar. 3, 2011, vol. 364, No. 9, pp. 52-60.

Zhao et al., "Efficacy and safety of once-daily dosing of udenafil in the treatment of erectile dysfunction: results of a multicenter, randomized, double-blind, placebo-controlled trial", Eur. J. of Urology, vol. 60, (2011), pp. 380-387. [Abstract].

Zou et al., "Status and Analysis of New Drugs in the World", First Edition, Press of the Second Military Medical University, Oct. 2010, p. 250. [Original].

Zou et al., "Status and Analysis of New Drugs in the World", First Edition, Press of the Second Military Medical University, Oct. 2010, p. 250. [English Translation].

* cited by examiner

HYPOPLASTIC LEFT HEART SYNDROME (HLHS)
STAGE 1 - NORWOOD

BLALOCK-TAUSSIG
SHUNT

HOMOGRAFT PATCH
(TO RECONSTRUCT AORTA)

SURGICALLY
ENLARGED
ATRIAL SEPTAL
DEFECT

HOMOGRAFT
PATCH ON PDA

LA

LV

RA

RV

⊘ OXYGEN-RICH BLOOD     AO: AORTA         PA: PULMONARY ARTERY
⊘ OXYGEN-POOR BLOOD    LA: LEFT ATRIUM   LV: LEFT VENTRICLE
⊘ MIXED BLOOD          RA: RIGHT ATRIUM  RV: RIGHT VENTRICLE

HYPOPLASTIC HEART SYNDROME (HLHS)
STAGE 2 - BIDIRECTIONAL GLENN

DIVIDED BLALOCK-TAUSSIG SHUNT

SUPERIOR VENA
CAVA ATTACHED
TO RIGHT PA

LEFT PA

LA

LV

RA

RV

⊘ OXYGEN-RICH BLOOD    AO: AORTA    PA: PULMONARY ARTERY
⊗ OXYGEN-POOR BLOOD    LA: LEFT ATRIUM    LV: LEFT VENTRICLE
⊛ MIXED BLOOD    RA: RIGHT ATRIUM    RV: RIGHT VENTRICLE

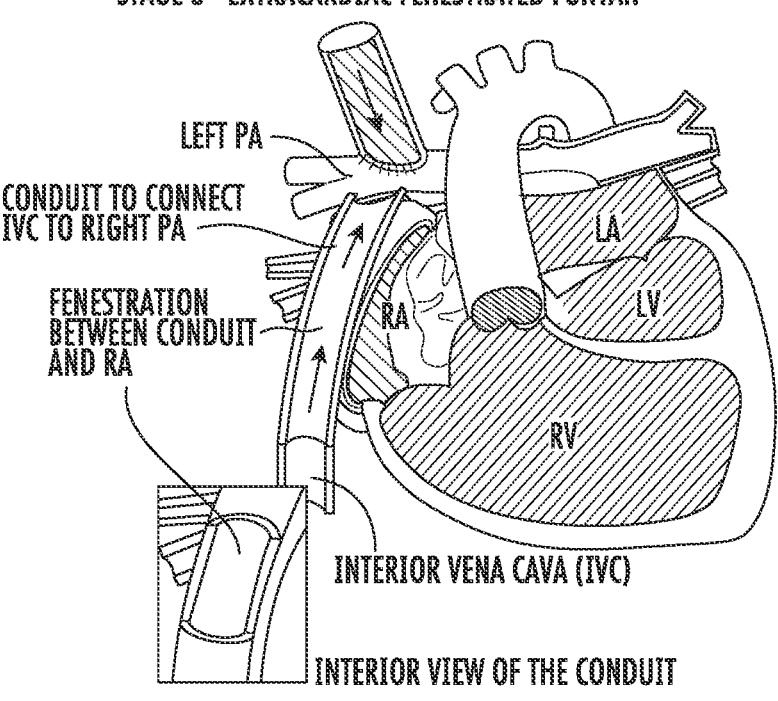

HYPOPLASTIC LEFT HEART SYNDROME (HLHS)
STAGE 3 ~ EXTRACARDIAC FENESTRATED FONTAN

LEFT PA

CONDUIT TO CONNECT
IVC TO RIGHT PA

FENESTRATION
BETWEEN CONDUIT
AND RA

RA

LA

LV

RV

INTERIOR VENA CAVA (IVC)

INTERIOR VIEW OF THE CONDUIT

OXYGEN-RICH BLOOD   AO: AORTA          PA: PULMONARY ARTERY
OXYGEN-POOR BLOOD   LA: LEFT ATRIUM    LV: LEFT VENTRICLE
MIXED BLOOD         RA: RIGHT ATRIUM   RV: RIGHT VENTRICLE

FIG. 7

METHODS AND COMPOSITIONS FOR IMPROVING EXERCISE PERFORMANCE, SINGLE VENTRICULAR PERFORMANCE, CARDIAC OUTPUT AND MYOCARDIAL PERFORMANCE INDEX (MPI) IN SINGLE VENTRICULAR HEART DISEASE, USING UDENAFIL COMPOSITIONS

RELATED APPLICATIONS

This provisional application claims priority from provisional application Ser. No. 62/905,350, which was filed on Sep. 24, 2019, provisional application Ser. No. 62/936,497, which was filed on Nov. 16, 2019 and provisional application Ser. No. 63/023,070, which was filed on May 11, 2020. The foregoing provisional applications are incorporated herein by reference in their entireties.

STATEMENT OF GOVERNMENT INTERESTS

This invention was made with government support under grant numbers HL135691, HL068270, HL135685, HL135680, HL135683, HL135689, HL135682, HL135665, HL135646, HL135678, HL135666 awarded by the National Institutes of Health. The government has certain rights in the invention.

FIELD OF THE INVENTION

Methods for improving exercise performance, single ventricular performance, and myocardial performance index (MPI) in single ventricle bean disease (SVHD) patients, including Fontan patients, using udenafil compositions are provided.

BACKGROUND

The heart is a muscular organ that pumps blood through the blood vessels of the circulatory system. In humans, the heart is located between the lungs and the chest and is divided into left and right sides. The normal human heart has four chambers, a left atrium and left ventricle, the left side, and a right atrium and right ventricle, the right side. The oxygen-poor blood ("blue blood") enters the right side through the right atrium and freshly oxygenated blood ("red blood") exits the left side through the left ventricle. The heart has four valves, the tricuspid valve, the pulmonic valve, the mitral valve and the aortic valve. These valves prevent backflow of blood within the heart and force blood to flow to the lungs and body in a forward direction.

A human heart beats (expands and contracts) approximately 100,000 times per day, pumping five to six quarts of blood each minute, or about 2,000 gallons per day. The left ventricle, the main pumping chamber of the heart, pumps freshly oxygenated blood (red blood) to the body through the aortic valve. The blood then circulates to all parts of the body through arteries and arterioles, delivering oxygen and nutrients. As the blood flows through the circulation, it exchanges oxygen and nutrients for carbon dioxide and metabolic wastes. In this process, the blood transitions from oxygen-rich blood (red blood) to oxygen-poor blood (blue blood). The oxygen-poor blood then returns to the right atrium through the veins of the body. The blue blood passes through the tricuspid valve from the right atrium to the right ventricle, and then it is pumped to the lungs by the right ventricle to exchange carbon dioxide for oxygen. The now freshly oxygenated blood (red blood) returns from the lungs to the left atrium via the pulmonary veins. The blood passes through the mitral valve from the left atrium to the left ventricle, and then is pumped to the body to start the circulation anew.

Thus, the normal human cardiovascular system consists of pulmonary and systemic circulations that are connected in series and powered by the pumping of the right and left ventricles. Gewillig M.: Congenital heart disease. THE FONTAN CIRCULATION. *Heart,* 91:839-846 (2005).

Single ventricle heart disease (SVHD) is a rare pediatric disease that includes a group of cardiac malformations, each of which results in the presence of only a single functional ventricle (pumping chamber). In other words, unlike newborns born with normal hearts (four chambers and two ventricles). SVHD newborns are born with only one functioning ventricle (one pumping chamber), i.e., single ventricle hearts. The non-functioning or missing ventricle (pumping chamber) may be smaller than the single ventricle such that it does not sufficiently function, it may be absent altogether, or it may be configured in such a way as to prevent it from contributing to the normal flow of blood through the circulation. Examples of SVHD include hypoplastic left heart syndrome, tricuspid atresia, double inlet left ventricle, and others.

Typically, SVHD newborns are cyanotic, blue in color, since a mixture of oxygen-poor blood (blue blood) and oxygen-rich blood (red blood) mix together in the single ventricle. The amount of oxygen within the blood mixture leaving the heart is very dependent upon the type, severity and location of the SVHD heart defect. Some SVHD newborns will be mildly cyanotic, whereas others will be severely cyanotic, requiring early intervention to meet the oxygen demands of the body to survive. Unfortunately, without surgical intervention most newborns born with SVHD will not survive.

SVHD can be thought of as having two primary subtypes. In the first subtype, the left ventricle and the aorta (the main artery to the body) are under-developed and the heart is not able to pump blood to the body without an interventional procedure. In the second subtype, the right ventricle and the pulmonary artery (the main artery to the lungs) are under-developed and the heart is not able to pump blood to the lungs.

For those infants born with an under-developed left ventricle and aorta, the first subtype, an urgent intervention is required within the first few days or weeks of life to stabilize blood flow to the body. This intervention is called the Norwood operation, see FIG. 5, and involves rebuilding the aorta (the main artery to the body) using the pulmonary valve and pulmonary artery along with patch material. Since the Norwood operation repurposes the pulmonary artery to supply blood to the body, it also must include a way for blood to get to the lungs. This is accomplished by the inclusion of a "shunt" of blood from the aortic circulation to the pulmonary circulation. This shunt is generally a tube graft that is placed between the right subclavian artery (the artery that supplies blood to the right arm) and the right pulmonary artery. The Norwood operation allow newborns to survive infancy, but is not a permanent solution. This temporary procedure forces the single pumping chamber of the heart to pump blood to both the body and to the lungs, putting it under stress. To relieve this stress, two additional procedures are performed. The first of these, the Glenn shunt or hemi-Fontan, see FIG. 6, occurs at 4-6 months and involves connecting the superior vena cava (the main vein of the upper body) directly to the pulmonary arteries. This allows the blue blood from the upper body to return to the lungs for oxygen repletion without the need for a ventricular pump. The final surgery, the Fontan operation, See FIG. 1A and FIG. 7, typically occurs at 18-48 months of age and involves connecting the inferior vena cava (the main vein of the lower body) directly to the pulmonary arteries. This allows blue blood from the lower body to return to the lungs for oxygen repletion without the need for a ventricular pump specifically pumping the blood to the lungs. After the Fontan operation, all blue blood returns to the lungs and all red blood returns from the lungs to the heart but this is accomplished without the assistance of a ventricular pump dedicated to pumping blood through the lungs to the heart, as with a normal four-chamber heart.

For those infants born with an under-developed right ventricle and pulmonary artery, the second subtype, an urgent neonatal intervention is often not required. This group of babies requires close monitoring to determine if there is too little blood flow to the lungs, too much blood flow to the lungs, or an appropriate amount of blood flow to allow for growth and development. If there is too little blood flow to the lungs, a shunt is often placed, similar to what is done as part of the Norwood operation. If there is too much blood flow to the lungs, a restrictor may be placed around the pulmonary artery to reduce the amount of blood flow to the lungs to avoid the development of congestive heart failure. If the amount of blood flow to the lungs is appropriate, infants born with an under-developed right ventricle and pulmonary artery may go through their initial months of life without the need for a surgical intervention. Whether there is too little, too much, or an appropriate amount of blood flow to the lungs, infants born with this type of SVHD still require the Glenn shunt or hemi-Fontan at 4-6 months of age and the Fontan at 18-48 months of age to relieve the burden from the heart and to separate the blue blood from the red blood.

After the Fontan operation, the subtype of single ventricle heart disease is less important as all patients are left with a common physiology: (i) passive blood flow from the superior and inferior vena cava directly to the lungs bypassing the heart and (ii) a single ventricle that pumps blood to the body. Although this "Fontan circulation" has allowed for the survival of many thousands of patients over the last 40-50 years, it is far from normal. In the absence of a ventricular pump to push blood through the lungs and back to the heart, the Fontan circulation must rely on pressure generated in the veins of the body to accomplish this task. This results in a very elevated 'blood pressure' within the veins and also limits the amount of flow that can circulate through the body in a given amount of time—this is called reduced cardiac output.

Over time, the combination of elevated pressure in the veins and reduced cardiac output lead to a predictable set of long-term complications and, ultimately, to a significantly diminished duration of survival. Complications related to the Fontan circulation include: damage to the kidneys and liver, overload of the lymphatic circulation leading to protein loss in the lungs or gastrointestinal tract, bleeding and blood clotting disorders including the risk of stroke, and progressive dysfunction of the pumping ability of the heart itself.

The ability to perform exercise is used in many forms of heart disease as a marker of the health of the circulation. For those with a Fontan circulation, exercise is likewise an important measure of health and a good predictor of outcomes. While exercise ability is often preserved for those with a Fontan circulation during childhood, it typically begins to drop during adolescence and early adulthood. This deterioration correlates with an increase in the prevalence of heart failure symptoms, hospitalizations, and mortality, often due to the complications of the Fontan circulation itself. In some cases, cardiac transplantation may remain a therapeutic option, but cardiac transplantation comes with its own sets of risks, and patients with Fontan circulation may often be poor candidates for a heart transplant due to chronic and progressive dysfunction of many organ systems.

Notwithstanding this long-standing very serious congenital heart disease, to date, no pharmacotherapy has been approved by the U.S. Food & Drug Administration (FDA) or any other equivalent agency through-out the world for the treatment of SVHD patients, including Fontan patients. Accordingly, there is a real need and demand for new pharmacotherapies for SVHD patients, including Fontan patients, relating to complications of SVHD and the Fontan circulation, with the goals of increasing the life span of SVHD patients, including Fontan patients, and avoiding or delaying the progression of the disease and the need for cardiac transplantation.

There is also a real need and demand for new pharmacotherapies for SVHD patients, including Fontan patients, to (i) improve the myocardial performance index ("MPI"), (ii) improve single ventricular performance, (iii) improve exercise capacity at the ventilatory anaerobic threshold (VAT) and/or the maximal aerobic capacity (max $VO_2$ or $VO_2$ max), (iv) improve the work rate at VAT, (v) improve the ventilatory equivalents of carbon dioxide ($VE/VCO_2$) at VAT, and/or (vi) improve cardiac performance of the single ventricle.

SUMMARY OF THE INVENTION

The present invention overcomes the above-mentioned drawbacks and disadvantages associated with current treatments of SVHD patients, including Fontan patients, through the discovery of novel methods of treating SVHD patients, including Fontan patients.

Generally speaking, the methods of the present invention are directed to the use of udenafil or a pharmaceutically acceptable salt thereof, to treat SVHD patients, including Fontan patients. More specifically, methods of the present invention comprise administering, preferably daily, to a SVHD patient, including a Fontan patient, an effective amount of udenafil or a pharmaceutically acceptable salt thereof to improve, amongst other things, their MPI and exercise capacity or performance.

In general, the methods of the present invention include administering daily an effective amount of udenafil or a pharmaceutically acceptable salt thereof, to the SVHD patient, including a Fontan patient, to improve:

(a) ventricular performance of the SVHD patient's single functioning ventricle as measured by MPI;

(b) exercise capacity as measured by oxygen consumption at VAT;

(c) exercise capacity as measured by oxygen consumption at maximal effort or max $VO_2$;

(d) work rate at VAT;

(e) $VE/VCO_2$ at VAT;

(f) diastolic blood pressure at rest; and (g) oxygen saturation (%) at rest, each individually, collectively or in any combination.

Preferably, the methods of the present invention improve (a)-(g) listed above, including individually, collectively or in any combination thereof. Preferably, the methods of the present invention improve at least the combination of (a)-(e) listed above. Most preferably, (a)-(g) listed above, including individually, collectively or in any combination thereof, are improved in accordance with the present invention by administering daily to a SVHD patient, including a Fontan patient, an effective amount of udenafil or a pharmaceutical acceptable salt thereof.

Improvements in single ventricle performance in accordance with the methods of the present invention include improvements in both systolic and diastolic function. These can be demonstrated by improvements in, but not limited to, blood pool MPI, tissue Doppler MPI, cardiac output (estimated by the product of the integral under the Doppler derived outflow curve and the heart rate), and other measures of single ventricle heart performance. Improvements in exercise capacity or performance in accordance with the methods of the present invention include, but are not limited to, improvements in exercise capacity or performance at anaerobic threshold ("VAT") and/or improvements in exercise capacity or performance at maximal effort or max $VO_2$. Also in accordance with the present invention, there are improvements in work rate at VAT, ventilatory equivalents of carbon dioxide at VAT ($VE/VCO_2$), diastolic blood pressure at rest and/or oxygen saturation (%) at rest, when the methods of the present invention are practiced with regard to SVHD patients, including Fontan patients.

Generally, "effective amount" is used herein to mean an amount of udenafil or a pharmaceutically acceptable salt thereof, that is sufficient to elicit or induce a therapeutic or pharmacologic effect without causing treatment-limiting side effects.

More specifically, "effective amount" is used herein to mean an amount of udenafil or a pharmaceutically acceptable salt thereof, that is sufficient to elicit or induce a therapeutic or pharmacologic effect in a SVHD patient, including a Fontan patient, without causing treatment-limiting toxicity, treatment limiting side effects associated with inhibition of PDE6 and/or PDE11, and/or any other treatment-limiting side effects.

An example of an "effective amount" of udenafil or a pharmaceutically acceptable salt thereof in accordance with the present invention includes a total daily amount in a range that includes, but is not limited to, from about 87.5 mg to about 175 mg. More preferably, an "effective amount" of udenafil or a pharmaceutically acceptable salt thereof in accordance with the present invention includes a total daily amount in a range from about 125 mg to about 175 mg. Even more preferably, an "effective amount" of udenafil or a pharmaceutically acceptable salt thereof in accordance with the present invention includes an oral dosage amount that includes, but is not limited to, a single dosage amount administered daily, including a single dosage amount of about 75 mg or 87.5 mg administered once or twice a day and a single dosage amount of about 125 mg administered once daily.

The present invention also contemplates methods which comprise administering, preferably daily, an effective amount of udenafil or a pharmaceutically acceptable salt thereof, to a SVHD patient, including a Fontan patient, for improving, amongst other things, MPI, ventricular performance, cardiac output, exercise capacity or performance at VAT, exercise capacity or performance at maximal effort or $VO_2$ max, work rate at VAT, $VE/VCO_2$ at VAT, diastolic blood pressure at rest and oxygen saturation (%) at rest, individually, collectively or in any combination, without causing treatment-limiting side effects, for example, interference with visual transduction or function, back pain, myalgia, sperm concentration or quality. In other words, the present invention contemplates treatments, preferably daily, of a SVHD patient, including a Fontan patient, with an effective amount of an effective PDE5 inhibitor, preferably udenafil or a pharmaceutically acceptable salt thereof, without causing treatment limiting side effects associated with inhibition of phosphodiesterase-6 ("PDE6") and/or phosphodiesterase-11 ("PDE11"). As used herein, PDE6 includes any isoenzyme, variant, catalytic subunit and/or inhibitory subunit of PDE6, such as PDE6α, PDE6β, PDE6γ, PDE6R and/or PDE6C, individually, collectively, or in any combination, As used herein PDE11, includes phosphodiesterase-11A (PDE11A) and any isoenzyme, variant, catalytic subunit and or inhibitory subunit of PDE11, such as PDE11A, including PDE11A1, PED11A2, PDE11A3 and/or PDE11A4, individually, collectively, or in any combination.

In one embodiment, the present invention is directed to a method of improving the MPI in a SVHD patient, including a Fontan patient. As used herein MPI measures both systolic and diastolic function for the assessment of global heart function. The method comprises administering, preferably daily, an effective amount of an effective PDE5 inhibitor to the patient, where the PDE5 inhibitor is preferably udenafil or a pharmaceutically acceptable salt thereof.

It is to be understood that by "improve, improving, improvement in or improved", with respect to MPI in accordance with the present invention, it means herein to improve single ventricle performance, i.e., to improve the diastolic and systolic function of the single functioning ventricle. In other words, the single functioning ventricle squeezes better or more efficiently per heartbeat. As a result, the cardiac output and the amount of blood flow that can circulate in a given amount of time throughout the body of the SVHD patients, including Fontan patients, who practice or who are treated in accordance with the methods of the present invention are increased or improved, especially as compared to SVHD patients, including Fontan patients, who are not treated in accordance with the methods of the present invention. Thus, the methods of the present invention result in MPI, or other disclosed measures of ventricular performance, improvement in a SVHD patient, including a Fontan patient, as compared to MPI, or other disclosed measures of single ventricular performance in the absence of the methods of the present invention (e.g., in the absence of udenafil administration). For example, the improvement can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater as compared to blood pool MPI, or other disclosed measures of single ventricular performance in the absence of the methods of the present invention (e.g., in the absence of daily udenafil administration). The method comprises administering, preferably daily, an effective amount of an effective PDE5 inhibitor to the patient, where the PDE5 inhibitor is preferably udenafil or a pharmaceutically acceptable salt thereof.

In one embodiment, the present invention is directed to a method of improving systolic function of the single functioning ventricle of a SVHD patient, including a Fontan patient. The method comprises administering, preferably daily, an effective amount of an effective PDE5 inhibitor or a pharmaceutically acceptable salt thereof to the SVHD patient, where the PDE5 inhibitor is preferably udenafil or a pharmaceutically acceptable salt thereof.

In one embodiment, the present invention is directed to a method of improving diastolic function of the single functioning ventricle of a SVHD patient, including a Fontan patient. The method comprises administering, preferably daily, an effective amount of an effective PDE5 inhibitor or a pharmaceutically acceptable salt thereof to the SVHD patient, where the PDE5 inhibitor is preferably udenafil or a pharmaceutically acceptable salt thereof.

In one embodiment, the present invention is directed to a method of improving cardiac output of the single functioning ventricle of a SVHD patient, including a Fontan patient. The method comprises administering, preferably daily, an effective amount of an effective PDE5 inhibitor or a pharmaceutically acceptable salt thereof to the SVHD patient, where the PDE5 inhibitor is preferably udenafil or a pharmaceutically acceptable salt thereof.

In one embodiment, the present invention is directed to a method of improving the ability of the single functioning ventricle in a SVHD patient, including a Fontan patient to squeeze. The method comprises administering, preferably daily, an effective amount of an effective PDE5 inhibitor or a pharmaceutically acceptable salt thereof to the SVHD patient, including a Fontan patient, where the PDE5 inhibitor is preferably udenafil or a pharmaceutically acceptable salt thereof.

In another embodiment, the present invention is directed to a method of improving the venous pressure by decreasing the elevation in venous pressure in a SVHD patient, including a Fontan patient. The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In one embodiment, the present invention is directed to a method of improving the amount of blood flow that can circulate through the body of the SVHD patient, including a Fontan patient, in a given amount of time. The method comprises administering, preferably daily, an effective amount of an effective PDE5 inhibitor or a pharmaceutically acceptable salt thereof to the SVHD patient, including a Fontan patient, where the PDE5 inhibitor is preferably udenafil or a pharmaceutically acceptable salt thereof.

Thus, the present invention is directed to a method of improving global single ventricular performance of the single functioning ventricle in a SVHD patient, including a Fontan patient. The method comprises administering, preferably daily, an effective amount of an effective PDE5 inhibitor or a pharmaceutically acceptable salt thereof to the SVHD patient, where the PDE5 inhibitor is preferably udenafil or a pharmaceutically acceptable salt thereof.

In yet another embodiment, the present invention is directed to a method of improving diastolic blood pressure at rest in a SVHD patient, including a Fontan patient, whereby the SVHD patient's, including the Fontan patient's, diastolic blood pressure at rest is significantly lowered. The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In yet another embodiment, the present invention is directed to a method of improving oxygen saturation (%) at rest in a SVHD patient, including a Fontan patient. The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In yet another embodiment, the present invention is directed to a method of improving exercise performance or capacity in a SVHD patient, including a Fontan patient. The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In another embodiment, the present invention is directed to a method of improving exercise performance or capacity at the ventilatory anaerobic threshold ("VAT") in a SVHD patient, including a Fontan patient. The methods of the present invention result in improved $VO_2$ at VAT in SVHD patient, including the Fontan patient, as compared to $VO_2$ at VAT in SVHD patients, including Fontan patients, who are not treated with or do not practice the methods of the present invention (e.g., in the absence of daily udenafil administration in accordance with the methods of the present invention). For example, the improvement can be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater as compared to $VO_2$ at VAT in the absence of the methods of the present invention (e.g., in the absence of daily udenafil administration). The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In another embodiment, the present invention is directed to a method of improving exercise performance or capacity at maximal effort or max $VO_2$ in a SVHD patient, including a Fontan patient. The methods of the present invention result in improved $VO_2$ at the SVHD patient's, including the Fontan patient's, maximal effort, as compared to $VO_2$ at maximal effort in the absence of the methods of the present invention (e.g., in the absence of daily udenafil administration). For example, the improvement can be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater, as compared to $VO_2$ at maximal effort in the absence of the methods of the present invention (e.g., in the absence of daily udenafil administration). The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In another embodiment, the present invention is directed to a method of improving work rate at VAT in a SVHD patient, including a Fontan patient. The methods of the present invention result in improved work rate at the SVHD patient's, including the Fontan patient's, VAT, as compared to the work rate at VAT in the absence of the methods of the present invention (e.g., in the absence of daily udenafil administration). For example, the improvement can be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater, as compared to $VO_2$ at VAT in the absence of the methods of the present invention (e.g., in the absence of daily udenafil administration). The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In another embodiment, the present invention is directed to a method of improving ventilatory equivalents of carbon dioxide at the VAT ("VE/VCO$_2$") at VAT in a SVHD patient, including a Fontan patient. The methods of the present invention result in improved VE/VCO$_2$ at the SVHD patient's, including the Fontan patient's, VAT, as compared to the VE/VCO$_2$ at VAT in the absence of the methods of the present invention (e.g., in the absence of daily udenafil administration). For example, the improvement can be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater, as compared to VO$_2$ at VAT in the absence of the methods of the present invention (e.g., in the absence of daily udenafil administration). The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In one embodiment, the present invention is directed to improved methods for treating a SVHD patient, including a Fontan patient, who has undergone heart reconstruction of the abnormal SVHD heart, wherein the daily methods of the present invention result in fewer or less severe adverse events, as compared to conventional methods of treating such a SVHD patient, including a Fontan patient.

In another embodiment, the methods of the present invention result in few, if any, serious adverse events, moderate adverse events, or mild adverse events. The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In one embodiment, the present invention is directed to improved methods for treating a SVHD patient who has undergone a Fontan procedure. In one such embodiment, the Fontan patient is diagnosed with hypoplastic left heart syndrome (HLHS), but first had a Norwood procedure, see, e.g., FIG. 5, followed by a Hemi-Fontan or Bi-directional Glenn procedure, see, e.g., FIG. 6, before undergoing the Fontan procedure, see, e.g., FIG. 1A and FIG. 7. In another such embodiment, the Fontan patient first had a Hemi-Fontan or Bi-directional Glenn procedure before undergoing the Fontan procedure. The method comprises administering, preferably daily, an effective amount of an effective PDE5 inhibitor to the SVHD patient, including a Fontan patient, where the PDE5 inhibitor is preferably udenafil or a pharmaceutically acceptable salt thereof.

In one embodiment, the present invention is directed to improved methods for treating a SVHD patient, including a Fontan patient, wherein the SVHD is selected from a group of SVHDs consisting of patients having an atrioventricular canal defect (AV Canal), a double inlet left ventricle (DILV), a double outlet right ventricle (DORV), Ebstein's anomaly, HLHS, mitral valve atresia (usually associated with HLHS), pulmonary atresia with intact ventricular septum (PA/IVS), a single left ventricle, tricuspid valve atresia and tricuspid valve atresia with stenosis. The method comprises administering, preferably daily, an effective amount of an effective PDE5 inhibitor to the SVHD patient, including a Fontan patient, where the PDE5 inhibitor is preferably udenafil or a pharmaceutically acceptable salt thereof. In an exemplary embodiment, the methods of the present invention comprise administering an effective amount of an effective PDE5 inhibitor or a pharmaceutically acceptable salt thereof, where the PDE5 inhibitor is preferably udenafil or a pharmaceutically acceptable salt thereof, once a day to a SVHD patient, including a Fontan patient.

In another embodiment, the methods of the present invention comprise administering an effective amount of an effective PDE5 inhibitor or a pharmaceutically acceptable salt thereof, where the PDE5 inhibitor is preferably udenafil or a pharmaceutically acceptable salt thereof, twice a day to a SVHD patient, including a Fontan patient.

In another embodiment, the methods of the present invention comprise administering an effective amount of an effective PDE5 inhibitor or a pharmaceutically acceptable salt thereof, where the PDE5 inhibitor is preferably udenafil or a pharmaceutically acceptable salt thereof, three or more times a day to a SVHD patient, including a Fontan patient.

In another embodiment, the SVHD patient, including a Fontan patient, is a pediatric patient of about 2 to about 18 years of age. Treatment of adult patients are also encompassed by the methods of the invention.

In yet another embodiment, the present invention is directed to improved methods for treating a SVHD patient, including a Fontan patient, wherein the methods of the present invention show an improvement in the SVHD patient's, including Fontan patient's, compliance with a dosing schedule of udenafil or a pharmaceutically acceptable salt thereof, as compared to SVHD patients, including Fontan patients, prescribed a non-udenafil drug.

Finally, in yet another embodiment, the methods of the present invention may result in a unique characteristic pharmacokinetic profile. The pharmacokinetic profile can comprises a $C_{max}$ between 300 and 700 ng/ml, or more specifically, about 500 ng/ml; a $T_{max}$ between 1 and 1.6 hr, or more specifically, about 1.3 hr; an $AUC_\tau$ between 2550 and 4150 ng·hr/ml or more, specifically about 3350 ng·hr/ml; and an $AUC_{0-24}$ between 5110 and 8290 ng·hr/ml or more, specifically about 6701 ng·hr/ml.

It is to be understood that present invention contemplates udenafil drug products that are therapeutically equivalent to the udenafil drug products of the present invention. In other words, the present invention contemplates udenafil drug products that (i) are therapeutically equivalent, (ii) are bioequivalent, (iii) are interchangeable, and (iv) have bioavailabilities that, when administered to a SVHD patient, including a Fontan patient in accordance with the methods of the present invention, are effective in carrying out or performing the objectives of the present invention.

Thus, in accordance with one embodiment of the present invention, the present invention contemplates drug formulations that have a 90% confidence interval (90% CI) for a pharmacokinetic profile wherein the ratio of the means lies within the range of between about 0.8 and about 1.25. In another embodiment in accordance with the present invention, the present invention contemplates interchangeable udenafil drug formulations that have a 90% confidence interval (90% CI) for a pharmacokinetic profile wherein the ratio of the means lies within the range of between about 0.8 and about 1.2. The present invention therefore contemplates SVHD patients, including Fontan patients, who are treated with or practice the methods of the present invention, having a udenafil plasma concentration that can vary by up to about 45% (i.e. −20 to +25%) of a pharmacokinetic profile, such as their $C_{max}$, $T_{max}$ and AUC. More preferably, the present invention contemplates SVHD patients, including Fontan patients, who are treated with or practice the methods of the present invention, having a udenafil plasma concentration that can vary by up to about 40% (i.e. –20 to +20%) of a pharmacokinetic profile, such as their $C_{max}$, $T_{max}$, $AUC_t$ and $AUC_{0-24}$. By way of example, the present invention contemplates SVHD patients, including Fontan patients, who are treated with or practice the methods of the present invention, having a udenafil pharmacokinetic profile:

> (a) $C_{max}$ plasma concentration of about –20 to about +25% of about 500 ng/ml, and more preferably a udenafil $C_{max}$ plasma concentration of about –20 to about +20% of about 500 ng/ml; (b) $T_{max}$ of about –20 to about +25% of about 1.3 hr, and more preferably a udenafil $T_{max}$ of about –20 to about +20% of 1.3 hr;
>
> (c) $AUC_t$ of about –20 to about +25% of about 3350 ng·hr/ml, and more preferably a udenafil $AUC_t$ of about –20 to about +20% of about 3350 ng·hr/ml; and
>
> (d) $AUC_{0-24}$ of about –20 to about +25% of about 6701 ng·hr/ml, and more preferably a udenafil $AUC_{0-24}$ of about –20 to about +20% of about 6701 ng·hr/ml, individually, collectively, or in any combination.

Thus, the present invention contemplates bioequivalent and interchangeable udenafil drug products for use in accordance with the methods of the present invention. In addition, the present invention contemplates udenafil drug products that produce the above referenced $C_{max}$, $T_{max}$, $AUC_t$ and/or $AUC_{0-24}$ in SVHD patients, including Fontan patients, when administered to SVHD patients, including Fontan patients, in accordance with the methods of the present invention.

It should be further understood that the above summary of the present invention is not intended to describe each disclosed embodiment or every implementation of the present invention. The foregoing description further exemplifies illustrative embodiments and provides explanation of the present invention as claimed. In several places throughout the specification, guidance is provided through examples, which examples can be used in various combinations. In each instance, the examples serve only as representative groups and should not be interpreted as exclusive examples.

BRIEF DESCRIPTION OF THE DRAWINGS

The foregoing and other objects, advantages and features of the present invention, and the manner in which the same are accomplished, will be readily apparent to those of skill in the art from the following brief description of the drawings, the detailed description of the present invention and the examples, which illustrate embodiments, wherein:

FIG. 7 is a schematic drawing of an exemplary Fontan procedure (Stage 3), an Extracardiac Fenestrated Fontan procedure, of a reconstructed SVHD heart with Hypoplastic Left Heart Syndrome (HLHS).

DETAILED DESCRIPTION OF THE INVENTION

I. Fontan Physiology

Figure 1A:
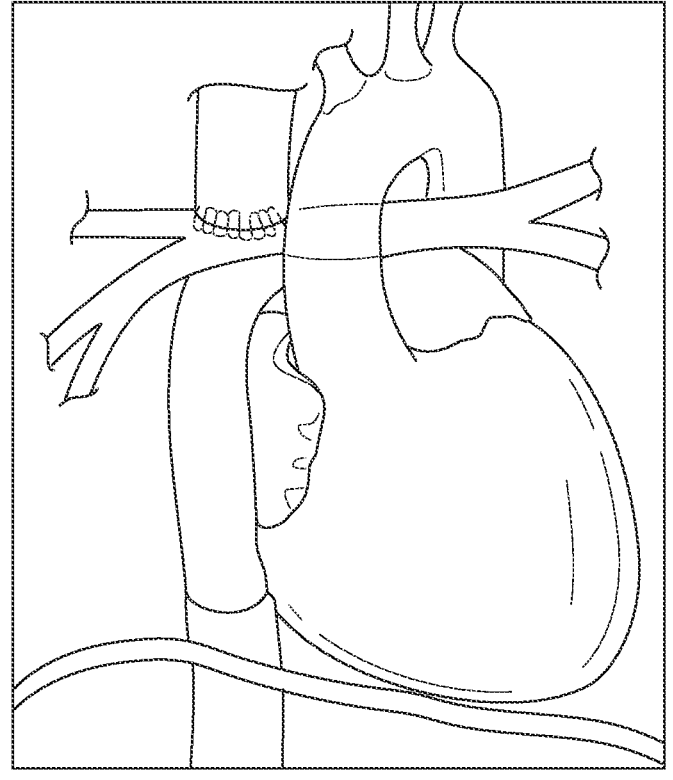
FIG. 1A is a schematic drawing of an exemplary Fontan physiology.

The Fontan physiology is the definitive palliation for those classes of congenital heart defects that share the common feature of a functional single ventricle. They include defects that result in hypoplastic (malfunctioning) left or right ventricles. Usually through a series of 2 or 3 operations, the systemic and pulmonary circulations are separated to significantly eliminate the mixing of oxygenated and un-oxygenated blood caused by the congenital heart defects. This is accomplished by directly attaching the superior and inferior vena cavae to the pulmonary arteries, i.e., the total cavopulmonary connection. This results in a Fontan physiology that works as follows: (1) the single systemic ventricle pumps oxygenated blood (red blood) out the aorta to the body's systemic arterial vascular bed, (2) the systemic venous blood (blue blood) then returns by the vena cavae and the blue blood flows passively through the pulmonary vascular bed for oxygen uptake in the lungs without the aid of a sub-pulmonary ventricle to oxygenate the blue blood, and (3) the now oxygenated blood (red blood) then returns to the functioning single systemic ventricle pump via the common systemic functioning atrium and the red blood-blue blood circulation cycle is repeated. This anatomy is illustrated in FIG. 1A and FIG. 7.

The Fontan operation, which creates a total cavopulmonary connection, separates the systemic and pulmonary circuits and eliminates both hypoxemia and ventricular volume overload. However, following the Fontan operation there is no ventricular pump to propel the blue blood into the pulmonary arteries. Instead, the blue blood returns to the lungs via passive flow from the systemic veins. Thus, the major physiologic consequence of this type of palliation is that pulmonary blue blood flow is completely dependent upon the pressure gradient from the systemic venous bed to the atrium. The normal circulation flow through the pulmonary bed is augmented by the increased pressure generated by the right ventricle. In a healthy adolescent, this results in an increase of about 20 to 25 mm Hg in the pressure present in the pulmonary arteries at rest, which may double with exercise. With the Fontan physiology, there is no sub-pulmonary ventricle and thus no augmentation of pressure as the blue blood enters the pulmonary arteries. At rest, the pressure gradient across the pulmonary vascular bed is significantly less. The ability to increase this pressure gradient with exercise is extremely limited by the body's ability to tolerate increasingly elevated central venous pressures.

As a consequence of being entirely dependent upon the passive drop in venous pressure to drive pulmonary blood flow, the Fontan physiology is exquisitely sensitive to changes in pulmonary vascular resistance. Even increases that are well within the normal range for pulmonary resistance in normal physiology will have detrimental effects on the Fontan physiology. The use of udenafil offers a potential therapy that is unique to this class of palliated congenital heart defects. Unlike other uses for PDE-5 inhibitors, this therapy would be to lower pulmonary vascular resistance in a population without elevated pulmonary vascular resistances or pressures. This is a distinctly different use of this class of agents as compared to patients with (i) structurally normal hearts and pulmonary vascular disease, such as pulmonary arterial hypertension (PAH) and chronic obstructive pulmonary disease (COPD), (ii) heart failure, such as congestive heart disease, or (iii) the very rare patient with congenital heart disease palliated with a two ventricle repair (and thus having a sub-pulmonary ventricle) and associated pulmonary vascular disease.

II. Clinical Measurements Relevant to Fontan Patients

For children born with functional single ventricle or single ventricular congenital heart disease, the Fontan procedure is the current standard of care. The Fontan procedure is palliative, rather than curative, and while it has greatly increased the survival of pediatric subjects with functional single ventricle heart disease, the procedure also results in a series of side effects and complications that can lead to attrition of patients, with complications such as arrhythmias, ventricular dysfunction, and unusual clinical syndromes of protein-losing enteropathy (PLE) and plastic bronchitis, as well as hepatic and kidney complications.

In certain embodiments, the disclosed present invention relates to improving or preventing the decline of specific clinically relevant physiological measurements that are indicative of a patient's health following a Fontan procedure. Such measurements include, but are not limited to, exercise testing, vascular function testing, and echocardiographic assessment of ventricular performance.

III. Exercise Testing

Exercise testing can include assessment of $VO_2$ values during maximal effort or at the ventilator anaerobic threshold (VAT). $VO_2$ max, or maximal oxygen consumption, refers to the maximum amount of oxygen that an individual can utilize during intense exercise. This measurement is generally considered a reliable indicator of cardiovascular fitness and aerobic endurance. The more oxygen a person can use during high level exercise, the more energy that person can produce. This test has been the standard for cardiorespiratory fitness because muscles need oxygen for prolonged (aerobic) exercise; blood carries oxygen to the muscles and the heart must pump adequate amounts of blood to meet the demands of aerobic exercise.

$VO_2$ is often measured by putting a mask on a subject, and measuring the volume and gas concentrations of inhaled and expired air. This measurement is often used in both clinical settings and research and is considered the most accurate. Testing commonly involves either exercising on a treadmill or riding a cycle ergometer at increasing intensity until exhaustion, and is designed to provide readings at a maximal effort of the subject and/or at the subject's anaerobic threshold.

SVHD patients, including SVHD patients that have previously undergone a Fontan procedure, will generally see a decline in $VO_2$ measurements over time. However, when practicing or treating a SVHD patient, including a Fontan patient, is treated with a method according to the present invention, the $VO_2$ measurement (i) is maintained at a similar level, demonstrating that there has been no further decline in $VO_2$ measurement, or (ii) improved with therapy, demonstrating that there has been an increase in $VO_2$, and/or the rate of decline in $VO_2$ measurement is reduced, thus, improved, each indicating that the treatments or methods of the present invention are clinically beneficial. In some SVHD patients, treatment in accordance with the present invention may significantly slow or decrease the decline in $VO_2$ measured during exercise.

In one embodiment, the present invention is directed to a method of improving or maintaining $VO_2$ measurements of a SVHD patient or a subject who has previously had a Fontan procedure. The method of the present invention comprises administering, preferably daily, an effective amount of an effective PDE5 inhibitor to a SVHD patient, including a Fontan patient, where the PDE5 inhibitor is preferably udenafil or a pharmaceutically acceptable salt thereof. In some embodiments of the present invention, $VO_2$ is measured at maximal effort, while in other embodiments, $VO_2$ is measured at the subject's anaerobic threshold (VAT).

In some embodiments, the disclosed methods and compositions of the present invention are administered to a SVHD patient, including a Fontan patient, and result in no decrease, or a minimal decrease, in exercise capacity over time. More specifically, the disclosed methods and compositions of the present invention may result in a decrease in exercise capacity of less than about 40, less than about 35, less than about 30, less than about 35, less than about 20, less than about 15, less than about 10, or less than about 5% over time. The time period between a first and second measurement used to calculate the decrease in exercise capacity can be, for example, about 1, about 2, about 3, about 4, about 5, about 6, about 7, about 8, about 9, about 10, about 11, or about 12 months; about 1, about 2, about 3, about 4, about 5, about 6, about 7, about 8, about 9, about 10, about 11, about 12, about 13, about 14, or about 15 years, or any combination thereof, e.g., 1 year, 3 months; 4 years, 7 months, etc.

In some embodiments, the disclosed methods and compositions of the present invention may be administered to a SVHD patient, including a Fontan patient, and result in an improvement of exercise capacity. More specifically, the disclosed methods and compositions of the present invention may result in a 1, 2, 5, 10, 15, 20, 25, 30, 35, 40, 45, or 50% or more improvement in $VO_2$ at maximal effort. Alternatively, the disclosed methods and compositions of the present invention may result in a 1, 2, 5, 10, 15, 20, 25, 30, 35, 40, 45, or 50% or more improvement in $VO_2$ at the SVHD patient's, including the Fontan patient's, ventilatory anaerobic threshold (VAT).

IV. Vascular Function Testing

Vascular endothelial dysfunction is an important outcome for assessing vascular health in intervention studies. It is now well established that vascular endothelial dysfunction is positively associated with traditional cardiovascular disease (CVD) risk factors, and independently predicts cardiovascular events over intervals of 1 to 6 years.

Pulse amplitude tonometry (PAT), a FDA-approved method for assessing vascular function, is increasingly being used as an alternative measure of endothelium-dependent dilation in response to reactive hyperemia and flow-mediated dilation (FMD). The PAT device records digital pulse wave amplitude (PWA) using fingertip plethysmography. PWA can be measured continuously during three phases: a quiet baseline period, 5-min forearm occlusion, and reactive hyperemia following cuff release. Unlike FMD, PAT testing is not dependent upon a highly skilled technician and post-test analysis is largely automated. Most importantly, at least one longitudinal study has shown that PAT measures of endothelial function predict CVD events over a 6-year follow-up period. These significant advantages may make PAT testing suitable for clinical practice if prognostic significance and reliability can be verified.

SVHD patients, including SVHD patients that have previously undergone a Fontan procedure, will generally see a decline in vascular function over time. Treating a SVHD patient, including a Fontan patient, that improves or prevents further decline in vascular function of a SVHD patient, including a Fontan patient, would indicate that the treatment is clinically beneficial and may improve the SVHD patient's, including the Fontan patient's, quality of life or prevent decline in cardiovascular function.

In one embodiment, the present invention is directed to a method of improving or maintaining vascular function of SVHD patients, including SVHD patients that have previously undergone a Fontan procedure. The method comprises administering, preferably daily, an effective amount of an effective PDE5 inhibitor to a SVHD patient, including a Fontan patient, where the PDE5 inhibitor is preferably udenafil or a pharmaceutically acceptable salt thereof. In some embodiments, vascular function is measured using a PAT index.

In some embodiments, the disclosed methods and compositions of the present invention are administered to a SVHD patient, including a Fontan patient, and result in no decrease, or a minimal decrease, in vascular function over time. Vascular function can be measured using any conventional known technique, including but not limited to pulse amplitude tonometry measurements, the natural log of reactive hyperemia index, Reactive Hyperemia Index, Framingham (RHI), area under the curve to max-occlusion/control, average up to max-occlusion/control, and other known EndoPAT indices. In some embodiments of the present invention, vascular function is measured using a PAT index. More specifically, the disclosed methods and compositions of the present invention may result in a decrease in vascular function of less than about 40, less than about 35, less than about 30, less than about 35, less than about 20, less than about 15, less than about 10, or less than about 5% over time. The time period between a first and second measurement used to calculate the decrease in vascular function can be, for example, about 1, about 2, about 3, about 4, about 5, about 6, about 7, about 8, about 9, about 10, about 11, or about 12 months; about 1, about 2, about 3, about 4, about 5, about 6, about 7, about 8, about 9, about 10, about 11, about 12, about 13, about 14, or about 15 years, or any combination thereof, e.g., 1 year, 3 months; 4 years, 7 months, etc.

In some embodiments, the disclosed methods and compositions of the present invention may be administered to a SVHD patient, including a Fontan patient and result in an improvement of vascular function. Vascular function can be measured using any conventional known technique, including but not limited to pulse amplitude tonometry measurements, the natural log of reactive hyperemia index, Reactive Hyperemia Index, Framingham RHI, area under the curve to max-occlusion/control, average up to max-occlusion/control, and other known EndoPAT indices. In some embodiments of the present invention, vascular function is measured using a PAT index. More specifically, the disclosed methods and compositions may result in about a 1, about 2, about 5, about 10, about 15, about 20, about 25, about 30, about 35, about 40, about 45, or about 50% or more improvement in one or more measurements of vascular function, including but not limited to pulse amplitude tonometry measurement, the natural log of reactive hyperemia index, Reactive Hyperemia Index, Framingham RHI, area under the curve to max-occlusion/control, average up to max-occlusion/control, and other known EndoPAT indices.

V. Echocardiographic Assessment of Ventricular Performance

Ventricular performance and cardiac contractility are important measurements that can reveal impairment of cardiovascular health before overt heart failure is present. Ventricular performance can be assessed using echocardiographic methods and quantified via a myocardial performance index or MPI. MPI is an index that combines systolic and diastolic function. Specifically, MPI is defined as the sum of isovolumic contraction time and isovolumic relaxation time divided by the ejection time.

Various versions of MPI are known in the art, and each version of MPI may be used to assess ventricular performance. For instance, MPI indices may include, but are not limited to, blood pool MPI and tissue Doppler MPI. MPI can be measured by using pulsed-wave tissue Doppler echocardiography (TDE). To calculate MPI using TDE, isovolumetric contraction time (IVCT), isovolumetric relaxation time (IVRT) and ejection time (ET) of the functioning single ventricle are measured. MPI is then determined by adding together the IVCT and the IVRT and dividing the sum by ET.

Patients that have previously undergone a Fontan procedure will generally see a decline in ventricular performance over time. Treating a patient such that the patient's ventricular performance is maintained, exhibits minimal decrease over time, or increases indicates that the treatment is clinically beneficial and may improve patient quality of life or prevent decline in cardiovascular function.

In one embodiment, the present invention is directed to a method of maintaining, producing a minimal decrease in, or increasing ventricular performance of a subject who has previously had a Fontan procedure. The method of the present invention comprises administering, preferably daily, an effective amount of an effective PDE5 inhibitor to the patient, where the PDE5 inhibitor is preferably udenafil or a pharmaceutically acceptable salt thereof. In some embodiments of the present invention, ventricular performance is measured using a myocardial performance index (MPI). In some embodiments, the MPI may be a blood pool MPI, while in other embodiments the MPI may be a tissue Doppler MPI.

In some embodiments, the disclosed methods and compositions of the present invention may be administered to a Fontan patient and result in minimal or no decrease in ventricular performance over time. Ventricular performance can be measured using any conventional known technique, including but not limited to myocardial performance index (MPI), blood pool MPI, tissue doppler MPI, average isovolumetric contraction and relaxation, and other known ventricular performance indices. More specifically, the disclosed methods and compositions of the present invention may result in a decrease in ventricular performance of less than about 40, less than about 35, less than about 30, less than about 35, less than about 20, less than about 15, less than about 10, or less than about 5% over time. The time period between a first and second measurement used to calculate the decrease in ventricular performance can be, for example, about 1, about 2, about 3, about 4, about 5, about 6, about 7, about 8, about 9, about 10, about 11, or about 12 months; about 1, about 2, about 3, about 4, about 5, about 6, about 7, about 8, about 9, about 10, about 11, about 12, about 13, about 14, or about 15 years, or any combination thereof, e.g., 1 year, 3 months; 4 years, 7 months, etc.

In some embodiments, the disclosed methods and compositions of the present invention may be administered to a SVHD patient, including a Fontan patient, and result in an improvement of ventricular performance over time. Ventricular performance can be measured using any conventional known technique, including but not limited to myocardial performance index (MPI), blood pool MPI, tissue doppler MPI, average isovolumetric contraction and relaxation, and other known ventricular performance indices. For example, the disclosed methods and compositions of the present invention may result in about a 1, about 2, about 5, about 10, about 15, about 20, about 25, about 30, about 35, about 40, about 45, or about 50% or more improvement in ventricular performance, as measured by any known technique, including but not limited to myocardial performance index (MPI), blood pool MPI, tissue doppler MPI, average isovolumetric contraction and relaxation, and other known ventricular performance indices.

VI. Methods According to the Invention

The disclosed methods of the present invention relate to improving exercise and ventricular performance in a SVHD patient, including a Fontan patient, and who is in need of improvement in exercise capacity and/or ventricular performance. In general, the methods include administering daily an effective amount of an effective PDE5 inhibitor or a pharmaceutically acceptable salt thereof, preferably as udenafil or a pharmaceutically acceptable salt thereof, to the SVHD patient, including a Fontan patient, to improve:

(a) ventricular performance of the SVHD patient's single functioning ventricle as measured by MPI;

(b) exercise capacity as measured by oxygen consumption at VAT;

(c) exercise capacity as measured by oxygen consumption at maximal effort or max $VO_2$;

(d) work rate at VAT;

(e) $VE/VCO_2$ at VAT, each individually or in any combination;

(f) diastolic blood pressure at rest; and (g) oxygen saturation (%) at rest, each individually, collectively or in any combination.

Preferably, the methods of the present invention improve (a)-(g) listed above, including individually, collectively or in any combination thereof. More preferably, (a)-(g) listed above, including individually, collectively or in any combination thereof, is improved in accordance with the present invention by administering daily to a SVHD patient, including a Fontan patient, an effective amount of udenafil or a pharmaceutical acceptable sat thereof.

As discussed above and used herein, an effective PDE5 inhibitor inhibits the degradative action of cGMP-specific phosphodiesterase type 5 (PDE5) on cyclic GMP in the smooth muscle cells lining the blood vessels that supply blood to various tissues.

As also discussed above and used herein, MPI is a measure of ventricular systolic and diastolic function and a prognostic and progression marker for various heart diseases, as determined by a focused echocardiogram. This numeric value is defined as the sum of isovolumetric contraction time (ICT) and isovolumetric relaxation time (IRT) divided by ejection time (ET) and can be calculated for a single ventricle. The change in the myocardial performance index is determined by velocities obtained from blood pool Doppler assessment of the inflow and outflow tract of the single functioning ventricle. In other words, MPI is a measure of global systolic and diastolic time intervals to assess global cardiac dysfunction and ventricular performance. Moreover, because the MPI is a Doppler index, it is independent of ventricular geometry and can be applied to either left and right ventricular function, depending upon which ventricle is the single functioning ventricle in the SVHD patients.

More specifically, the methods include administering daily an effective amount of an effective PDE5 inhibitor or a pharmaceutically acceptable salt thereof, preferably udenafil or a pharmaceutically acceptable salt thereof, to effect one or more of the above improvements without causing treatment-limiting side effects including, but not limited to, blindness or loss of vision via inhibition of photoreceptor phosphodiesterase enzyme (PDE6), back pain and/or myalgia via inhibition of PDE11, such as 11A1 (PDE11A1) and/or decrease in sperm concentration via inhibition of PDE11, such 11A3 (PDE11A3). Kayik, G. et al.: Investigation of PDE5/PDE6 and PDE5/PDE11 selective potent tadalafil-like PDE5 inhibitors using combination of molecular modeling approaches, molecular fingerprint-based virtual screening protocols and structure-based pharmacophore development. *Journal of Enzyme Inhibition and Medicinal Chemistry,* 32(1):311-330 (2017); Pomara G. and Morelli G.: Inhibition of phosphodiesterase 11 (PDE11) impacts on sperm quality. *Int J Impot Res,* 17:385-386 (2005), and Huang S. A. and Lie, J. D.: Phosphodiesterase-5 (PDE5) Inhibitors. In the Management of Erectile Dysfunction. *Pharmacy and Therapeutics,* 38(7):407-419 (July 2013).

Quite uniquely and surprisingly, the methods of the present invention increase and/or maximize oxygen consumption at the ventilatory anaerobic threshold (VAT) and at maximum effort or max $VO_2$ to improve exercise capacity, and increase and/or maximize work rate at VAT and $VE/VCO_2$ at VAT in SVHD patients, including Fontan patients.

Also, quite uniquely and surprisingly, the methods of the present invention improve the MPI of the SVHD patients, namely, the Fontan patients. In other words, the methods of the present invention improve both systolic and diastolic function of the single functioning ventricle and the global heart function. In other words, the methods of the present invention improve the filling and emptying characteristics, i.e., the squeezing ability of the single functioning ventricle and the overall ability of the reconstructed abnormal SVHD heart of the SVHD patients, including the Fontan patients, to pump the freshly oxygenated blood to the body for peripheral tissue needs.

The clinical value of the MPI improvement is evidenced by the statistically significant improvement in the MPI in those SVHD patients, and in particular the Fontan patients, who were treated with the methods of the present invention, as compared to those SVHD patients, namely the Fontan patients, who were treated with placebo during the FUEL Trial.

The clinical value of the MPI improvement is also evidenced by the improvement of the single ventricular performance as measured by the isovolumic contraction time, isovolumic relaxation time and ejection time using TDE, as discussed above.

By "isovolumetric contraction time" (IVCT), it is meant herein to mean a single ventricular event that occurs early in systole, during which the single ventricle contracts without volume change (isovolumetrically). This period of the cardiac cycle, the squeeze event, takes place while all heart valves are closed.

By "isovolumic relaxation time" (IVRT), it is meant herein to mean the interval period of the cardiac cycle, i.e., the squeeze and relax cycle, that concerns the second heart sound emanating from the closure of the valve to the onset filling of the functioning single ventricle by following the opening of the valve. The IVRT may indicate diastolic dysfunction of the functioning single ventricle.

By "ejection time" (ET), it is meant herein to mean the single ventricular ejection time (UVET) of the reconstructed abnormal heart determined by the opening and closing of the valve during which the pressure differences across the valve are measured.

By "stroke volume," it is meant herein to mean the amount of freshly oxygenated blood that the single functioning ventricle can pump out into the circulatory system in one contraction.

By "cardiac output," it is meant herein to mean the amount of blood the single functioning ventricle in an SVHD patient, including a Fontan patient, can pump through the circulatory system in one minute.[1] The stroke volume and the heart rate determine cardiac output.

[1] A normal adult has a cardiac output on average of about 4.7 liters (5 quarts) of blood per minute.

While each of the improvements in the treatment of SVHD patients, including Fontan patients, in accordance with the methods of the present invention are individually unique and surprising, the combination of improvements in the treatment of SVHD patients, including Fontan patients, is especially unique and surprising.

In another embodiment, it was surprising that that the methods of the invention show improved results when udenafil is administered as compared to prior very limited studies using a non-udenafil PDE5 inhibitor, such as sildenafil or tadalafil. In yet another embodiment, it was surprising that the methods of the invention show fewer side effects, and/or less severe side effects when udenafil is administered, as compared to other prior treatments using a non-udenafil PDE5 inhibitor, such as sildenafil or tadalafil.

In some embodiments, the Fontan patient can be an adult human, whereas in other embodiments, the Fontan patient can be an adolescent human. In some embodiments, the Fontan patient can be between about 12 and about 19 years old, whereas in other embodiments, the Fontan patient can between about 12 and 18 years old. In yet other embodiments, the Fontan patient can be from about 12 to about 16 years old. In yet other embodiments, the Fontan patient can be from about 6 years old to adult. In one embodiment, the Fontan patient can be less than 18 years old.

VII. Doses and Dosage Forms

The structure of udenafil is shown below

In some embodiments, udenafil or a pharmaceutically acceptable salt thereof can be administered at total daily dosage amounts of about 0.01 to about 150 mg/kg. In another embodiment, the udenafil or a pharmaceutically acceptable salt thereof can be administered at total daily doses of about 0.01 mg/kg up to about 30 mg/kg. In another embodiment, udenafil or a pharmaceutically acceptable salt thereof can be administered in a dosage amount of from about 2.5 mg to about 275 mg, such as about 2.5 mg, about 5 mg, about 7.5 mg, about 10 mg, about 12.5 mg, about 15 mg, about 17.5 mg, about 20 mg, about 22.5 mg, about 25 mg, about 27.5 mg, about 30 mg, about 32.5, about 35 mg, about 37.5 mg, about 40 mg, about 42.5 mg, about 45 mg, about 47.5 mg, about 50 mg, about 52.5 mg, about 55 mg, about 57.5 mg, about 60 mg, about 62.5 mg, about 65 mg, about 67.5 mg, about 70 mg, about 72.5 mg, about 75 mg, about 77.5 mg, about 80 mg, about 82.5 mg, about 85 mg, about 87.5 mg, about 90 mg, about 92.5 mg, about 95 mg, about 97.5 mg, about 100 mg, about 102.5 mg, about 105 mg, about 107.5 mg, about 110 mg, about 112.5 mg, about 115 mg, bout 117.5 mg, about 120 mg, about 122.5 mg, about 125 mg, about 127.5 mg, about 130 mg, about 132.5 mg, about 135 mg, about 137.5 mg, about 140 mg, about 142.5 mg, about 145 mg, about 147.5 mg, about 150 mg, about 152.5 mg, about 155 mg, about 157.5 mg, about 160 mg, about 162.5 mg, about 165 mg, about 167.5 g, about 170 mg, about 172.5 mg, about 175 mg, about 180 mg, about 182.5 mg, about 185 mg, about 187.5 mg, about 190 mg, about 192.5 mg, about 195 mg, about 197.5 mg, about 200 mg, about 202.5 mg, about 205 mg, about 207.5 mg, about 210 mg, about 212.5 mg, about 215 mg, about 217.5 mg, about 220 mg, about 222.5 mg, about 225 mg, about 227.5 mg, about 230 mg, about 232.5 mg, about 235 mg, about 237.5 mg, about 240 mg, about 242.5 mg, about 245 mg, about 247.5 mg, about 250 mg, about 252.5 mg, about 255 mg, about 257.5 mg, about 260 mg, about 262.5 mg, about 265 mg, about 267.5 mg, about 270 mg, about 272.5 mg or about 275 mg, so long as any such individual dosage amount does not cause treatment-limiting toxicity or treatment-limiting side effects to the extent that the drug product would not be approved for market. In yet another embodiment, udenafil or a pharmaceutically acceptable salt thereof can be administered at total daily doses of from about 5 mg to about 275 mg, such as about 5 mg, about 10 mg, about 15 mg, about 20 mg, about 25 mg, about 27.5 mg, about 30 mg, about 32.5, about 35 mg, about 37.5 mg, about 40 mg, about 42.5 mg, about 45 mg, about 47.5 mg, about 50 mg, about 55 mg, about 60 mg, about 65 ng, about 70 mg, about 75 mg, about 80 mg, about 85 mg, about 87.5 mg, about 90 mg, about 95 mg, about 100 mg, about 125 mg, about 150 mg, about 175 mg, about 200 mg, about 225 mg, about 250 ng, or about 275 mg, so long as any such individual total daily dose does not cause treatment-limiting toxicity or treatment-limiting side effects to the extent that the total daily dose would not be approved for market.

In still another embodiment, udenafil or a pharmaceutically acceptable salt thereof can be administered in total daily doses of from about 25 mg to about 700 mg, such as about 25 mg, about 37.5 mg, about 50 mg, about 75 mg, about 87.5 mg, 125 mg, about 175 mg, about 200 mg, about 225 mg, about 250 mg, about 275 ng, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, or about 700 mg, so long as any such individual total daily dose does not cause treatment-limiting toxicity or treatment-limiting side effects to the extent that the total daily dose would not be approved for market.

In a further embodiment, udenafil or a pharmaceutically acceptable salt thereof can be administered at a total daily dose of about 37.5 mg, about 75 mg, about 87.5 mg, 125 mg, or about 175 mg. In a further embodiment, udenafil or a pharmaceutically acceptable salt thereof can be administered at a total daily dose range of from about 37.5 mg to about 175 mg, preferably, a total daily dose range of from 75 mg to about 175 mg, more preferably, a total daily dose range of from about 87.5 mg to about 175 mg and, most preferably, a total daily dose range of from 125 mg to about 175 mg. In a preferred embodiment, udenafil or any pharmaceutically acceptable salt thereof can be administered to a Fontan patient in any dosage amount or in any total daily dose, so long as any selected individual dosage amount or any selected individual total daily dose does not cause treatment-limiting toxicity or treatment-limiting side effects to the extent that the total daily dose would not be approved for market.

Thus, the present invention contemplates administration of udenafil or a pharmaceutically acceptable salt thereof to SVHD patients, including Fontan patients, at any dosage amount, at any total daily dose, at any treatment regimen and in any dosage form, so long as when any such dosage amount, total daily dose, treatment regimen or dosage form is selected, it does not cause treatment-limiting toxicity or treatment-limiting side effects to the extent that such would not be approved for market. In particular, the present invention contemplates administration of udenafil or a pharmaceutically acceptable salt thereof in an effective amount to SVHD patients, including Fontan patients to improve MPI, single ventricular performance, systolic and/or diastolic function, ventricular squeeze capability, cardiac output, exercise capacity or performance at VAT and/or max $VO_2$, work rate at VAT, $VE/CO_2$ at VAT, diastolic blood pressure at rest, oxygen saturation (%) at rest and/or decrease the rate of decline of progression of SVHD, as compared to untreated SVHD patients, so long as the therapeutically effective amount does not cause treatment-limiting toxicity, treatment limiting side effects associated with inhibition of PDE6 and/or PDE11, and/or treatment-limiting side effects to the extent that the drug product would not be approved for market.

In one embodiment, the udenafil or a pharmaceutically acceptable salt thereof can be administered once a day.

In another embodiment, the udenafil or a pharmaceutically acceptable salt thereof can be administered once daily or in divided multiple dosages, such as twice a day, three times a day, four times a day or more.

In yet another embodiment, the udenafil or a pharmaceutically acceptable salt thereof can be administered twice a day such that therapeutically effective blood levels are maintained for at least about 1.5 to about 24 hours, more particularly at least about 1.5, about 2, about 3, about 4, about 5, about 6, about 7, about 8, about 9, about 10, about 11, about 12, about 13, about 14, abut 15, about 16, about 17, about 18, about 19, about 20, about 21, about 22, about 23 or about 24 hours of a 24 hour dosing period. Thus, the present invention therefore contemplates udenafil and/or any udenafil active metabolite, such as DA8164 active metabolite, maintaining an effective blood level for any period of time within a 24 hour dosing period.

In some embodiments, the total daily dosage amount of udenafil or a pharmaceutically acceptable salt administered twice a day can be less than the total daily dosage amount of udenafil or a pharmaceutically acceptable salt thereof administered once a day.

In some embodiments, the total daily dosage amount of udenafil or a pharmaceutically acceptable salt thereof administered twice a day, can maintain therapeutically effective blood levels for the same number of hours in a 24 hour period as a higher dosage of udenafil or a pharmaceutically acceptable salt thereof when administered once a day. In other embodiments, the total daily dosage amount of udenafil or a pharmaceutically acceptable salt thereof administered twice a day, can maintain therapeutically effective blood levels for a higher number of hours in a 24 hour period as the same dosage of udenafil or a pharmaceutically acceptable salt thereof when administered once a day. Thus, the present invention contemplates administration of any total daily dosage amount of udenafil or any acceptable salt thereof once daily or in divided doses multiple times a day, such as twice daily, three times daily, four times daily or more, to maintain therapeutically effective blood levels throughout a 24 hour period.

In one embodiment, it is surprising that the administration of twice a day udenafil or a pharmaceutically acceptable salt thereof results in fewer side effects than the administration of once a day udenafil or a pharmaceutically acceptable salt thereof. In another embodiment, it is surprising that twice a day administration of udenafil or a pharmaceutically acceptable salt thereof can achieve therapeutically effective levels of udenafil at a lower total daily dosage than a once a day administration.

In some embodiments, the pharmaceutically acceptable salt of udenafil can be an acid addition salt. In one embodiment, the acid addition salt of udenafil can be an inorganic acid addition salt such as, hydrochloric, hydrobromic, sulfuric, or phosphoric acid addition salt. In another embodiment, the acid addition salt can be an organic acid addition salt such as citrate, tartarate, acetate, lactate, maleate, fumarate, gluconate, methanesulfonate (mesylate), glycolate, succinate, p-toluenesulfonate (tosylate), galacturonate, embonate, glutamate, aspartate, oxalate, benzensulfonate, camphorsulfonate, cinnamate, adipate, or cyclamate. In a particular embodiment, the pharmaceutically acceptable salt of udenafil can be an oxalate, benzensulfonate, camphorsulfonate, cinnamate, adipate, or cyclamate salt.

In some embodiments, the udenafil or a pharmaceutically acceptable salt thereof can be administered as a pharmaceutical composition. In one embodiment, the pharmaceutical composition comprising udenafil or a pharmaceutically acceptable salt thereof can be formulated in a wide variety of oral or parenteral dosage forms on clinical application. Each of the dosage forms can contain various disintegrating agents, surfactants, fillers, thickeners, binders, diluents such as wetting agents or other pharmaceutically acceptable excipients.

The udenafil composition can be administered using any pharmaceutically acceptable method, such as intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal gel or spray formulation.

Further, the udenafil composition can be formulated into any pharmaceutically acceptable dosage form, such as a solid dosage form, including but not limited to a tablet, pill, lozenge, capsule, caplet, orally-disintegrating dosage form, sublingual dosage form, buccal dosage form, liquid, liquid dispersion, liquid suspension, solution, aerosol, pulmonary aerosol, nasal aerosol and semi-solid, namely, ointment, cream, thin film, and gel, and patches such as transdermal patches. Further, the composition may be a controlled release formulation, sustained release formulation, immediate release formulation, modified release formulation or any combination thereof. Further, the composition may be a transdermal delivery system.

In another embodiment, the pharmaceutical composition comprising udenafil or a pharmaceutically acceptable salt thereof can be formulated into a solid dosage form for oral administration, and the solid dosage form can be powders, granules, capsules, tablets, caplets, caches, orally-disintegrating dosage forms, sublingual dosage forms, buccal dosage forms, lozenges or pills. In yet another embodiment, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled, sustained, modified or extended release, enteric release, and the like. The excipients used in the modified release dosage forms are commonly known to a person of ordinary skill in the art.

For example, a solid carrier may be one or more substance that may also act as diluents, flavoring agents, binders, preservatives, oral dosage form disintegrating agents, or an encapsulating material. The oral dosage forms, such as powders, granules, capsules, tablets, caplets, caches, lozenges or pills, preferably contain from 5% to 70% of the udenafil. Suitable carriers are magnesium carbonate, magnesium stearate, talc, sugar, lactose (e.g., lactose monohydrate), pectin, dextrin, starch (e.g., corn starch), gelatin, tragacanth, methylcellulose, sodium carboxymethylcellulose, hydroxypropyl cellulose, low substituted hydroxypropyl cellulose, silicon dioxide (e.g., colloidal silicon dioxide), a low melting wax, cocoa butter, and the like. The term "preparation" is intended to include the formulation of the udenafil solid, liquid or semi-solid matrix with or without encapsulating material.

Liquid form preparations include solutions, suspensions and emulsions, for example, water or water/propylene glycol solutions. For parenteral injection, liquid preparations can be formulated in solution in aqueous polyethylene glycol solution. For example, aqueous solutions suitable for oral use can be prepared by dissolving the udenafil in water and adding suitable colorants, flavors, stabilizers, and thickening agents as desired. In another example, aqueous suspensions suitable for oral use can be made by dispersing the finely divided udenafil in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. In one embodiment, the pharmaceutical composition can be formulated in a liquid dosage form for oral administration, such as suspensions, emulsions or syrups, which may contain, in addition to the udenafil, colorants, flavors, stabilizers, buffers (e.g., buffers to adjust the pH to a desirable range for intravenous use such as salts of inorganic acids such as phosphate, borate, and sulfate), artificial and natural sweeteners, dispersants, thickeners, solubilizing agents, and the like. In other embodiments, the liquid dosage form can include, in addition to commonly used simple diluents such as water and liquid paraffin, various excipients such as humectants, sweeteners, aromatics or preservatives. In particular embodiments, the composition comprising udenafil or a pharmaceutically acceptable salt thereof can be formulated to be suitable for administration to a pediatric patient.

In one embodiment, the pharmaceutical composition can be formulated in a dosage form for parenteral administration, such as sterile aqueous solutions, suspensions, emulsions or non-aqueous solutions. In other embodiments, the non-aqueous solutions or suspensions can include propyleneglycol, polyethyleneglycol, vegetable oils such as olive oil or injectable esters such as ethyl oleate. Alternatively, the pharmaceutical composition can be formulated in a dosage form for rectal or vaginal administration. As abase for suppositories, witepsol, macrogol, tween 61, cacao oil, laurin oil or glycerinated gelatin can be used.

The pharmaceutical preparation may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methylcellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical preparation is preferably in unit dosage form. In such form the preparation is subdivided into unit doses containing appropriate quantities of the udenafil or any acceptable pharmaceutical salt thereof. The unit dosage form can be a packaged preparation, such as a sachet, the package containing discrete quantities of preparation, such as packeted tablets, caplets, capsules, orally-disintegrating dosage forms, sublingual dosage forms, buccal dosage forms and powders in vials or ampoules. Also, the unit dosage form can be a capsule, tablet, caplets, pills, orally-disintegrating dosage forms, sublingual dosage forms, buccal dosage forms, cachet, or lozenge itself, or it can be the appropriate number of any of these in packaged form.

The pharmaceutical compositions may include components to provide immediate release, sustained release, extended release, modified release, convenience and/or comfort. Such components include high molecular weight, anionic mucomimetic polymers, gelling polysaccharides, and finely-divided drug carrier substrates.

In a further embodiment, the pharmaceutical composition comprising udenafil or a pharmaceutically acceptable salt thereof can be formulated as an orally-disintegrating, sublingual or buccal dosage form. Such dosage forms comprise sublingual tablets or solution compositions that are administered under the tongue and buccal tablets that are placed between the cheek and gum.

The pharmaceutical preparation may be prepared by further containing a coating agent for example, the light shielding agent capable of generating free radical by UV light, metal oxides such as titanium oxide and the like are described, and as the free radical scavenger, for example, organic acids such as benzoic acid and the like. In addition, the coating agent may further include, but not be limited to, an water-soluble polymer (e.g., hypromellose or hydroxypropyl cellulose), an enteric coating layer containing polyethylene glycol, triethyl citrate, cellulose acetate phthalate, hydroxypropyl methyl cellulose acetate succinate, polyvinyl acetate phthalate, methyl methacrylate-methacrylic acid copolymers, shellac, cellulose acetate succinate, cellulose acetate trimellitate, hydroxypropyl methyl cellulose phthalate, zein, sodium alginate, and mannitol, and/or enteric coating aqueous solution including, for example, ethylcellulose, medium chain triglycerides, oleic acid, sodium alginate, stearic acid.

In yet a further embodiment, the pharmaceutical composition comprising udenafil or a pharmaceutically acceptable salt thereof can be formulated as a nasal dosage form. Such dosage forms of the present invention comprise solution, suspension, emulsion, and gel compositions for nasal delivery.

In one embodiment, the pharmaceutical composition can be formulated in a liquid dosage form for oral administration, such as solutions, suspensions, emulsions or syrups. In other embodiments, the liquid dosage form can include, in addition to commonly used simple diluents such as water and liquid paraffin, various excipients such as humectants, sweeteners, aromatics or preservatives. In particular embodiments, the composition comprising udenafil or a pharmaceutically acceptable salt thereof can be formulated to be suitable for administration to a pediatric patient.

The dosage of the pharmaceutical composition can vary depending on the patient's weight, age, gender, administration time and mode, excretion rate, and the severity of disease.

VIII. Exercise Testing

Exercise testing can include assessment of $VO_2$ values during maximal effort or at ventilator anaerobic threshold ("VAT"). $VO_2$ max ("peak $VO_2$"), or maximal ("peak") oxygen consumption, refers to the maximum amount of oxygen that an individual can utilize during intense exercise. This measurement is generally considered a reliable indicator of cardiovascular fitness and aerobic endurance Theoretically, the more oxygen a person can use during exercise, the more energy that person can produce. This test is often used for cardiorespiratory fitness because muscles need oxygen for prolonged (aerobic) exercise; blood carries oxygen to the muscles and the heart must pump adequate amounts of blood to meet the demands of aerobic exercise. However, while peak $VO_2$ may be useful as a surrogate for many cardiovascular disease states, it may not be as relevant an endpoint after the Fontan operation. In this unique physiology, central venous pressure, rather than right ventricular contraction (pumping), is the primary driver of transpulmonary blood flow and, therefore, cardiac output. Gewillig M and Goldberg D J. Failure of the fontan circulation. Heart Fail Clin. 10(1):105-116 (January 2014); Egbe A C, Connolly H M, Miranda W R, Ammash N M, Hagler D J, Veldtman G R and Borlaug B A. Hemodynamics of Fontan Failure: The Role of Pulmonary Vascular Disease. Circ Heart Fail. 10(12): e004515 (September 2017); Gewillig M, Brown S C, Eyskens B, Heying R, Ganame J, Budts W, La Gerche A and Gorenflo M. The Fontan circulation: who controls cardiac output? Interact Cardiovasc Thorac Surg. 10(3):428-433 (March 2010); and Goldberg D J, Avitabile C M, McBride M G and Paridon S M. Exercise capacity in the Fontan circulation. Cardiol Young. 23(6): 824-830 (December 2013). As the demand for cardiac output increases with exertion, central venous pressure in the Fontan circulation must rise to meet that demand, but eventually reaches a critical ceiling beyond which it can rise no further. Navaratnam D, Fitzsimmons S, Grocott M, Rossiter H B, Emmanuel Y, Diller G P, Gordon-Walker T, Jack S, Sheron N, Pappachan J, Pratap J N, Vettukattil J J and Veldtman G. Exercise-Induced Systemic Venous Hypertension in the Fontan Circulation. Am J Cardiol. 117(10): 1667-1671 (May 15, 2016). At submaximal exertion, the elevation in central venous pressure does not reach this physiologic ceiling and thus outcomes at this level of exercise may be more sensitive to pharmacologic manipulation of the pulmonary vasculature.

$VO_2$ is often measured by putting a mask on a subject, and measuring the volume and gas concentrations of inhaled and expired air. This measurement is often used in both clinical settings and research and has been considered the most accurate. Testing commonly involves either exercising on a treadmill or riding a cycle ergometer at increasing intensity until exhaustion, and is designed to provide readings at a maximal effort of the subject and/or at the subject's anaerobic threshold.

Patients that have previously undergone a Fontan procedure will generally see a decline in $VO_2$ measurements over time. Treating a patient with methods disclosed herein such that the patient's $VO_2$ measurement is either maintained at a similar level, demonstrating that there has been no further decline in $VO_2$ function, or improved with therapy indicates that the treatment is clinically beneficial and may improve cardiovascular function or prevent or slow the rate of decline in cardiovascular function.

IX. Myocardial Performance Index (MPI)

Generally speaking, MPI (also referred to as the Doppler-derived index or Tei Index) is a measure of ventricular systolic and diastolic function as determined by a focused echocardiogram. It combines systolic and diastolic time intervals to assess heart function. More specifically, MPI can be used to assess ventricular performance represented by a numeric value using cardiac time intervals. This numeric value equals the sum of isovolumetric contraction time (ICT) and isovolumetric relaxation time (IRT) divided by ejection time (ET) and can be determined for either the left or right ventricle. Pellett, A. A., et al.: The Tei Index: Methodology and Disease. State Values. Echocardiography. A Jrnl. of CV Ultrasound & Allied Tech. 21(7):669-672 (2004); and Ulugay, A., Tatli E.: Myocardial performance index. Anadolu Kardiyol Derg 8(2):143-8 (April, 2008), both of which are incorporated herein by reference in their entireties. In the FUEL Trial, the MPI measured the performance of the single functioning ventricle. Thus, the MPI results from the FUEL Trial were determined by velocities obtained from blood pool Doppler assessment of the inflow and outflow tract of the functioning single ventricle. In other words, the FUEL Trial MPI was determined by measuring the cardiac time intervals using pulsed-wave Doppler velocity spectra of the ventricular inflow and outflow of the single functioning ventricle.

X. Echocardiogram Testing

Echocardiograms were performed by sonographers with specific training for this protocol. The primary outcome of interest was MPI using Doppler-based measures of inflow and outflow duration. The duration of inflow into the dominant ventricle and outflow across the dominant semilunar valve were measured and used to calculate MPI using the standard formula. Tei C, Ling L H, Hodge D O, et al.: New index of combined systolic and diastolic myocardial performance: a simple and reproducible measure of cardiac—a study in normals and dilated cardiomyopathy. J Cardiol, 26(6):357-66 (1995); and Pellet A A et al.: The Tei Index Methodology and Disease State Values. Echocardiography: A Jrnl Of CV Ultrasound & Allied Tech, 21(7):669-672

(2004) Additional tissue Doppler images were obtained and used to calculate the tissue Doppler based MPI as previously described. Harada K, Tamura M, Toyono M et al.: Comparison of the right ventricular Tei index by tissue Doppler imaging to that obtained by pulsed Doppler in children without heart disease. *Am J Cardiol*, 90(5):566-9 (2002). Whenever possible, three measurements were made and the mean duration was used for the calculation.

The methods may be further understood with the following non-limiting examples.

Example 1

The Fontan Udenafil Exercise Longitudinal (FUEL) Trial

The FUEL Trial was conducted at 30 centers around the world. The FUEL Trial was a Phase 3, randomized, double-blind, placebo-controlled trial of udenafil in adolescents with SVHD who had undergone Fontan palliation. (Funded by Mezzion Pharma Co. Ltd., and conducted by the National Heart, Lung, and Blood Institute-funded Pediatric Heart Network; ClinicalTrials.gov number NCT02741115).

The primary aim was to determine the effect of udenafil on exercise capacity in adolescents with Fontan physiology over a six-month period. The primary outcome was the change in oxygen consumption at peak exercise (max or peak $VO_2$) from baseline to the 26-week visit. Secondary exercise outcomes included change in additional measures at maximal exertion, as well as change in measures of sub-maximal exercise at the ventilatory anaerobic threshold (VAT). The primary outcome for clinical secondary aims included change in myocardial performance index (MPI), an echocardiographically-derived measure of systolic and diastolic ventricular function, change in log-transformed reactive hyperemia index (lnRHI), a PAT-derived measure of peripheral vascular function, and change in log-transformed serum BNP level. Safety was monitored through adverse event reports, which were collected according to a pre-specified protocol of study coordinator outreach, and through ad hoc patient and family communication with members of the study team at each site.

Trial Population

Individuals between the ages of 12 and 18 years (inclusive) who had undergone the Fontan procedure, who were not receiving treatment with a PDE5 inhibitor, who were ≥40 kg, and who met the minimum height requirement for cycle ergometry (≥132 cm) were eligible for enrollment. To isolate the effect of udenafil on exercise performance, patients with severe ventricular dysfunction, severe atrio-ventricular valve insufficiency, or those with a prior clinical exercise test in which peak oxygen consumption was <50% of predicted for age and gender, were excluded. The full list of inclusion and exclusion criteria are listed in Table 1.

TABLE 1

| FUEL inclusion and exclusion criteria |
| --- |
| Inclusion criteria |
| 1 Males and females with Fontan physiology 12-<19 y of age at enrollment |
| 2 Participant consent or parental/guardian consent with participant assent |
| 3 Participant fluent in English, Spanish, or Korean |
| Exclusion criteria |
| 1 Weight <40 kg |
| 2 Height <132 cm |
| 3 Hospitalization for acute decompensated heart failure within the last 12 m |
| 4 Current intravenous inotropic drugs |
| 5 Undergoing evaluation for heart transplantation or listed for transplantation |
| 6 Diagnosis of active protein-losing enteropathy or plastic bronchitis within the last 3 y, or a history of liver cirrhosis |
| 7 Known Fontan baffle obstruction, branch pulmonary artery stenosis, or pulmonary vein stenosis resulting in a mean gradient of >4 mm Hg between the regions proximal and distal to the obstruction as measured by either catheterization or echocardiography, obtained prior to screening for the trial |
| 8 Single lung physiology with greater than 80% flow to 1 lung |
| 9 $VO_2$ max less than 50% of predicted for age and gender at enrollment |
| 10 Severe ventricular dysfunction assessed qualitatively by clinical echocardiography within 6 m prior to enrollment |
| 11 Severe valve regurgitation, ventricular outflow obstruction, or aortic arch obstruction assessed by clinical echocardiography within 6 m prior to enrollment |
| 12 Significant renal (serum creatinine >2.0), hepatic (serum AST and/or ALT >3 times upper limit of normal), gastrointestinal, or biliary disorders that could impair absorption, metabolism, or excretion of orally administered medications based on laboratory assessment 6 wk prior to screening for the trial |
| 13 Inability to complete exercise testing at baseline screening |
| 14 History of PDE-5 inhibitor use within 3 m before study onset |
| 15 History of any other medication for treatment of pulmonary hypertension within 3 m before study onset |
| 16 Known intolerance to oral udenafil |
| 17 Frequent use of medications or other substances that inhibit or induce CYP3A4 |
| 18 Current use of α-blockers or nitrates |
| 19 Ongoing or planned participation in another research protocol that would either prevent successful completion of planned study testing or invalidate its results |
| 20 Noncardiac medical, psychiatric, and/or social disorder that would prevent successful completion of planned study testing or would invalidate its results |
| 21 Cardiac care, ongoing or planned, at a nonstudy center that would impede study completion |
| 22 For females: pregnancy at the time of screening, pregnancy planned before study completion, or refusal to use an acceptable method of contraception for study duration if sexually active |

TABLE 1-continued

| FUEL inclusion and exclusion criteria |
| --- |

23 Inability to abstain from or limit intake of grapefruit juice during the duration of the trial
24 Refusal to provide written informed consent/assent
25 In the opinion of the primary care physician, the subject is likely to be noncompliant with the study protocol ALT, alanine aminotransferase; AST, aspartate aminotransferase: CYP3A4, cytochrome P450 3A4.

Randomization and Study Procedures

Enrolled participants were assigned to udenafil or placebo in a 1:1 ratio using randomly permuted blocks and stratified by ventricular morphology (left ventricle versus right ventricle or mixed). Randomization assignments were generated by a web-based algorithm after confirmation of trial eligibility and consent.

Baseline clinical testing completed before drug initiation included a blood draw to measure brain-type natriuretic peptide (BNP) level, a cardiopulmonary exercise test (CPET) using a standardized cycle ergometer ramp protocol, a standardized echocardiogram, and an assessment of peripheral vascular function using peripheral arterial tonometry (PAT) measured by finger cuff (EndoPAT; Itamar Medical, Israel). Participants who achieved maximal effort, defined as respiratory exchange ratio (RER)≥1.10 at peak exercise during CPET, were eligible for randomization and study drug initiation. Participants who did not achieve maximal effort were given a subsequent opportunity to repeat the exercise test within two weeks of the initial attempt. End-of-study clinical testing included repeat measurement of serum BNP, CPET, echocardiogram, and PAT.

Statistical Analysis

A sample size of 200 participants per arm was chosen to allow for 90% power to detect a mean treatment difference in change from baseline to 26-week testing in max $VO_2$ of 10% with a type 1 error of 0.05. The following assumption were made: a baseline standard deviation of 7.235 ml/kg/min, a correlation between max $VO_2$ measurements of 0.33, a drop-out and incomplete testing rate of 10%, and failure to reach maximal effort at the 26-week exercise testing in 15% of participants. These assumptions were based on historical data and reflect a conservative approach to assessing within-participant correlations and failure to reach maximal effort. The primary analysis used the intention-to-treat population to evaluate the difference in the change in the primary outcome between treatment arms. This difference was assessed with an analysis of covariance (ANCOVA) with fixed factors for ventricular morphology (single left versus single right or mixed) and treatment group, with a continuous covariate of baseline max $VO_2$. For those without data at the 26-week visit, this value was imputed as equal to the baseline value (no change). Secondary analyses included participants who successfully completed the protocol with measurable values at each of the secondary endpoints. Secondary outcomes of continuous data points were analyzed in the manner described for the primary outcome. In order to assess the generalizability of findings at the ventilatory anaerobic threshold, demographic and clinical characteristics were compared between participants without paired $VO_2$ at VAT data and those comprising the remainder of the cohort.

Trial Results

Figure 1B:
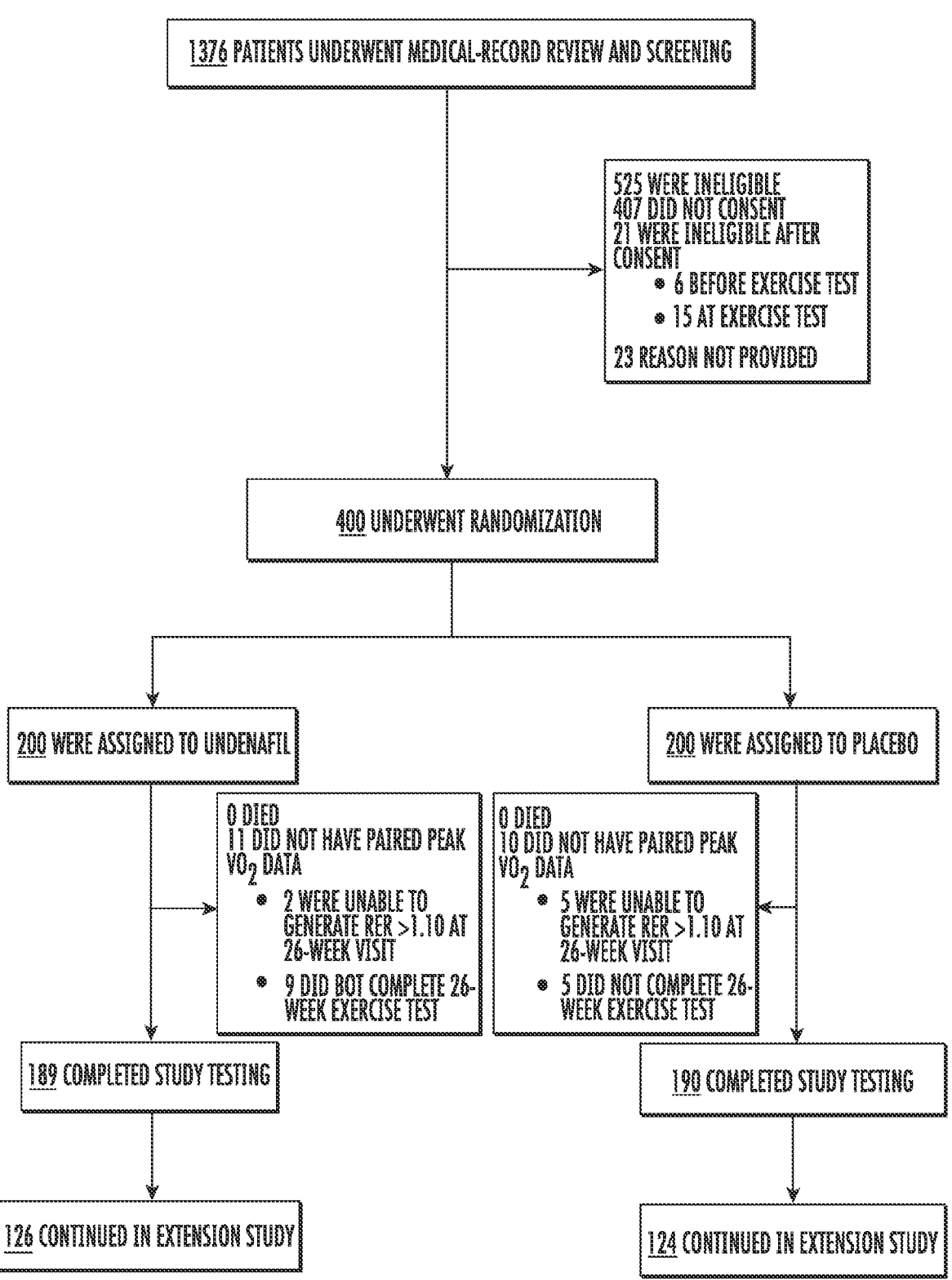
FIG. 1B is a screening process (Randomization and Treatment of the Participants) used for the Fontan Udenafil Exercise Longitudinal (FUEL) Trial as described in the Examples 1-2. Peak $VO_2$ ($VO_2$ max) denotes oxygen consumption at peak exercise. RER denotes respiratory exchange ratio.

From July 2016 to May 2018, 1376 patients at 30 centers were screened. FIG. 1B. Of these, 200 were randomly assigned to udenafil and 200 to placebo. Mean age at randomization was 15.5 years, mean height was 163.6 cm, and mean weight was 58.1 kg. Sixty percent of participants were male and 81% described their racial identity as white. Those in the placebo group were taller, compared to those in the udenafil group, but baseline characteristics were otherwise similar between groups.

Primary Aim—Exercise Measures

Maximal exercise data ($VO_2$ max) were available for all participants at baseline testing, and for 379 participants at 26-week testing (189 in the udenafil group and 190 in the placebo group). Reasons for absence of data at 26-week testing included patient dropout or errors in data capture (n=14), and participant inability to generate an RER≥1.10 (n=7). There was no difference in the change from baseline to 26-week testing in resting heart rate, respiratory rate, or systolic blood pressure between the udenafil and placebo groups. There was a small but statistically significant increase in resting oxygen saturation and a small but statistically significant decrease in diastolic blood pressure in the udenafil group.

Resting data and exercise performance results are provided in Table 2.

TABLE 2

Resting Data and Exercise performance with comparison based on treatment arm. Summaries presented as mean ± standard deviation (n)*.

| | Udenafil | | | Placebo |
| --- | --- | --- | --- | --- |
| | Baseline | 26-week | Change | Baseline |
| Resting data | | | | |
| Heart rate (bpm) | 87.5 ± 15.3 (200) | 86.6 ± 15.4 (191) | −0.9 ± 12.7 (191) | 88.1 ± 14.1 (200) |
| Systolic blood pressure (mmHg) | 112.3 ± 12.1 (200) | 110.5 ± 12.0 (191) | −1.8 ± 12.2 (191) | 113.2 ± 12.9 (200) |
| Diastolic blood pressure (mmHg) | 68.4 ± 9.5 (200) | 65.3 ± 9.9 (191) | −2.9 ± 9.7 (191) | 69.3 ± 10.1 (200) |
| Oxygen saturation (%) | 92.8 ± 3.9 (200) | 93.3 ± 3.5 (191) | 0.5 ± 2.4 (191) | 93.2 ± 3.8 (200) |
| Peak exercise | | | | |
| Oxygen consumption (mL/min)* | 1562 ± 437 (200) | 1606 ± 452 (200) | 44 ± 245 (200) | 1627 ± 414 (200) |
| Work rate (W) | 120 ± 32 (198) | 124 ± 32 (187) | 3.2 ± 14 (186) | 123 ± 32 (199) |

TABLE 2-continued

Resting Data and Exercise performance with comparison based on treatment
arm. Summaries presented as mean ± standard deviation (n)*.

| | | | | |
|---|---|---|---|---|
| Heart rate (bpm) | 165 ± 20 (200) | 165 ± 20 (189) | −1.4 ± 11 (189) | 168 ± 22 (199) |
| Respiratory rate (breaths/min) | 51 ± 11 (199) | 50 ± 12 (188) | −1.1 ± 10 (187) | 51 ± 13 (200) |
| Minute ventilation (L/min) | 71 ± 21 (199) | 73 ± 22 (189) | 1.2 ± 14 (188) | 76 ± 22 (200) |
| Oxygen saturation (%) | 89.2 ± 5.3 (195) | 89.6 ± 4.9 (190) | 0.4 ± 3.4 (186) | 89.8 ± 5.0 (197) |
| Anaerobic Threshold | | | | |
| Oxygen consumption (mL/min) | 1039 ± 301 (170) | 1059 ± 292 (185) | 29.7 ± 177 (170) | 1021 ± 280 (181) |
| Work (W) | 66.2 ± 26 (167) | 69.2 ± 26 (181) | 3.5 ± 15 (167) | 66.1 ± 23 (177) |
| VE/VCO2 | 34.3 ± 4.9 (170) | 33.6 ± 4.8 (185) | −0.76 ± 3.6 (155) | 34.8 ± 5.2 (181) |

| | Placebo | | p |
|---|---|---|---|
| | 26-week | Change | value |
| Resting data | | | |
| Heart rate (bpm) | 87.4 ± 16.1 (195) | −0.6 ± 12.7 (195) | 0.78 |
| Systolic blood pressure (mmHg) | 112.8 ± 11.6 (195) | −0.2 ± 12.2 (195) | 0.18 |
| Diastolic blood pressure (mmHg) | 69.4 ± 9.1 (195) | 0.2 ± 10.7 (195) | 0.003 |
| Oxygen saturation (%) | 92.9 ± 3.7 (195) | −0.3 ± 2.8 (195) | 0.002 |
| Peak exercise | | | |
| Oxygen consumption (mL/min)* | 1623 ± 432 (200) | −3.7 ± 228 (200) | 0.071 |
| Work rate (W) | 127 ± 32 (189) | 2.6 ± 14 (188) | 0.85 |
| Heart rate (bpm) | 166 ± 21 (190) | −2.5 ± 13 (189) | 0.56 |
| Respiratory rate (breaths/min) | 50 ± 12 (189) | −1.5 ± 10 (189) | 0.72 |
| Minute ventilation (L/min) | 76 ± 21 (190) | −0.1 ± 14 (190) | 0.84 |
| Oxygen saturation (%) | 89.7 ± 5.0 (192) | −0.1 ± 3.4 (190) | 0.21 |
| Anaerobic Threshold | | | |
| Oxygen consumption (mL/min) | 1014 ± 277 (191) | −8.0 ± 183 (181) | 0.023 |
| Work (W) | 66.6 ± 23 (186) | 0.31 ± 13.3 (177) | 0.029 |
| VE/VCO2 | 34.7 ± 4.9 (191) | −0.06 ± 3.1 (162) | 0.011 |

*P-value was assessed using ANCOVA with fixed factors for ventricular morphology (single left versus single right or mixed) and treatement group with a continuous covariate of baseline maximal VO2.
Note:
Last observation carried forward was used to impute missing values at Week 26.

Analysis at resting of the diastolic blood pressure demonstrated a statistically significant change (a decrease shows improvement) in diastolic blood pressure in the udenafil group (−2.9 decrease, improvement) compared to the placebo group (+0.2 increase, no improvement) (p=0.003).

Analysis at resting of the oxygen saturation (%) demonstrated a statistically significant change (an increase shows improvement) in oxygen saturation (%) in the udenafil group (+0.5 increase, improvement) compared to the placebo group (−0.3 decrease, no improvement) (p=0.002).

Analysis at maximal exercise demonstrated an increase in $VO_2$ max of 44 mL/min (2.8%) in the udenafil group compared to a decline of 3.7 mL/min (−0.2%) in the placebo group, although the difference did not reach statistical significance (p=0.071).

Further, metabolic data for the calculation of $VO_2$ at VAT were available for 317 participants; 170 in the udenafil group and 181 in the placebo group, as shown in Table 2 above. There was no difference in the baseline demographic or clinical characteristics of this subgroup compared to the larger cohort. For those with paired $VO_2$ at VAT data, there was a statistically significant improvement of 30 mL/min (1.92%) in the udenafil group compared to a decrease of 8 mL/min (−0.7%) in the placebo group (p=0.023). Ventilatory equivalents of carbon dioxide measured at VAT (VE/$VCO_2$) significantly decreased (improved ventilatory efficiency) by 0.8 (2.1%) in the udenafil group compared to 0.05

(0.2%) in the placebo group (p=0.011), while the work rate significantly improved by 3.5 Watts (5.5%) in the udenafil group compared to 0.31 Watts (0.78%) in the placebo group (p=0.029). Thus, treatment of Fontan patients with 87.5 mg, twice daily, demonstrated statistically significant improvements in multiple measures of exercise performance at the ventilatory anaerobic threshold.

Secondary Aims Measures

Paired echocardiographic data for the measure of MPI were available in 250 participants (63%); 122 in the udenafil group and 128 in the placebo group. Table 3. There was a statistically significant change (a decrease shows improvement) in MPI in the udenafil treated group (−0.02 decrease, improvement) as compared to the placebo group +0.01 increase, no improvement) (p=0.028).

Paired PAT-derived vascular function data were available in 328 participants (81%); 163 in the udenafil group and 165 in the placebo group. There were non-significant improvements in lnRHI in both the udenafil and placebo groups (0.07 vs 0.05, p=0.59). Paired measures of serum BNP level were available in 378 participants (95%); 187 in the udenafil group and 191 in the placebo group. The change in log serum BNP level was not different between groups (p=0.18). The paired echocardiographic data, the paired PAT-derived vascular function data, and the paired measure of serum BNP level is provided in Table 3.

TABLE 3

| Secondary Outcomes with Comparison Based on Treatment Arm | | | | |
|---|---|---|---|---|
| Endocardiography Myocardial Performance Index (MPI) by Visit and Treatment Arm Difference Between Week 26 and Baseline Visits (ITT Population) | Udenafil | Placebo | LS Mean Dif A − B(SE)*** | P-Value |
| Baseline, N: Mean (SD) | 150: 0.45 (0.173) | 155: 0.45 (0.156) | −0.0 (0.018) | 0.818* |
| Week 26, N: Mean (SD) | 146: 0.42 (0.147) | 148: 0.46 (0.177) | −0.04 (0.018) | 0.024* |
| Difference, Week 26 − Baseline N: Mean (SD) | 122: −0.02 (0.113) | 128: 0.01 (0.133) | −0.03 (0.014) | 0.028** |
| Median (Interquartile Range) of the difference | −0.01 (−0.11, 0.05) | 0.01 (−0.08, 0.08) | | |
| Min, Max of the difference | (−.3, 0.2) | (−0.5, 0.4) | | |

*P value was assessed using ANOVA with the fixed factors for ventricular morphology (single left versus single right or mixed) and treatment group
**P value was assessed using ANCOVA with fixed factors for ventricular morphology (single left versus single right or mixed) and treatment group with a continuous covariate of baseline maximal $VO_2$
***LS Mean (least square mean) was the estimated treatment mean difference from the analysis model

| Endpoint | Udenafil (N = 200) | Placebo (N = 200) | Difference LS Mean (SE) | p-value[a] |
|---|---|---|---|---|
| Log-transformed reactive hyperemia index | n = 170 | n = 173 | | |
| Difference, Week 26 − baseline, mean (SD) | 0.06 (0.301) | 0.04 (0.370) | 0.02 (0.030) | 0.591 |
| Log brain natriuretic peptide (pg/mL) | n = 187 | n = 191 | | |
| Difference, Week 26 − baseline, mean (SD) | 0.08 (0.905) | 0.03 (1.137) | 0.13 (0.094) | 0.169 |

ANCOVA = analysis of covariance;
ITT = intent-to-treat;
LS = least squares;
SD = standard deviation;
SE = standard error
[a]P-value was assessed using ANCOVA with fixed factors for ventricular morphology (single left versus single right or mixed) and treatment group with a continuous covariate of baseline maximal minute oxygen consumption.
Note:
Brain natriuretic peptide values reported by the laboratory as <2.0 were imputed as 1.0.

Safety and Tolerability

TABLE 4

| Non-Serious Adverse Events. Number of participants that experienced an adverse event presented as n (%). | | |
|---|---|---|
| | Udenafil (200) | Placebo (200) |
| Headache | 79 (39.5) | 51 (25.5) |
| Flushing | 32 (16.0) | 12 (6.0) |
| Dizziness | 16 (8.0) | 17 (8.5) |
| Nausea/vomiting | 31 (15.5) | 14 (7.0) |
| Increased erection* | 13 (11.7) | 2 (1.6) |
| Epistaxis | 21 (10.5) | 5 (2.5) |

*Percentage of male participants.

Udenafil and placebo were well tolerated by study participants. There were no deaths in the study cohort. A total of 24 participants (6%) experienced a serious adverse event; 14 in the udenafil group and 10 in the placebo group. There were 3 events in the udenafil group and 2 events in the placebo group that were thought to have a possible, probable, or definite relationship to study drug. Those that occurred in the udenafil group included unilateral retinal artery and vein thrombosis, transient lower extremity diplegia, and transient dyspnea. Frequent non-serious adverse events thought to have a possible, probable, or definite relationship to study drug that occurred in at least 5% of participants in either treatment group are provided in Table 4. Headache, facial flushing, abdominal pain, epistaxis, and erection (male participants) were more common in the udenafil group. All other adverse events occurred with similar frequency between the groups.

Example 2

Additional FUEL Trial Results

The following example additionally describes the above-referenced FUEL trial, as referenced in Goldberg, D J, et al.: Results of the Fontan Udenafil Exercise Longitudinal (FUEL) Trial. *Circulation*, 141(8):141:641-651 (2020), which is hereby incorporated herein by reference in its entirety.

The Fontan operation creates a total cavopulmonary connection, a circulation in which the importance of pulmonary vascular resistance is magnified. Over time, this circulation leads to deterioration of cardiovascular efficiency associated with a decline in exercise performance. Rigorous clinical trials aimed at improving physiology and guiding pharmacotherapy are lacking.

The FUEL Trial was a Phase III clinical trial conducted at 30 centers. Participants were randomly assigned udenafil, 87.5 mg twice daily, or placebo in a 1:1 ratio. The primary outcome was the between group difference in change in oxygen consumption at peak exercise. Secondary outcomes included between group differences in changes in submaximal exercise at the ventilatory anaerobic threshold (VAT), the myocardial performance index (MPI), the natural log of the reactive hyperemia index (lnRHI), and serum brain-type natriuretic peptide (BNP).

Between 2017 and 2019, 30 clinical sites in North America and the Republic of Korea randomized 400 participants with Fontan physiology. The mean age at randomization was 15.5±2 years; 60% of participants were male and 81% were White. All 400 subjects were included in the primary analysis with imputation of the 26-week endpoint for 21 participants with missing data (11 randomized to udenafil and 10 to placebo). Among randomized participants, peak oxygen consumption increased by 44±245 mL/min (2.8%) in the udenafil group and declined by 3.7±228 mL/min (−0.2%) in the placebo group (p=0.071). Analysis at VAT demonstrated statistically significant improvements in the udenafil group versus the placebo group in oxygen consumption (+33±185 (3.2%) vs −9±193 (−0.9%) mL/min, p=0.012), ventilatory equivalents of carbon dioxide (−0.8 vs −0.06, p=0.014), and work rate (+3.8 vs +0.34 Watts, p=0.021). Analysis of MPI also demonstrated statistically significant improvement in the udenafil treated group (p=0.028) compared to the group taking placebo over the same time period. There was no difference in change in lnRHI, or serum BNP level.

In the FUEL trial, treatment with udenafil (87.5 mg twice daily) was associated with an improvement in oxygen consumption at peak exercise (p=0.071) and statistically significant improvements in (i) multiple measures of exercise performance at the ventilatory anaerobic threshold (VAT), (ii) MPI, (iii) diastolic blood pressure at rest, and (iv) oxygen saturation (%) at rest.

The FUEL trial was Funded by Mezzion Pharma Co. Ltd., and conducted by the National Heart, Lung, and Blood Institute-funded Pediatric Heart Network. ClinicalTrials.gov number NCT02741115, which is hereby incorporated herein by reference in its entirety.

Clinical Perspective

New Aspects

The Circulation publication describes the results of the Fontan Udenafil Exercise Longitudinal (FUEL) Trial, the largest medical intervention trial in congenital heart disease. Goldberg D. J. et al.: Results of the FUEL Trial. *Circulation,* 141(8):141:641-651 (2020)

The Circulation errata to Goldberg D. J. et al.: Results of the FUEL Trial. *Circulation,* 141(8):141:641-651 (2020), as incorporated in Example 4, describes the corrected MPI results of the FUEL Trial.

While treatment with udenafil did not result in a statistically significant increase in peak oxygen consumption, it did result in a notable increase in peak oxygen consumption.

Treatment with udenafil did result in statistically significant improvements in measures of exercise performance at the ventilator anaerobic threshold (VAT), work rate at VAT, ventilatory equivalents of carbon dioxide (VE/VCO$_2$) at VAT, MPI, diastolic blood pressure at rest, and oxygen saturation at rest.

Udenafil was well tolerated by the FUEL Trial subjects with side effects limited to those previously known to be associated with phosphodiesterase type 5 inhibitors.

Clinical Implications

Udenafil is the first medication evaluated in a large-scale, phase III clinical trial to demonstrate a quantifiable benefit in measures of exercise capacity in adolescents after Fontan palliation.

These findings suggest that therapy with udenafil may improve the physiology, the exercise capacity, the work rate, the VE/VCO$_2$, the MP, the cardiac output, the squeezing performance, the amount of flow that can circulate through the body in a given amount of time, diastolic blood pressure and/or oxygen saturation at rest, and the performance of the single functioning ventricles of the cohort of patients who have undergone a total cavopulmonary connection.

Ongoing surveillance is needed to determine the effect of chronic treatment with udenafil on the long-term clinical course of those living with single ventricle congenital heart disease.

Children born with single ventricle congenital heart disease (SVHD) require a series of staged surgical interventions to reconstruct their defective hearts for long-term survival. The Fontan operation, the final planned palliative procedure in this series of staged surgical interventions to reconstruct the heart, separates the systemic and pulmonary circulations by creating a total cavopulmonary connection. Fontan F and Baudet E. Surgical repair of tricuspid atresia. Thorax. 26(3):240-248 (May 1971); and Kreutzer G, Galindez E, Bono H, De Palma C and Laura J P. An operation for the correction of tricuspid atresia. The Journal of thoracic and cardiovascular surgery. 66(4):613-621 (October 1973).

In the absence of a sub-pulmonary pump, however, the resultant Fontan circulation is characterized by passive pulmonary blood flow, chronically elevated central venous pressure, and low cardiac output. Gewillig M and Goldberg D J. Failure of the fontan circulation. Heart Fail Clin. 10(1):105-116 (January 2014); Egbe A C, Connolly H M, Miranda W R, Ammash N M, Hagler D J, Veldtman G R and Borlaug B A. Hemodynamics of Fontan Failure: The Role of Pulmonary Vascular Disease. Circ Heart Fail. 10(12): e004515 (September 2017); Gewillig M, Brown S C, Eyskens B, Heying R, Ganame J, Budts W, La Gerche A and Gorenflo M. The Fontan circulation: who controls cardiac output? Interact Cardiovasc Thorac Surg. 10(3):428-433 (March 2010); and Goldberg D J, Avitabile C M, McBride M G and Paridon S M. Exercise capacity in the Fontan circulation. Cardiol Young. 23(6):824-830 (December 2013). Although Fontan physiology is often well tolerated during childhood, cardiovascular efficiency deteriorates through adolescence and into adulthood. Dennis M, Zannino D, du Plessis K, Bullock A, Disney P J S, Radford D J, Hornung T, Grigg L, Cordina R, d'Udekem Y and Celermajer D S. Clinical Outcomes in Adolescents and Adults After the Fontan Procedure. *J Am Coll Cardiol.* 71(9):1009-1017 (March 6 2018); Fernandes S M, McElhinney D B, Khairy P, Graham D A, Landzberg M J and Rhodes J. Serial cardiopulmonary exercise testing in patients with previous Fontan surgery. *Pediatr Cardiol.* 31(2):175-180 (February 2010); Giardini A, Hager A, Pace Napoleone C and Picchio F M. Natural history of exercise capacity after the Fontan operation: a longitudinal study. *Ann Thorac Surg.* 85(3):818-21 (March 2008); Jenkins P C, Chinnock R E, Jenkins K J, Mahle W T, Mulla N, Sharkey A M and Flanagan M F. Decreased exercise performance with age in children with hypoplastic left heart syndrome. *J Pediatr.* 152(4):507-512 (April 2008); Paridon S M, Mitchell P D, Colan S D, Williams R V, Blaufox A, Li J S, Margossian R, Mital S, Russell J, Rhodes J and Pediatric Heart Network I. A cross-sectional study of exercise performance during the first 2 decades of life after the Fontan operation. *J Am Coll Cardiol.* 52(2):99-107 (Jul. 8, 2008); and Atz A M, Zak V, Mahony L, Uzark K, D'Agincourt N, Goldberg D J, Williams R V, Breitbart R E, Colan S D, Burns K M, Margossian R, Henderson H T, Korsin R, Marino B S, Daniels K, McCrindle B W and Pediatric Heart Network I. Longitudinal Outcomes of Patients With Single Ventricle After the Fontan Procedure. *J Am Coll Cardiol.* 69(22):2735-2744 (Jun. 6, 2017). This deterioration correlates with a decline in exercise capacity, global cardiac performance, single ventricular performance and an increase in the prevalence of heart failure symptoms, hospitalizations, and mortality. Diller G P, Dimopoulos K, Okonko D, Li W, Babu-Narayan S V, Broberg C S, Johansson B, Bouzas B, Mullen M J, Poole-Wilson P A, Francis D P and Gatzoulis M A. Exercise intolerance in adult congenital heart disease: comparative severity, correlates, and prognostic implication. *Circulation.* 112(6):828-35 (Aug. 9, 2005); Diller G P, Giardini A, Dimopoulos K, Gargiulo G, Muller J, Derrick G, Giannak-oulas G, Khambadkone S, Lammers A E, Picchio F M, Gatzoulis M A and Hager A. Predictors of morbidity and mortality in contemporary Fontan patients: results from a multicenter study including cardiopulmonary exercise testing in 321 patients. *Eur Heart J.* 31(24):3073-3083 (December 2010); Downing T E, Allen K Y, Glatz A C, Rogers L S, Ravishankar C, Rychik J, Faerber J A, Fuller S, Montenegro L M, Steven J M, Spray T L, Nicolson S C, Gaynor J W and Goldberg D J. Long-term survival after the Fontan operation: Twenty years of experience at a single center. *The Journal of thoracic and cardiovascular surgery.* 154(1):243-253 e2 (July 2017); Khairy P, Fernandes S M, Mayer J E, Jr., Triedman J K, Walsh E P, Lock J E and Landzberg M J. Long-term survival, modes of death, and predictors of mortality in patients with Fontan surgery. *Circulation.* 117 (1):85-92 (Jan. 1, 2008); Pundi K N, Johnson J N, Dearani J A, Pundi K N, Li Z, Hinck C A, Dahl S H, Cannon B C, O'Leary P W, Driscoll D J and Cetta F. 40-Year Follow-Up After the Fontan Operation: Long-Term Outcomes of 1,052 Patients. *J Am Coll Cardiol.* 66(15):1700-1710 (Oct. 13, 2015); Cunningham J W, Nathan A S, Rhodes J, Shafer K, Landzberg M J and Opotowsky A R. Decline in peak oxygen consumption over time predicts death or transplantation in adults with a Fontan circulation. *Am Heart J.* 189:184-192 (July 2017); and Udholm S, Aldweib N, Hjortdal V E and Veldtman G R. Prognostic power of cardiopulmonary exercise testing in Fontan patients: a systematic review. *Open Heart.* 5(1):e000812 (July 2018).

After the Fontan operation, pulmonary blood flow is dependent on the relationship between central venous pressure, pulmonary vascular resistance, and systemic atrial pressure. In this construct, the role of pulmonary vascular resistance as a modulator of pulmonary blood flow and single ventricular preload is magnified and critical to circulatory efficiency. Gewillig M and Goldberg D J. Failure of the fontan circulation. Heart Fail Clin. 10(1):105-116 (January 2014); Egbe A C, Connolly H M, Miranda W R, Ammash N M, Hagler D J, Veldtman G R and Borlaug B A. Hemodynamics of Fontan Failure: The Role of Pulmonary Vascular Disease. Circ Heart Fail. 10(12): e004515 (September 2017); Gewillig M, Brown S C, Eyskens B, Heying R, Ganame J, Budts W, La Gerche A and Gorenflo M. The Fontan circulation: who controls cardiac output? Interact Cardiovasc Thorac Surg. 10(3):428-433 (March 2010); and Goldberg D J, Avitabile C M, McBride M G and Paridon S M. Exercise capacity in the Fontan circulation. Cardiol Young. 23(6):824-830 (December 2013). Prior reports have explored the administration of pulmonary vasodilators, including phosphodiesterase type 5 (PDE5) inhibitors, with mixed results. Agnoletti G, Gala S, Ferroni F, Bordese R, Appendini L, Pace Napoleone C and Bergamasco L. Endothelin inhibitors lower pulmonary vascular resistance and improve functional capacity in patients with Fontan circulation. The Journal of thoracic and cardiovascular surgery. 153(6):1468-1475 (June 2017); Goldberg D J, French B, McBride M G, Marino B S, Mirarchi N, Hanna B D, Wernovsky G, Paridon S M and Rychik J. Impact of oral sildenafil on exercise performance in children and young adults after the fontan operation: a randomized, double-blind, placebo-controlled, crossover trial. *Circulation.* 123 (11):1185-1193 (May 22, 2011); Hebert A, Mikkelsen U R, Thilen U, Idorn L, Jensen A S, Nagy E, Hanseus K, Sorensen K E and Sondergaard L. Bosentan improves exercise capacity in adolescents and adults after Fontan operation: the TEMPO (Treatment With Endothelin Receptor Antagonist in Fontan Patients, a Randomized, Placebo-Controlled, Double-Blind Study Measuring Peak Oxygen Consumption) study. *Circulation.* 130(23):2021-2030 (Dec. 2, 2014); Mori H, Park I S, Yamagishi H, Nakamura M, Ishikawa S, Takigiku K, Yasukochi S, Nakayama T, Saji T and Nakanishi T. Sildenafil reduces pulmonary vascular resistance in single ventricular physiology. *Int J Cardiol.* 221:122-127 (Oct. 15, 2016); Rhodes J, Ubeda-Tikkanen A, Clair M, Fernandes S M, Graham D A, Milliren C E, Daly K P, Mullen M P and Landzberg M J. Effect of inhaled iloprost on the exercise function of Fontan patients: a demonstration of concept. *Int J Cardiol.* 168(3):2435-2440 (Oct. 3, 2013); Schuuring M J, Vis J C, van Dijk A P, van Melle J P, Vliegen H W, Pieper P G, Sieswerda G T, de Bruin-Bon RH, Mulder B J and Bouma B J. Impact of bosentan on exercise capacity in adults after the Fontan procedure: a randomized controlled trial. *Eur J Heart Fail.* 15(6):690-698 (June 2013); Tunks R D, Barker P C, Benjamin D K, Jr., Cohen-Wolkowiez M, Fleming G A, Laughon M, Li J S and Hill K D. Sildenafil exposure and hemodynamic effect after Fontan surgery. *Pediatr Crit Care Med.* 15(1):28-34 (January 2014); Van De Bruaene A, La Gerche A, Claessen G, De Meester P, Devroe S, Gillijns H, Bogaert J, Claus P, Heidbuchel H, Gewillig M and Budts W. Sildenafil improves exercise hemodynamics in Fontan patients. *Circ Cardiovasc Imaging.* 7(2):265-273 (March 2014); Goldberg D J, French B, Szwast A L, McBride M G, Marino B S, Mirarchi N, Hanna B D, Wernovsky G, Paridon S M and Rychik J. Impact of sildenafil on echocardiographic indices of myocardial performance after the Fontan operation. *Pediatr Cardiol.* 33(5): 689-696 (June 2012); and Giardini A, Balducci A, Specchia S, Gargiulo G, Bonvicini M and Picchio F M. Effect of sildenafil on haemodynamic response to exercise and exercise capacity in Fontan patients. *Eur Heart J.* 29(13):1681-1687 (July 2008).

A phase I/II study of udenafil (Mezzion Pharma Co. Ltd., Seoul, Republic of Korea), a long-acting PDE5 inhibitor, was previously completed in adolescents with Fontan physiology and demonstrated tolerability at all tested dosing regimens. Goldberg D J, Zak V, Goldstein B H, Chen S, Hamstra M S, Radojewski E A, Maunsell E, Mital S, Menon S C, Schumacher K R, Payne R M, Stylianou M, Kaltman J R, deVries T M, Yeager J L, Paridon S M and Pediatric Heart Network I. Results of a phase I/II multi-center investigation of udenafil in adolescents after fontan palliation. *Am Heart J.* 188:42-52 (June 2017). A dose of 87.5 mg twice daily was associated with the highest average serum concentration and was not associated with dose-limiting adverse events. In the Pediatric Heart Network's (PHN) Fontan Udenafil Exercise Longitudinal (FUEL) trial (NCT02741115), we evaluated the effect of udenafil on exercise performance and other cardiovascular and functional outcomes over a six-month period in adolescents who have undergone Fontan palliation.

Methods

The FUEL trial was an international, multicenter, randomized, double-blind, placebo-controlled trial of udenafil, in addition to standard care, in adolescents with SVHD who had undergone Fontan palliation. The trial was supported by the National Heart, Lung, and Blood Institute (NHLBI)-funded PHN in partnership with the regulatory sponsor, Mezzion Pharma Co. Ltd., 5 under a Special Protocol Assessment through the Food and Drug Administration. The FUEL protocol and consent forms and all subsequent amendments were approved by the DSMB, the institution review board or equivalent at each study center, and regulatory agencies from the United States, Canada, and the Republic of Korea. Consent was obtained from the study participant, or the legal guardian for those <18 years of age. Assent was obtained from participants >18 years of age. The trial design has been published previously. Goldberg D J, Zak V, Goldstein B H, McCrindle B W, Menon S C, Schumacher K R, Payne R M, Rhodes J, McHugh K E, Penny D J, Trachtenberg F, Hamstra M S, Richmond M E, Frommelt P C, Files M D, Yeager J L, Pemberton V L, Stylianou M P, Pearson G D, Paridon S M and Pediatric Heart Network I. Design and rationale of the Fontan Udenafil Exercise Longitudinal (FUEL) trial. *Am Heart J.* 201: 1-8 (July 2018).

Trial Population

Individuals between the ages of 12 and 18 years (inclusive) who had undergone the Fontan procedure, who were not receiving treatment with a PDE5 inhibitor, who were ≥40 kg, and who met the minimum height requirement for cycle ergometry (≥132 cm) were eligible for enrollment. To isolate the effect of udenafil on exercise performance, patients with severe ventricular dysfunction, severe atrioventricular valve insufficiency, or those with a prior clinical exercise test in which peak oxygen consumption was <50% of predicted for age and sex, were excluded. The full list of inclusion and exclusion criteria are listed in Table 1 above for the study protocol.

Randomization and Study Procedures

Enrolled participants were assigned to udenafil or placebo in a 1:1 ratio in a double-blind manner using randomly permuted blocks and stratified by ventricular morphology (left ventricle versus right ventricle or mixed). Randomization assignments were generated by a web-based algorithm after confirmation of trial eligibility and consent.

Baseline clinical testing completed before drug initiation included a blood draw to measure brain-type natriuretic peptide (BNP) level, a cardiopulmonary exercise test (CPET) using a standardized cycle ergometer ramp protocol (previously described in children and adolescents with Fontan physiology, Sleeper L A, Anderson P, Hsu D T, Mahony L, McCrindle B W, Roth S J, Saul J P, Williams R V, Geva T, Colan S D, Clark B J and Pediatric Heart Network I. Design of a large cross-sectional study to facilitate future clinical trials in children with the Fontan palliation. *Am Heart J.* 152(3):427-433 (September 2006), a standardized echocardiogram, and an assessment of peripheral vascular function using peripheral arterial tonometry (PAT) measured by finger cuff (EndoPAT; Itamar Medical, Israel). Participants who achieved maximal effort, defined as respiratory exchange ratio (RER)≥1.10 at peak exercise during CPET, were eligible for randomization and study drug initiation. Participants who did not achieve maximal effort were given a subsequent opportunity to repeat the exercise test within two weeks of the initial attempt. End-of-study clinical testing included repeat measurement of serum BNP, CPET, echocardiogram, and PAT.

Primary and Secondary End Points

The primary aim was to determine the effect of udenafil on exercise capacity in adolescents with Fontan physiology over a six-month period. The primary outcome was the between group difference in the change in oxygen consumption at peak exercise (peak $VO_2$) from baseline to the 26-week visit. Secondary exercise outcomes included between group differences in change in additional measures at maximal exertion, as well as change in measures of submaximal exercise at the ventilatory anaerobic threshold (VAT). All measurement of values for exercise testing were initially made by the exercise physiologists and physicians at the individual participating sites. These were subsequently reviewed for accuracy in a blinded fashion at each site by one of two trained reviewers (MGM, SMP) in conjunction with the sites' exercise teams prior to finalization. For both peak $VO_2$ and $VO_2$ at VAT, unindexed oxygen consumption was evaluated to avoid the introduction of confounding based on short-term change in body habits. An analysis of oxygen consumption corrected for body weight is included in Table 5.

TABLE 5

| Oxygen consumption indexed to weight for peak exercise and the anaerobic threshold with comparison based on treatment arm. Summaries presented as mean ± standard deviation (n). | | | |
|---|---|---|---|
| | | Peak exercise Oxygen consumption (mL/kg/min) | Anaerobic Threshold Oxygen consumption (mL/kg/min) |
| Udenafil | Baseline | 27.84 ± 6.88 (200) | 18.35 ± 4.63 (170) |
| | 26-week | 27.61 ± 6.87 (200) | 18.20 ± 4.51 (185) |
| | Change | −0.23 ± 4.06 (200) | −0.07 ± 3.0 (170) |
| Placebo | Baseline | 28.01 ± 6.13 (200) | 17.71 ± 4.30 (181) |
| | 26-week | 27.12 ± 6.63 (200) | 16.99 ± 4.13 (191) |
| | Change | −0.89 ± 3.67 (200) | −0.68 ± 3.2 (181) |
| | p value | 0.092** | 0.012** |

**P_value was assessed using ANCOVA with fixed factors for ventricular morphology (single left versus single right or mixed) and treatment group with a continuous covariate of baseline maximal VO2.
Imputations were done as follows:
Subjects who were known to be alive, but who discontinued from the study (and were missing maximal VO2 at Week 26) were assigned the latest value available (e.g., value from end of study visit if available and from baseline visit otherwise).
Subjects who completed Week 26, but were physically unable to reach maximum effort in cardiopulmonary exercise testing after two attempts, were assigned their baseline value when the subject met maximum effort in Baseline exercise testing. One exception was subject 330011 who was adjudicated to be included as RER was 1.10

The primary outcome for clinical secondary aims included the between group differences in change in myocardial performance index (MPI), an echocardiographically-derived measure of systolic and diastolic ventricular function, change in log-transformed reactive hyperemia index (lnRHI), a PAT-derived measure of peripheral vascular function, and change in log-transformed serum BNP level. Measurements for each of these secondary outcomes were performed at core labs. Safety was monitored through adverse event reports, which were collected according to a pre-specified protocol of study coordinator outreach, and through adhoc patient and family communication with members of the study team at each site.

Statistical Analysis

A sample size of 200 participants per arm was chosen to allow for 90% power to detect a mean treatment difference in change from baseline to 26-week testing in peak $VO_2$ of 10% with a type 1 error of 0.05. We assumed a baseline standard deviation of 7.235 ml/kg/min, a correlation between peak $VO_2$ measurements of 0.33, a drop-out and incomplete testing rate of 10%, and failure to reach maximal effort at the 26-week exercise testing in 15% of participants. These assumptions were based on historical data and reflect a conservative approach to assessing within-participant correlations and failure to reach maximal effort and the analysis was performed using a two-sample, independent means t-test. The primary analysis used the intention-to-treat population to evaluate the difference in the change in the primary outcome between treatment arms. This difference was assessed with an analysis of covariance (ANCOVA) with fixed factors for ventricular morphology (single left versus single right or mixed) and treatment group, with a continuous covariate of baseline peak $VO_2$. For those without data at the 26-week visit, this value was imputed as equal to the baseline value (no change). The alpha level was set at 0.05 with two-sided testing. All statistical analyses were performed using SAS statistical software 9.4 (SAS Institute, Inc., Cary, North Carolina). Secondary analyses included participants who successfully completed the protocol with measurable values at each of the secondary endpoints. Secondary outcomes of continuous data points were analyzed in the manner described for the primary outcome. In order to assess the generalizability of findings at the ventilatory anaerobic threshold, demographic and clinical characteristics were compared between participants without paired $VO_2$ at VAT data and those comprising the remainder of the cohort using the Student's t-test and Fisher's exact test. Fisher's exact test was used to compare adverse events between the udenafil and placebo cohorts.

Results

Participants: From July 2016 to May 2018, 1376 patients at 30 centers were screened. FIG. 1B. Of these, 200 were randomly assigned to udenafil and 200 to placebo. Mean age at randomization was 15.5 years, mean height was 163.6 cm, and mean weight was 58.1 kg. Sixty percent of participants were male and 81% described their racial identity as white. Those in the placebo group were taller, compared to those in the udenafil group, but baseline characteristics were otherwise similar between groups in Table 6.

TABLE 6

Demographic and clinical baseline characteristics for the 400 subjects randomized to a treatment arm; summaries presented as mean (standard deviation) unless otherwise noted as n (%).

| | Total (n = 400) | Udenafil (n = 200) | Placebo (n = 200) |
|---|---|---|---|
| Age, years | 15.5 (2.0) | 15.4 (2.0) | 15.6 (2.0) |
| Female, n (%) | 161 (40.3) | 89 (44.5) | 72 (36.0) |
| Race, n (%) | | | |
| White | 324 (81.0) | 169 (84.5) | 155 (77.5) |
| Asian | 38 (9.5) | 17 (8.5) | 21 (10.5) |
| Black | 23 (5.8) | 10 (5.0) | 13 (6.5) |
| Other | 15 (3.8) | 4 (2.0) | 11 (5.5) |
| Predominant Ventricular morphology, n (%) | | | |
| Right | 176 (44.0) | 89 (44.5) | 87 (43.5) |
| Left | 189 (47.3) | 94 (47.0) | 95 (47.5) |

TABLE 7

Demographic and clinical baseline characteristics for subjects with versus without paired data for $VO_2$ at VAT; summaries presented as mean (standard deviation) unless otherwise noted as n (%).

| | Total (n = 400) | Paired Data (n = 317) | No Paired Data (n = 83) | p value* |
|---|---|---|---|---|
| Age, years | 15.5 (2.0) | 15.6 (2.0) | 15.4 (2.2) | 0.50 |
| Female, n (%) | 161 (40.3%) | 128 (40.4%) | 33 (39.8%) | 1.0 |
| Race, n (%) | | | | 0.16 |
| White | 324 (81.0%) | 256 (80.8%) | 68 (81.9%) | |
| Asian | 38 (9.5%) | 34 (10.7%) | 4 (4.8%) | |
| Black | 23 (5.8%) | 15 (4.7%) | 8 (9.6%) | |
| Other | 15 (3.8%) | 12 (3.8%) | 3 (3.6%) | |

TABLE 6-continued

Demographic and clinical baseline characteristics for the 400 subjects randomized to a treatment arm; summaries presented as mean (standard deviation) unless otherwise noted as n (%).

| | Total (n = 400) | Udenafil (n = 200) | Placebo (n = 200) |
|---|---|---|---|
| Other (indeterminant and biventricular) | 35 (8.8) | 17 (8.5) | 18 (9.0) |
| Subjects with a patent fenestration, n (%) | 131 (32.8) | 73 (36.5) | 58 (29.0) |
| Height, cm | 163.6 (9.6) | 162.5 (10.4) | 164.7 (8.7) |
| Weight, kg | 58.1 (13.6) | 57.1 (13.9) | 59.0 (13.2) |
| Body mass index, kg/m² | 21.6 (4.1) | 21.5 (3.9) | 21.7 (4.2) |

*t-test for continuous variables, Fisher exact test for categorical

Exercise Measures

Figure 2A:
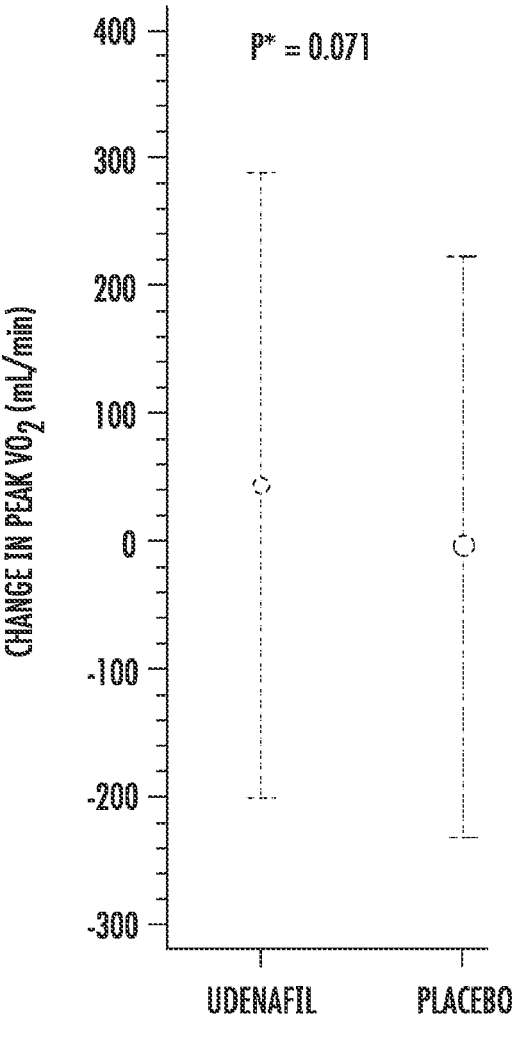
FIG. 2A demonstrates the difference in the change in mean peak or max $VO_2$ from Baseline to Week 26 along with the standard deviation for each treatment arm.
Figure 2B:
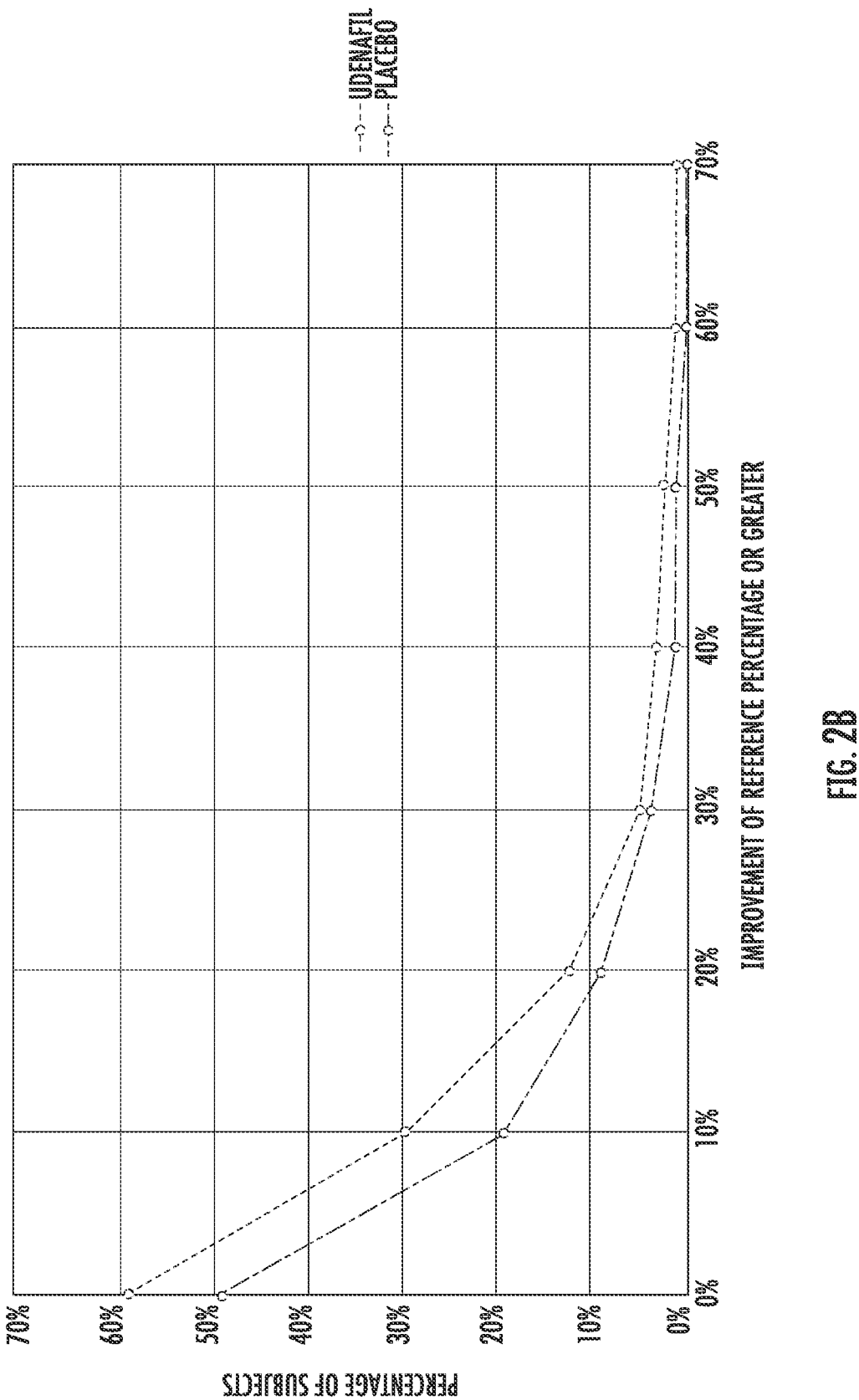
FIG. 2B demonstrates the percentage of subjects (y axis) who demonstrated improvement in peak $VO_2$ by the reference percentage or greater (x axis)
Figure 3A:
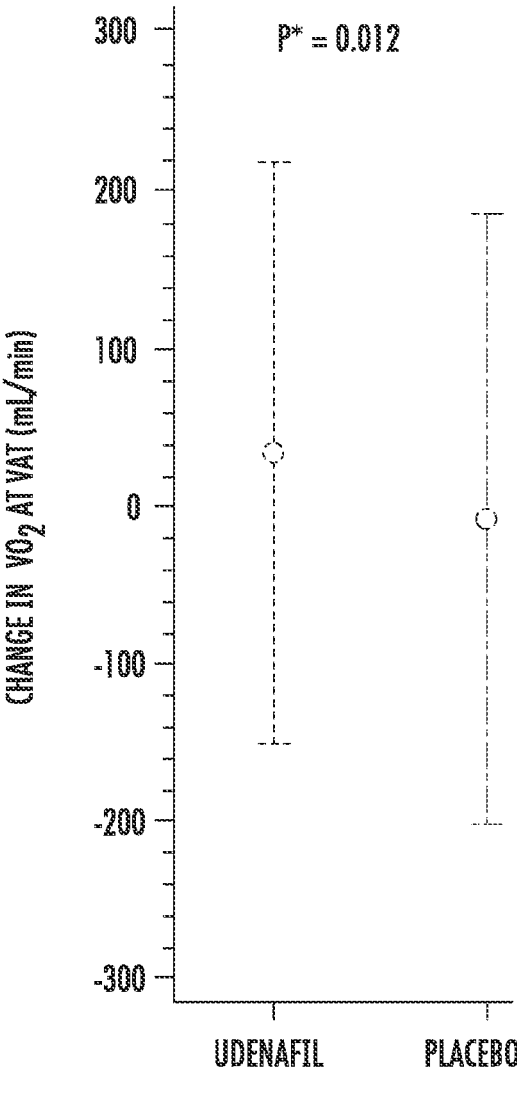
FIG. 3A demonstrates the difference in the change in mean $VO_2$ at VAT from Baseline to Week 26 along with the standard deviation for each treatment arm.
Figure 3B:
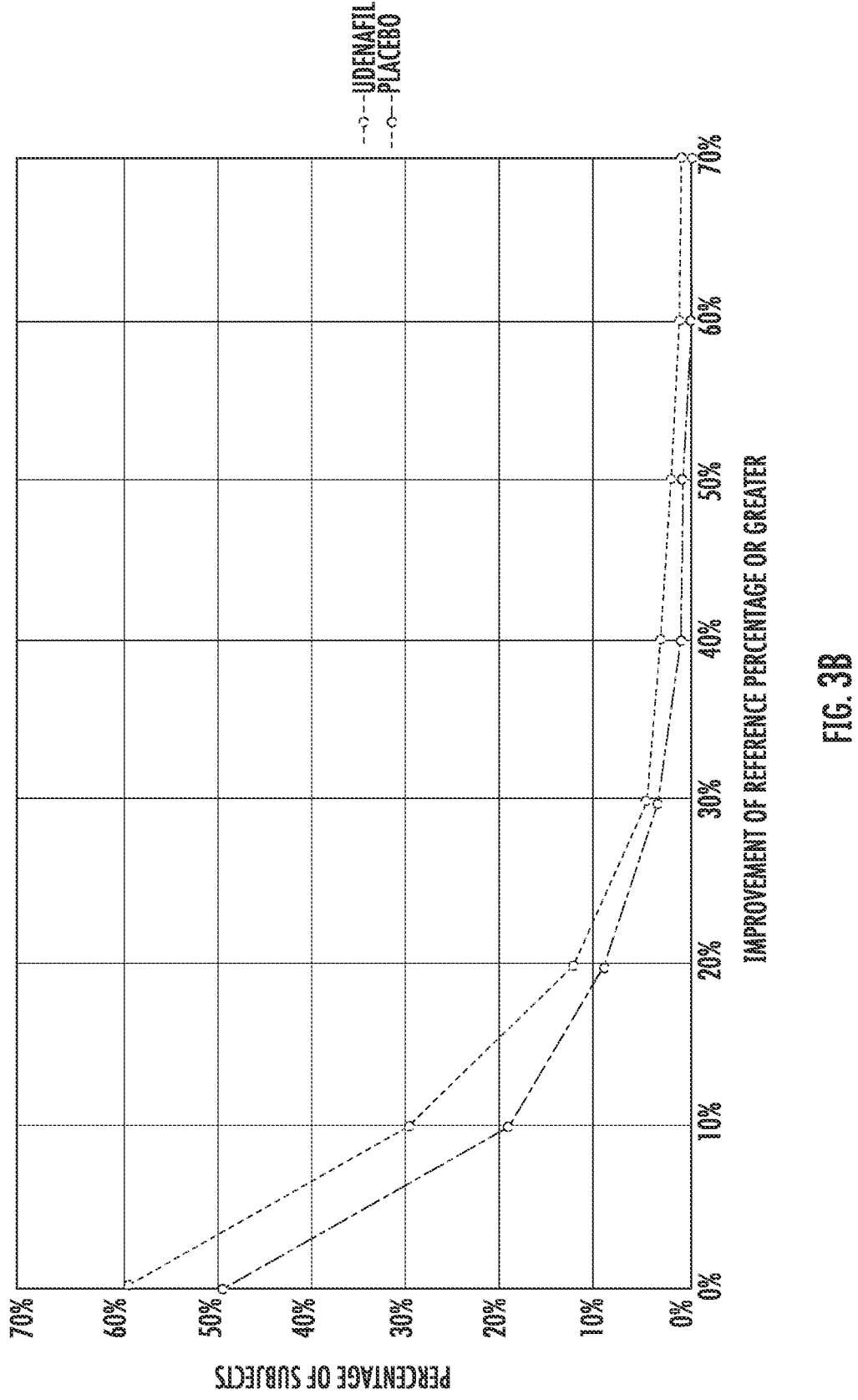
FIG. 3B demonstrates the percentage of subjects (y axis) who demonstrated improvement in $VO_2$ at VAT by the reference percentage or greater (x axis)
Figure 4A:
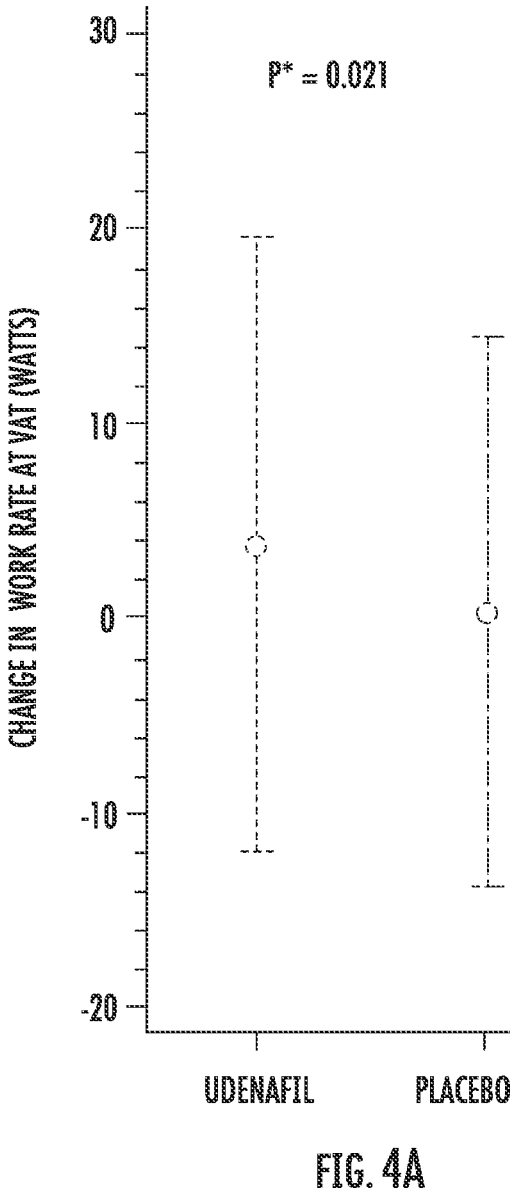
FIG. 4A demonstrates the difference in the change in mean work rate at VAT from Baseline to Week 26 along with the standard deviation for each treatment arm.
Figure 4B:
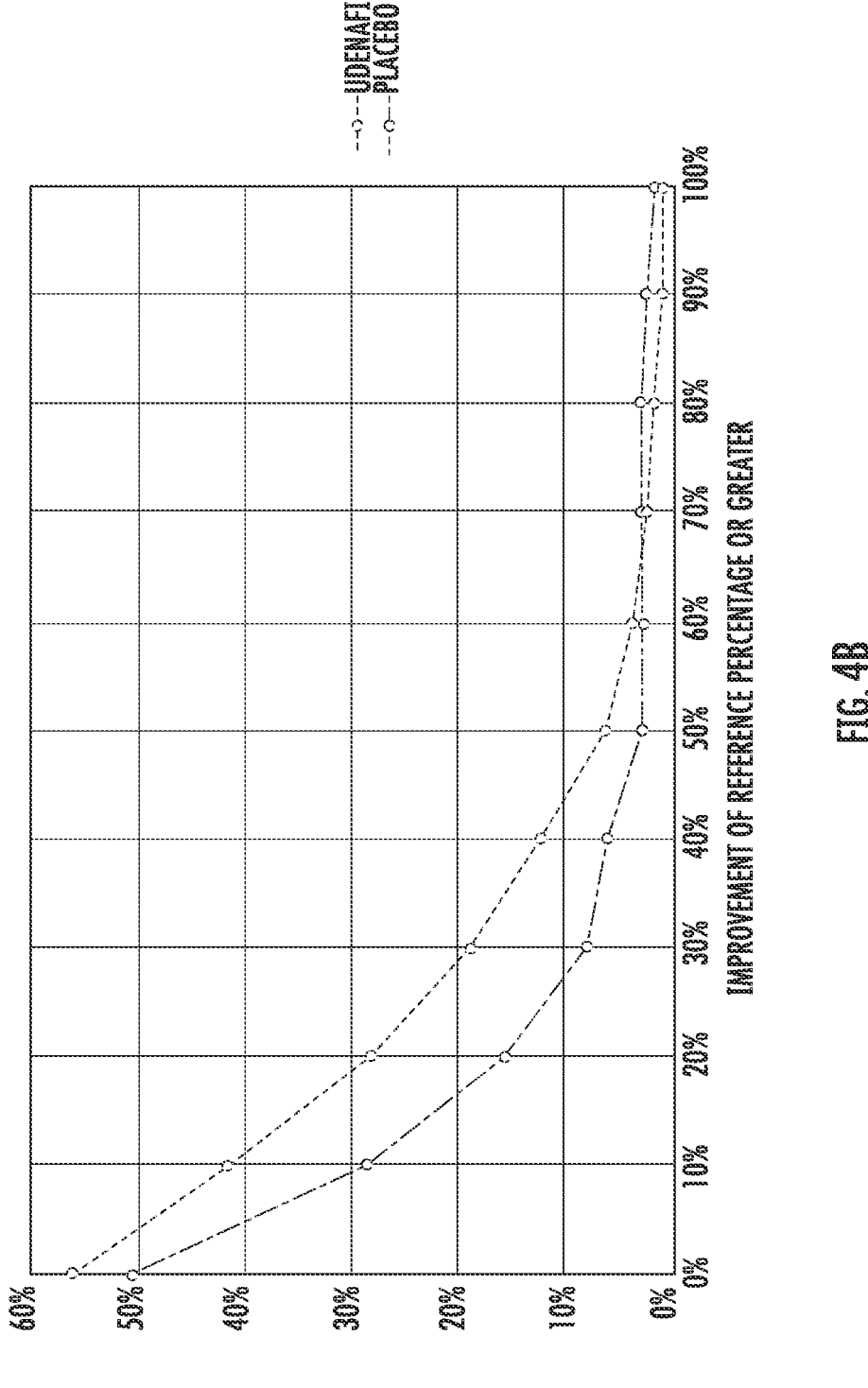
FIG. 4B demonstrates the percentage of subjects (y axis) who demonstrated improvement in work rate by the reference percentage or greater (x axis)
Figure 5:
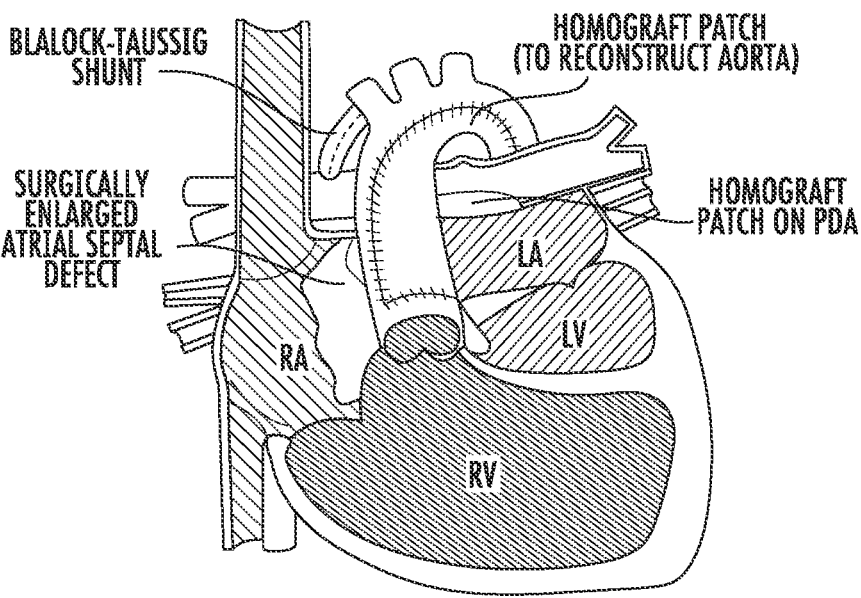
FIG. 5 is a schematic drawing of an exemplary Norwood procedure (Stage 1) of a reconstructed SVHD heart with Hypoplastic Left Heart Syndrome (HLHS)
Figure 6:
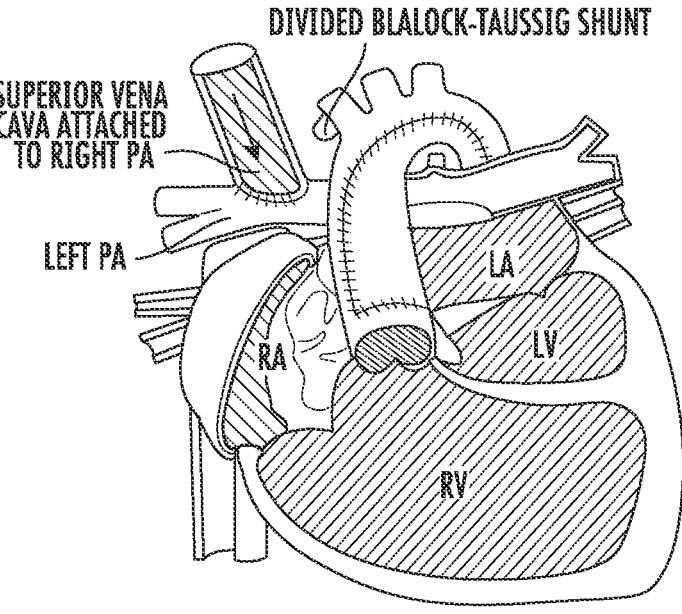
FIG. 6 is a schematic drawing of an exemplary Bidirectional Glenn procedure (Stage 2) of a reconstructed SVHD heart with Hypoplastic Left Heart Syndrome (HLHS)

Resting, submaximal, and maximal exercise measures are presented in Table 2. Maximal exercise data were available for all participants at baseline testing, and for 379 participants at 26-week testing (189 in the udenafil group and 190 in the placebo group). Reasons for absence of data at 26-week testing included patient dropout or errors in data capture (n=14) and participant inability to generate an RER≥1.10 (n=7). There was no difference in the change from baseline to 26-week testing in resting heart rate, respiratory rate, or systolic blood pressure between the udenafil and placebo groups. Peak minute ventilation at baseline (pre-drug exposure) was higher in the placebo group, but there was no difference in the change in minute ventilation between groups. There was a small but statistically significant increase in resting oxygen saturation and a small but statistically significant decrease in diastolic blood pressure in the udenafil group. Analysis at maximal exercise demonstrated an increase in peak $VO_2$ of 44 mL/min (2.8%) in the udenafil group compared to a decline of 3.7 mL/min (−0.2%) in the placebo group, although the difference did not reach statistical significance. FIGS. 2A-2B, p=0.071. Metabolic data for the calculation of $VO_2$ at VAT were available for 351 participants; 170 in the udenafil group and 181 in the placebo group. There was no difference in the baseline demographic or clinical characteristics of this subgroup compared to the larger cohort. Table 7. For those with paired $VO_2$ at VAT data, there was a statistically significant improvement of 29.7 mL/min (2.85%) in the udenafil group compared to a decrease of 9 mL/min (−0.8%) in the placebo group. FIGS. 3A-3B, p=0.023. Ventilatory equivalents of carbon dioxide measured at VAT ($VE/VCO_2$) significantly decreased (improved ventilatory efficiency) by 0.8 in the udenafil group compared to 0.05 in the placebo group (p=0.0114), while the work rate significantly improved by 3.5 Watts (5.2%) in the udenafil group compared to 0.31 Watts (0.5%) in the placebo group. FIGS. 4A-4B, p=0.029.

TABLE 7-continued

Demographic and clinical baseline characteristics for subjects with
versus without paired data for VO$_2$ at VAT; summaries presented
as mean (standard deviation) unless otherwise noted as n (%).

| | Total (n = 400) | | Paired Data (n = 317) | | No Paired Data (n = 83) | | p value* |
|---|---|---|---|---|---|---|---|
| Predominant Ventricular morphology, n (%) | | | | | | | 0.97 |
| Right | 176 | (44.0%) | 138 | (43.5%) | 38 | (45.8%) | |
| Left | 189 | (47.3%) | 151 | (47.6%) | 38 | (45.8%) | |
| Other (indeterminant and biventricular) | 35 | (8.8%) | 28 | (8.8%) | 7 | (8.4%) | |
| Subjects with a patent fenestration, n (%) | 131 | (32.8%) | 104 | (32.8%) | 27 | (32.5%) | 1.0 |
| Height, cm | 163.6 | (9.6) | 164.0 | (9.5) | 162.0 | (10.0) | 0.095 |
| Weight, kg | 58.1 | (13.6) | 58.0 | (13.6) | 58.3 | (13.5) | 0.85 |
| Body mass index, kg/m$^2$ | 21.6 | (4.1) | 21.5 | (4.0) | 22.1 | (4.3) | 0.19 |
| Baseline VO$_2$ at peak exercise | 1594 | (426) | 1614 | (432) | 1518 | (400) | 0.07 |
| Baseline VO$_2$ at the anaerobic threshold | 1030 | (290) | 1034 | (294) | 993 | (251) | 0.44 |

*t-test for continuous variables, Fisher exact test for categorical. Differences between those with and without paired data.

Secondary Aims

Paired echocardiographic data for the measure of MPI were available in 250 participants (63%); 122 in the udenafil group and 128 in the placebo group. Table 3. There was a statistically significant change (decrease shows improvement) in MPI in the udenafil-treated group (−0.02 decrease, improvement) as compared to the placebo group (+0.01 increase, no improvement) (p=0.028). Paired PAT-derived vascular function data were available in 328 participants (81%); 163 in the udenafil group and 165 in the placebo group. There were non-significant improvements in lnRHI in both the udenafil and placebo groups (0.07 vs 0.05, p=0.59). Paired measures of serum BNP level were available in 378 participants (95%); 187 in the udenafil group and 191 in the placebo group. The change in log serum BNP level was not different between groups (p=0.18).

Safety and Tolerability

Udenafil and placebo were well tolerated by study participants. There were no deaths in the study cohort. A total of 24 participants (6%) experienced a serious adverse event; 14 in the udenafil group and 10 in the placebo group. There were 3 events in the udenafil group and 2 events in the placebo group that were thought to have a possible, probable, or definite relationship to study drug. Those that occurred in the udenafil group included unilateral retinal artery and vein thrombosis, transient lower extremity diplegia, and transient dyspnea. Frequent non-serious adverse events thought to have a possible, probable, or definite relationship to study drug are listed in Table 4. Headache, facial flushing, abdominal pain, epistaxis, and erection (male participants) were more common in the udenafil group. There were no reported episodes of priapism. All other adverse events occurred with similar frequency between the groups.

Discussion

The FUEL trial was a phase III clinical trial of udenafil in children with SVHD who have undergone the Fontan operation. Although the relative improvement in peak VO$_2$ in the udenafil group did not reach statistical significance when compared between treatment arms, treatment with udenafil did lead to statistically significant improvements in pre- specified secondary outcome measures of sub-maximal exercise. Participants randomized to udenafil had superior gains in oxygen consumption, work rate, ventilatory efficiency at the anaerobic threshold, and the myocardial performance index. A relative improvement in the PAT-derived reactive hyperemia index was not seen. Overall, udenafil was well tolerated with few serious adverse events and side effects limited to those known to be associated with PDE5 inhibitor therapy. Goldberg D J, French B, McBride M G, Marino B S, Mirarchi N, Hanna B D, Wernovsky G, Paridon S M and Rychik J. Impact of oral sildenafil on exercise performance in children and young adults after the fontan operation: a randomized, double-blind, placebo-controlled, crossover trial. Circulation. 123(11):1185-1193 (May 22, 2011); Goldberg D J, Zak V, Goldstein B H, McCrindle B W, Menon S C, Schumacher K R, Payne R M, Rhodes J, McHugh K E, Penny D J, Trachtenberg F, Hamstra M S, Richmond M E, Frommelt P C, Files M D, Yeager J L, Pemberton V L, Stylianou M P, Pearson G D, Paridon S M and Pediatric Heart Network I. Design and rationale of the Fontan Udenafil Exercise Longitudinal (FUEL) trial. Am Heart J. 201:1-8 (July 2018); and Chang H J, Song S, Chang S A, Kim H K, Jung H O, Choi J H, Lee J S, Kim K H, Jeong J O, Lee J H and Kim D K. Efficacy and Safety of Udenafil for the Treatment of Pulmonary Arterial Hypertension: a Placebo-controlled, Double-blind, Phase IIb Clinical Trial. Clin Ther. 41(8):1499-1507 (August 2019).

While the Fontan operation and its modifications have led to the survival of a generation of patients with otherwise terminal SVHD, the circulation created by that procedure suffers from inherent physiologic flaws: central venous pressure is chronically elevated and cardiac output is chronically diminished. Gewillig M and Goldberg D J. Failure of the fontan circulation. Heart Fail Clin. 10(1):105-116 (January 2014); Egbe A C, Connolly H M, Miranda W R, Ammash N M, Hagler D J, Veldtman G R and Borlaug B A. Hemodynamics of Fontan Failure: The Role of Pulmonary Vascular Disease. Circ Heart Fail. 10(12): e004515 (September 2017); and Gewillig M, Brown S C, Eyskens B, Heying R, Ganame J, Budts W, La Gerche A and Gorenflo M. The Fontan circulation: who controls cardiac output? Interact Cardiovasc Thorac Surg. 10(3):428-433 (March 2010). Fundamental limitations to cardiovascular efficiency in the Fontan circulation are many, and commonly include abnormalities in pulmonary vascular resistance, single ventricular diastolic function, systemic and pulmonary vascular endothelial dysfunction, pathologic vascular remodeling, and others. Egbe A C, Connolly H M, Miranda W R, Ammash N M, Hagler D J, Veldtman G R and Borlaug B A. Hemodynamics of Fontan Failure: The Role of Pulmonary Vascular Disease. *Circ Heart Fail.* 10(12): e004515 (September 2017); Averin K, Hirsch R, Seckeler MD, Whiteside W, Beekman R H, 3rd and Goldstein B H. Diagnosis of occult diastolic dysfunction late after the Fontan procedure using a rapid volume expansion technique. *Heart.* 102(14): 1109-1114 (Jul. 15, 2016); Goldstein B H, Connor C E, Gooding L and Rocchini A P. Relation of systemic venous return, pulmonary vascular resistance, and diastolic dysfunction to exercise capacity in patients with single ventricle receiving fontan palliation. *Am J Cardiol.* 105(8):1169-1175 (Apr. 15, 2010); Hays B S, Baker M, Laib A, Tan W, Udholm S, Goldstein B H, Sanders S P, Opotowsky A R and Veldtman G R. Histopathological abnormalities in the central arteries and veins of Fontan subjects. *Heart.* 104(4): 324-331 (February 2018); Khambadkone S, Li J, de Leval M R, Cullen S, Deanfield J E and Redington A N. Basal pulmonary vascular resistance and nitric oxide responsiveness late after Fontan-type operation. *Circulation.* 107(25): 3204-3208 (Jul. 1, 2003); Mitchell M B, Campbell D N, Ivy D, Boucek M M, Sondheimer H M, Pietra B, Das B B and Coll J R. Evidence of pulmonary vascular disease after heart transplantation for Fontan circulation failure. *J Thorac Cardiovasc Surg.* 128(5):693-702 (November 2004); and Sarkola T, Jaeggi E, Slorach C, Hui W, Bradley T and Redington A N. Assessment of vascular remodeling after the Fontan procedure using a novel very high resolution ultrasound method: arterial wall thinning and venous thickening in late follow-up. *Heart Vessels.* 28(1):66-75 (January 2013). Although each pathologic feature of the circulation may represent a potential therapeutic target, pharmacotherapy with agents designed to lower pulmonary vascular resistance make intuitive sense given their broad tolerability, their efficacy for the treatment of pulmonary hypertension, and the unique role of pulmonary vascular resistance as a modulator of cardiac output after Fontan. Egbe A C, Connolly H M, Miranda W R, Ammash N M, Hagler D J, Veldtman G R and Borlaug B A. Hemodynamics of Fontan Failure: The Role of Pulmonary Vascular Disease. *Circ Heart Fail.* 10(12): e004515 (September 2017).

Prior studies with other pulmonary vasodilators in those with the Fontan circulation have been equivocal. Agnoletti G, Gala S, Ferroni F, Bordese R, Appendini L, Pace Napoleone C and Bergamasco L. Endothelin inhibitors lower pulmonary vascular resistance and improve functional capacity in patients with Fontan circulation. *J Thorac Cardiovasc Surg.* 153(6):1468-1475 (June 2017); Goldberg D J, French B, McBride M G, Marino B S, Mirarchi N, Hanna B D, Wernovsky G, Paridon S M and Rychik J. Impact of oral sildenafil on exercise performance in children and young adults after the fontan operation: a randomized, double-blind, placebo-controlled, crossover trial. *Circulation.* 123 (11):1185-1193 (May 22, 2011); Hebert A, Mikkelsen UR, Thilen U, Idorn L, Jensen A S, Nagy E, Hanseus K, Sorensen K E and Sondergaard L. Bosentan improves exercise capacity in adolescents and adults after Fontan operation: the TEMPO (Treatment With Endothelin Receptor Antagonist in Fontan Patients, a Randomized, Placebo-Controlled, Double-Blind Study Measuring Peak Oxygen Consumption) study. *Circulation.* 130(23):2021-2030 (Dec. 2, 2014); Mori H, Park I S, Yamagishi H, Nakamura M, Ishikawa S, Takigiku K, Yasukochi S, Nakayama T, Saji T and Nakanishi T. Sildenafil reduces pulmonary vascular resistance in single ventricular physiology. *Int J Cardiol.* 221:122-127 (Oct. 15, 2016); Rhodes J, Ubeda-Tikkanen A, Clair M, Fernandes S M, Graham D A, Milliren C E, Daly K P, Mullen M P and Landzberg M J. Effect of inhaled iloprost on the exercise function of Fontan patients: a demonstration of concept. *Int J Cardiol.* 168(3):2435-2440 (Oct. 3, 2013); Schuuring M J, Vis J C, van Dijk A P, van Melle J P, Vliegen H W, Pieper P G, Sieswerda G T, de Bruin-Bon R H, Mulder B J and Bouma B J. Impact of bosentan on exercise capacity in adults after the Fontan procedure: a randomized controlled trial. *Eur J Heart Fail.* 15(6):690-698 (June 2013); Tunks R D, Barker P C, Benjamin D K, Jr., Cohen-Wolkowiez M, Fleming G A, Laughon M, Li J S and Hill K D. Sildenafil exposure and hemodynamic effect after Fontan surgery. *Pediatr Crit Care Med.* 15(1):28-34 (January 2014); Van De Bruaene A, La Gerche A, Claessen G, De Meester P, Devroe S, Gillijns H, Bogaert J, Claus P, Heidbuchel H, Gewillig M and Budts W. Sildenafil improves exercise hemodynamics in Fontan patients. *Circ Cardiovasc Imaging.* 7(2):265-273 (March 2014); Goldberg D J, French B, Szwast A L, McBride M G, Marino B S, Mirarchi N, Hanna B D, Wernovsky G, Paridon S M and Rychik J. Impact of sildenafil on echocardiographic indices of myocardial performance after the Fontan operation. *Pediatr Cardiol.* 33(5): 689-696 (June 2012); and Giardini A, Balducci A, Specchia S, Gargiulo G, Bonvicini M and Picchio F M. Effect of sildenafil on haemodynamic response to exercise and exercise capacity in Fontan patients. *Eur Heart J.* 29(13):1681-1687 (July 2008). A number of small, single-site studies across a range of classes of pulmonary vasodilators have demonstrated an acute improvement after a single dose, but these did not look at sustained effect or chronic usage. Rhodes J, Ubeda-Tikkanen A, Clair M, Fernandes S M, Graham D A, Milliren C E, Daly K P, Mullen M P and Landzberg M J. Effect of inhaled iloprost on the exercise function of Fontan patients: a demonstration of concept. *Int J Cardiol.* 168(3):2435-2440 (Oct. 3, 2013); Tunks R D, Barker P C, Benjamin D K, Jr., Cohen-Wolkowiez M, Fleming G A, Laughon M, Li J S and Hill K D. Sildenafil exposure and hemodynamic effect after Fontan surgery. *Pediatr Crit Care Med.* 15(1):28-34 (January 2014); Van De Bruaene A, La Gerche A, Claessen G, De Meester P, Devroe S, Gillijns H, Bogaert J, Claus P, Heidbuchel H, Gewillig M and Budts W. Sildenafil improves exercise hemodynamics in Fontan patients. *Circ Cardiovasc Imaging.* 7(2):265-273 (March 2014); and Giardini A, Balducci A, Specchia S, Gargiulo G, Bonvicini M and Picchio F M. Effect of sildenafil on haemodynamic response to exercise and exercise capacity in Fontan patients. *Eur Heart J.* 29(13):1681-1687 (July 2008). There have been two moderate-sized studies that have evaluated the use of endothelin-receptor antagonists in adolescents and adults after Fontan, but these two trials demonstrated conflicting results and did not undergo phase I testing in this cohort. Hebert A, Mikkelsen U R, Thilen U, Idorn L, Jensen A S, Nagy E, Hanseus K, Sorensen K E and Sondergaard L. Bosentan improves exercise capacity in adolescents and adults after Fontan operation: the TEMPO (Treatment With Endothelin Receptor Antagonist in Fontan Patients, a Randomized, Placebo-Controlled, Double-Blind Study Measuring Peak Oxygen Consumption) study. *Circulation.* 130(23):2021-2030 (Dec. 2, 2014); and Schuuring M J, Vis J C, van Dijk A P, van Melle J P, Vliegen H W, Pieper P G, Sieswerda G T, de Bruin-Bon R H, Mulder B J and Bouma B J. Impact of bosentan on exercise capacity in adults after the Fontan procedure: a randomized controlled trial. *Eur J Heart Fail.* 15(6):690-698 (June 2013). Furthermore, in the study that was suggestive of a benefit, this benefit was associated with a drop in hemoglobin level, a side effect that is likely to offset the presumed benefit of the drug. Hebert A, Mikkelsen U R, Thilen U, Idorn L, Jensen A S, Nagy E, Hanseus K, Sorensen K E and Sondergaard L. Bosentan improves exercise capacity in adolescents and adults after Fontan operation: the TEMPO (Treatment With Endothelin Receptor Antagonist in Fontan Patients, a Randomized, Placebo-Controlled, Double-Blind Study Measuring Peak Oxygen Consumption) study. *Circulation.* 130(23):2021-2030 (Dec. 2, 2014). The FUEL trial is the first large-scale, multi-institutional study to suggest a physiologic benefit associated with the use of a specific pulmonary vasodilator at a dose determined by phase I clinical testing in adolescents with SVHD following Fontan palliation.

The challenges of living with Fontan physiology are well demonstrated by evaluations of exercise performance. Adolescents with Fontan physiology have diminished exercise capacity relative to healthy peers, a difference that is accentuated over time and associated with an increased rate of hospitalization and heart failure symptoms. Fernandes S M, McElhinney D B, Khairy P, Graham D A, Landzberg M J and Rhodes J. Serial cardiopulmonary exercise testing in patients with previous Fontan surgery. *Pediatr Cardiol.* 31(2):175-180 (February 2010); Giardini A, Hager A, Pace Napoleone C and Picchio F M. Natural history of exercise capacity after the Fontan operation: a longitudinal study. *Ann Thorac Surg.* 85(3):818-21 (March 2008); Jenkins P C, Chinnock R E, Jenkins K J, Mahle W T, Mulla N, Sharkey A M and Flanagan M F. Decreased exercise performance with age in children with hypoplastic left heart syndrome. *J Pediatr.* 152(4):507-512 (April 2008); Paridon S M, Mitchell P D, Colan S D, Williams R V, Blaufox A, Li J S, Margossian R, Mital S, Russell J, Rhodes J and Pediatric Heart Network I. A cross-sectional study of exercise performance during the first 2 decades of life after the Fontan operation. *J Am Coll Cardiol.* 52(2):99-107 (Jul. 8, 2008); Atz A M, Zak V, Mahony L, Uzark K, D'Agincourt N, Goldberg D J, Williams R V, Breitbart R E, Colan S D, Burns K M, Margossian R, Henderson H T, Korsin R, Marino B S, Daniels K, McCrindle B W and Pediatric Heart Network I. Longitudinal Outcomes of Patients With Single Ventricle After the Fontan Procedure. *J Am Coll Cardiol.* 69(22): 2735-2744 (Jun. 6, 2017); Diller G P, Dimopoulos K, Okonko D, Li W, Babu-Narayan S V, Broberg C S, Johansson B, Bouzas B, Mullen M J, Poole-Wilson P A, Francis D P and Gatzoulis M A. Exercise intolerance in adult congenital heart disease: comparative severity, correlates, and prognostic implication. *Circulation.* 112(6):828-35 (Aug. 9, 2005); Diller G P, Giardini A, Dimopoulos K, Gargiulo G, Muller J, Derrick G, Giannakoulas G, Khambadkone S, Lammers A E, Picchio F M, Gatzoulis M A and Hager A. Predictors of morbidity and mortality in contemporary Fontan patients: results from a multicenter study including cardiopulmonary exercise testing in 321 patients. *Eur Heart J.* 31(24):3073-3083 (December 2010); Cunningham J W, Nathan A S, Rhodes J, Shafer K, Landzberg M J and Opotowsky A R. Decline in peak oxygen consumption over time predicts death or transplantation in adults with a Fontan circulation. *Am Heart J.* 189:184-192 (July 2017); and Udholm S, Aldweib N, Hjortdal V E and Veldtman G R. Prognostic power of cardiopulmonary exercise testing in Fontan patients: a systematic review. *Open Heart.* 5(1): e000812 (July 2018). Exercise capacity below 50% predicted for age and sex is the approximate threshold beyond which circulation-associated morbidities become common and typically occurs during the third decade of life, but may occur earlier. Diller G P, Giardini A, Dimopoulos K, Gargiulo G, Muller J, Derrick G, Giannakoulas G, Khambadkone S, Lammers A E, Picchio F M, Gatzoulis M A and Hager A. Predictors of morbidity and mortality in contemporary Fontan patients: results from a multicenter study including cardiopulmonary exercise testing in 321 patients. *Eur Heart J.* 31(24):3073-3083 (December 2010). The ability to improve exercise capacity, as a marker of improved circulatory function more generally, is likely to be critical to the long-term health of those who have undergone the Fontan procedure. This trial suggests that udenafil may help to improve key measures of exercise capacity following pharmacologic intervention in Fontan patients.

The FUEL trial was powered to detect a change in peak $VO_2$ because it is relatively easy to measure and because it has been used in previous trials as an accepted surrogate for cardiac events. Dallaire F, Wald R M and Marelli A. The Role of Cardiopulmonary Exercise Testing for Decision Making in Patients with Repaired Tetralogy of Fallot. *Pediatr Cardiol.* 38(6):1097-1105 (August 2017); Mancini D, LeJemtel T and Aaronson K. Peak VO(2): a simple yet enduring standard. *Circulation.* 101(10):1080-1082 (March 2000); Okonko D O, Grzeslo A, Witkowski T, Mandal A K, Slater R M, Roughton M, Foldes G, Thum T, Majda J, Banasiak W, Missouris C G, Poole-Wilson P A, Anker S D and Ponikowski P. Effect of intravenous iron sucrose on exercise tolerance in anemic and nonanemic patients with symptomatic chronic heart failure and iron deficiency FERRIC-HF: a randomized, controlled, observer-blinded trial. *J Am Coll Cardiol.* 51(2):103-112 (Jan. 15, 2008); and Redfield M M, Chen H H, Borlaug B A, Semigran M J, Lee K L, Lewis G, LeWinter M M, Rouleau J L, Bull D A, Mann D L, Deswal A, Stevenson L W, Givertz M M, Ofili E O, O'Connor C M, Felker G M, Goldsmith S R, Bart B A, McNulty S E, Ibarra J C, Lin G, Oh J K, Patel M R, Kim R J, Tracy R P, Velazquez E J, Anstrom K J, Hernandez A F, Mascette A M, Braunwald E and Trial R. Effect of phosphodiesterase-5 inhibition on exercise capacity and clinical status in heart failure with preserved ejection fraction: a randomized clinical trial. *JAMA.* 309(12):1268-1277 (Mar. 27, 2013). However, while peak $VO_2$ may be useful as a surrogate for many cardiovascular disease states, it may not be as relevant an endpoint after the Fontan operation. In this unique physiology, central venous pressure rather than right ventricular contraction is the primary driver of transpulmonary blood flow and, therefore, cardiac output. Gewillig M and Goldberg D J. Failure of the fontan circulation. *Heart Fail Clin.* 10(1):105-116 (January 2014); Egbe A C, Connolly H M, Miranda W R, Ammash N M, Hagler D J, Veldtman G R and Borlaug B A. Hemodynamics of Fontan Failure: The Role of Pulmonary Vascular Disease. *Circ Heart Fail.* 10(12): e004515 (September 2017); Gewillig M, Brown S C, Eyskens B, Heying R, Ganame J, Budts W, La Gerche A and Gorenflo M. The Fontan circulation: who controls cardiac output? *Interact Cardiovasc Thorac Surg.* 10(3):428-433 (March 2010); and Goldberg D J, Avitabile C M, McBride M G and Paridon S M. Exercise capacity in the Fontan circulation. *Cardiol Young.* 23(6):824-830 (December 2013). As the demand for cardiac output increases with exertion, central venous pressure in the Fontan circulation must rise to meet that demand, but eventually reaches a critical ceiling beyond which it can rise no further. Navaratnam D, Fitzsimmons S, Grocott M, Rossiter H B, Emmanuel Y, Diller G P, Gordon-Walker T, Jack S, Sheron N, Pappachan J, Pratap J N, Vettukattil J J and Veldtman G.

Exercise-Induced Systemic Venous Hypertension in the Fontan Circulation. *Am J Cardiol.* 117(10):1667-1671 (May 15, 2016). At submaximal exertion, the elevation in central venous pressure does not reach the physiologic ceiling and thus outcomes at this level of exercise may be more sensitive to pharmacologic manipulation of the pulmonary vasculature. This is demonstrated by the relatively high ratio of both oxygen consumption and work rate at the anaerobic threshold compared to peak exercise, and is different from the physiology for those with a sub-pulmonary ventricle in whom central venous pressure changes very little during exercise and for whom trends in improvement or decline in $VO_2$ at VAT and peak $VO_2$ are usually equivalent.

Despite the importance of the findings reported here, there are limitations to this trial. First, to minimize burden to participants, the study design did not include detailed measures of hemodynamics such as might be obtained with cardiac magnetic resonance imaging or invasive catheterization study. Additionally, evaluation of the PAT outcome did not reveal a benefit to udenafil over placebo. [?] Further interrogation of the multiple measures provided by these studies was not performed in this initial analysis but will be the subject of future analyses. Finally, the duration of the FUEL trial precluded a long-term assessment of safety, although this is being addressed by the ongoing FUEL open-label extension study.

Treatment with udenafil (87.5 mg twice daily), in addition to standard therapy, was not associated with a statistically significant improvement in oxygen consumption at peak exercise but did demonstrate statistically significant improvements in multiple measures of exercise performance at the ventilatory anaerobic threshold. As the first large, multicenter, placebo-controlled, randomized trial to demonstrate a measurable physiologic benefit for Fontan patients, the FUEL trial represents a milestone in the nearly 50-year experience with the Fontan circulation and serves as a model of how public-private partnership can advance science in congenital heart disease. Further study is warranted to determine if udenafil is selectively beneficial for subpopulations within the larger cohort with SVHD, and to evaluate the long-term tolerability and safety of treatment.

The disclosures cited in this EXAMPLE 2 are incorporated herein by reference in their entireties as if fully set forth herein.

Example 3

Formulation of Udenafil Tablet

An exemplary formulation of a tablet containing 87.5 mg of the udenafil is detailed in Table 11. The udenafil formulation as reported in Table 11 was used with Fontan patients enrolled in the FUEL trial, which is discussed in Examples 1 and 2 above.

TABLE 11

Composition of Udenafil Tablets, 87.5 mg.

| Component | Quality Standard | Function | Quantity (mg/tablet) |
|---|---|---|---|
| Core tablet | | | |
| Udenafil | In-house | Active | about 87.5 |
| Lactose monohydrate | NF | Diluent | about 100.00 |
| Corn starch | NF | Diluent | about 20.00 |
| Low substituted hydroxypropyl cellulose | NF | Disintegrant | about 12.50 |

50

TABLE 11-continued

Composition of Udenafil Tablets, 87.5 mg.

| Component | Quality Standard | Function | Quantity (mg/tablet) |
|---|---|---|---|
| Colloidal silicon dioxide | NF | Disintegrant | about 12.50 |
| Hydroxypropyl cellulose | NF | Binder | about 7.50 |
| Purified water | USP | Granulating solvent | NA[1] |
| Talc | USP | Glidant | about 7.50 |
| Magnesium stearate | NF | Lubricant | about 2.50 |
| Total core tablet weight | | | about 250.0 mg |
| Tablet coating | | | |
| Purified water | USP | Solvent | NA[1] |
| Opadry white[3] | In-house | Coating material | about 8.00[2] |
| Total Tablet Weight | | | about 258.00 |

[1]Purified Water, USP is removed during the manufacturing process and is not part of the final formulation.
[2]Based on a nominal coating weight gain of 3.2% w/w
[3]Opadry white contains hypromellose, hydroxypropyl cellulose, titanium dioxide, and polyethylene glycol

Example 4

Udenafil Effect on Echocardiographic Indices of Myocardial Performance in SVHD Subjects with Fontan Palliation An objective of the FUEL Trial was to determine the effect of udenafil on echocardiographic measures of myocardial performance in adolescents, ages about 12 to about 18, with a functional single-ventricle physiology after Fontan surgery. The FUEL Trial was a randomized, double-blind, placebo-controlled, trial and was conducted in adolescents, ages about 12 to about 18, after the Fontan operation, at 30 different sites located in the United States (26), Canada (2) and South Korea (2) The Fontan patients were randomized to receive placebo or udenafil (87.5 mg twice daily) for 26 weeks.

Each subject underwent an echocardiogram at the start and finish of the 26 weeks. Paired echocardiographic data for the measure of MPI were available in 250 participants (63%); 122 in the udenafil group and 128 in the placebo group. Table 3. There was a statistically significant change in MPI in the udenafil treated group (−0.02 decrease, improvement) as compared to the placebo group (+0.01 increase, no improvement) (p=0.028). The change in the MPI was determined by velocities obtained from blood pool Doppler assessment of the inflow and outflow tract of the single functioning dominant ventricle. All measurements were made by the echocardiography core lab at the Children's Hospital of Wisconsin. The subjects treated with udenafil demonstrated statistically significant improvement (decrease shows improvement) in their myocardial performance index (MPI), p=0.028, compared to subjects taking placebo over the same time period.

These data demonstrate an improvement in MPI in the udenafil group relative to the placebo group (−0.02 vs +0.01, p=0.028). Myocardial performance is an important factor in the long-term health of those with SVHD, including those with SVHD who have undergone Fontan surgery, and improvement in this aspect of physiology complements the improvement noted in exercise performance and suggests that the benefit of treatment with udenafil may be multifactorial.

All disclosures, including all patents, patent documents, articles, abstracts, errata and publications, that are referenced or cited herein, including application for U.S. patent Ser. No. 14/788,211, U.S. Patent Publication No. 2019/0030037, U.S. Pat. No. 10,137,128, and application for U.S. patent Ser. No. 15/887,523, U.S. Patent Publication No. 2018/0169103, U.S. Pat. No. 10,653,698, Goldberg, D. J. et al.: Results of the FUEL Trial. *Circulation.* 141:641-651 (Feb. 25, 2020) and Goldberg, D. J. et al.: Correction to: Results of the FUEL Trial. *Circulation.* 142:e31 (Jul. 14, 2020), are incorporated herein by reference in their entireties, as if each were individually and completely incorporated and set forth herein.

In case of conflict with other related earlier filed applications cited under "Related Applications," this present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

Having described our invention, we claim:

1. A method of improving a Fontan patient's exercise capacity, comprising: administering 87.5 mg of udenafil or a pharmaceutically acceptable salt thereof twice daily to the Fontan patient, wherein said method increases oxygen consumption at the ventilatory anaerobic threshold (VAT).

2. The method according to claim 1, wherein said method improves ventilatory equivalents of carbon dioxide (VE/$VCO_2$) at VAT.

3. The method according to claim 1, wherein said method increases work rate at VAT.

4. The method according to claim 2, wherein said method increases work rate at VAT.

5. The method according to claim 1, wherein said method increases oxygen consumption at peak exercise capacity.

6. The method according to claim 5, wherein said method improves ventilatory equivalents of carbon dioxide (VE/$VCO_2$) at VAT.

7. The method according to claim 5, wherein said method increases work rate at VAT.

8. The method according to claim 6, wherein said method increases work rate at VAT.

9. The method according to claim 1, wherein said method results in minimal or no side effects caused to the Fontan patient.

10. The method according to claim 1, wherein the patient is an adolescent.

11. The method according to claim 1, wherein the patient is between about 12 and about 19 years old.

12. The method according to claim 1, wherein the patient is between about 12 and about 18 years old.

13. The method according to claim 1, wherein the patient is an adult.

* * * * *